United States Patent
Chase et al.

(10) Patent No.: US 12,110,503 B2
(45) Date of Patent: Oct. 8, 2024

(54) METHOD FOR DIFFERENTIATION OF OCULAR CELLS AND USE THEREOF

(71) Applicant: FUJIFILM Cellular Dynamics, Inc., Madison, WI (US)

(72) Inventors: Lucas Chase, Madison, WI (US); Kyle Wallace, Madison, WI (US); Benjamin Meline, Madison, WI (US); Andrew Dias, Madison, WI (US); Brandon Shelley, Madison, WI (US); Marisa Fenn, Madison, WI (US); Debjani Phillips, Madison, WI (US); Matthew Sternfeld, Madison, WI (US); Nathan Meyer, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 616 days.

(21) Appl. No.: 17/049,018

(22) PCT Filed: Apr. 22, 2019

(86) PCT No.: PCT/US2019/028557
§ 371 (c)(1),
(2) Date: Oct. 19, 2020

(87) PCT Pub. No.: WO2019/204817
PCT Pub. Date: Oct. 24, 2019

(65) Prior Publication Data
US 2021/0238546 A1    Aug. 5, 2021

Related U.S. Application Data

(60) Provisional application No. 62/660,899, filed on Apr. 20, 2018.

(51) Int. Cl.
| | |
|---|---|
| C12N 5/079 | (2010.01) |
| A61K 35/30 | (2015.01) |
| C12N 5/0793 | (2010.01) |
| G01N 33/68 | (2006.01) |

(52) U.S. Cl.
CPC ............ *C12N 5/0621* (2013.01); *A61K 35/30* (2013.01); *C12N 5/062* (2013.01); *G01N 33/68* (2013.01); *C12N 2500/38* (2013.01); *C12N 2501/105* (2013.01); *C12N 2501/115* (2013.01); *C12N 2501/15* (2013.01); *C12N 2501/155* (2013.01); *C12N 2501/415* (2013.01); *C12N 2501/727* (2013.01); *C12N 2501/734* (2013.01); *C12N 2506/45* (2013.01)

(58) Field of Classification Search
CPC .................................................. C12N 5/0621
See application file for complete search history.

(56) References Cited

U.S. PATENT DOCUMENTS

| | | |
|---|---|---|
| 10,240,201 B2 | 3/2019 | Takahashi et al. |
| 2013/0224156 A1 | 8/2013 | Takahashi et al. |
| 2017/0067017 A1* | 3/2017 | Meyer ............... C12N 5/0081 |
| 2017/0313981 A1* | 11/2017 | Kuwahara ............ A61P 27/02 |

FOREIGN PATENT DOCUMENTS

| | | |
|---|---|---|
| WO | WO2008129554 | 10/2008 |
| WO | WO2013114360 | 8/2013 |
| WO | WO 2014-030749 | 2/2014 |
| WO | WO2014145108 | 9/2014 |
| WO | WO2014174492 | 10/2014 |
| WO | WO2015054526 | 4/2015 |
| WO | WO 2015-109148 | 7/2015 |
| WO | WO2015125941 | 8/2015 |
| WO | WO 2016-103269 | 6/2016 |
| WO | WO2016108219 | 7/2016 |
| WO | WO2017/044483 | 3/2017 |
| WO | WO2017/091844 | 6/2017 |

OTHER PUBLICATIONS

Lupo et al. Multiple roles of Activin/Nodal, bone morphogenic protein, fibroblast growth factor and Wnt/β-catenin signalling in the anterior neural patterning of adherent human embryonic stem cell cultures. Open Biology 2013, 3:120167. (Year: 2013).*
Yanai et al. Differentiation of human embryonic stem cells using size-controlled embryoid bodies and negative cell selection in the production of photoreceptor precursor cells. Tissue Engineering: Part C 2013, 19;10:755-764. (Year: 2013).*
Das et al. Cyclin D1 fine-tunes the neurogenic output of embryonic retinal progenitor cells. Neural Development 2009, 4;15:1-24. (Year: 2009).*
J. Meyer et al. Modeling early retinal development with human embryonic and induced pluripotent stem cells. PNAS 2009, 106;39. Supplementary material. (Year: 2009).*
Kruczek et al. Differentiation and transplantation of embryonic stem cell-derived cone photoreceptors into a mouse model of end-stage retinal degeneration. Stem Cell Reports 2017, 8:1659-1674. (Year: 2017).*
J. Meyer et al. Optic vesicle-like structures derived from human pluripotent stem cells facilitate a customized approach to retinal disease treatment. Stem Cells 2011, 29:1206-1218. (Year: 2011).*
Comyn et al., "Induced pluripotent stem cell therapies for retinal disease", Curr Opin Neurol., 23(1):4-9, Feb. 2010.
Günhan et al., "Ectopic Photoreceptors and Cone Bipolar Cells in the Developing and Mature Retina", Journal of Neuroscience, 23(4):1383-1389, Feb. 15, 2003.
Haverkamp, et al. "Immunocytochemical description of five bipolar cell types of the mouse retina", J Comp Neurol., 455(4):463-76, Jan. 20, 2003.

(Continued)

*Primary Examiner* — Allison M Fox
*Assistant Examiner* — Jennifer S Spence
(74) *Attorney, Agent, or Firm* — Parker Highlander PLLC

(57) ABSTRACT

Provided herein are methods of producing a photoreceptor precursor (PRP) cell population derived from stem cells. Further provided herein are methods of using the PRP cell populations, such as for therapeutics.

29 Claims, 76 Drawing Sheets

(56) References Cited

OTHER PUBLICATIONS

International Preliminary Report on Patentability for PCT/US2019/028557 dated Oct. 20, 2020, 10 pages.
International Search Report and Written Opinion for PCT/US2019/028557 dated Jul. 15, 2019, 17 pages.
Meyer et al., "Modeling early retinal development with human embryonic and induced pluripotent stem cells", PNAS, 106(39): 16698-16703, 2009.
Pearson et al., "Restoration of vision after transplantation of photoreceptors", Nature, 485(7396):99-103, May 3, 2012.
Search Report for European Patent Application No. 19728764.2 dated Nov. 3, 2021, 7 pages.
Weed et al., "Strategies for retinal cell generation from human pluripotent stem cells", Stem Cell Investigation, vol. 4, Jul. 25, 2017, p. 65.
Xie et al., "Differentiation of Retinal Ganglion Cells and Photoreceptor Precursors from Mouse Induced Pluripotent Stem Cells Carrying an Atoh7/Math5 Lineage Reporter", PLOS|One, 9(11), e112175 (Nov. 2014).
Zhao et al., "Generation of Human Corneal Endothelial Cells via In Vitro Ocular Linneage Restriction of Pluripotent Stem Cells", Investigative Opthalmology & Visual Science, vol. 57, No. 15, Dec. 21, 2016, pp. 6878-6884.
Zhong et al., "Generation of three-dimensional retinal tissue with functional photoreceptors from human iPSCs", Nature Communications, 5:4047, (2014).
Office Action issued in Japanese Application No. 2020-557896, dated May 2, 2023, and English translation thereof.
Zhu et al., "Generation of transplantable retinal photoreceptors from a current good manufacturing practice-manufactured human induced pluripotent stem cell line," *Stem Cells Translational Medicine*, 7:210-219, 2018.
Office Action and Search Report issued in Chinese Application No. 201980035975.9, mailed Feb. 8, 2024, and English translation thereof.
Ren et al., "Effects of Cdk5 inhibitor roscovitine on retinal degeneration in Royal College of Surgeons rat," Chin J Ocul Fundus Dis., 31(3):263-267, 2015, Chinese with English abstract.
Xu et al., "Research progress on differentiation from induced pluripotent stem cells into neural retinal cells," Rec Adv Ophtalmol., 36(9):885-888, 2016, Chinese with English abstract.

* cited by examiner

FIG. 10D-3

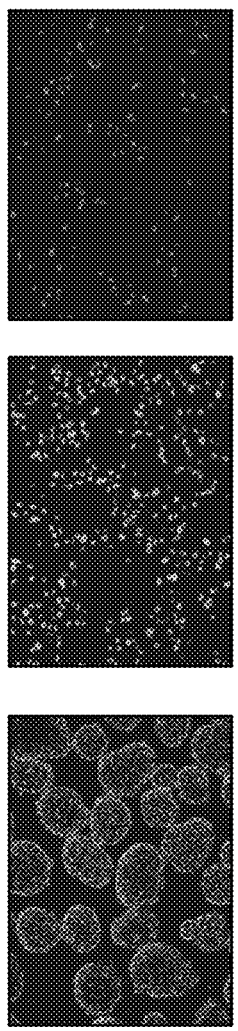
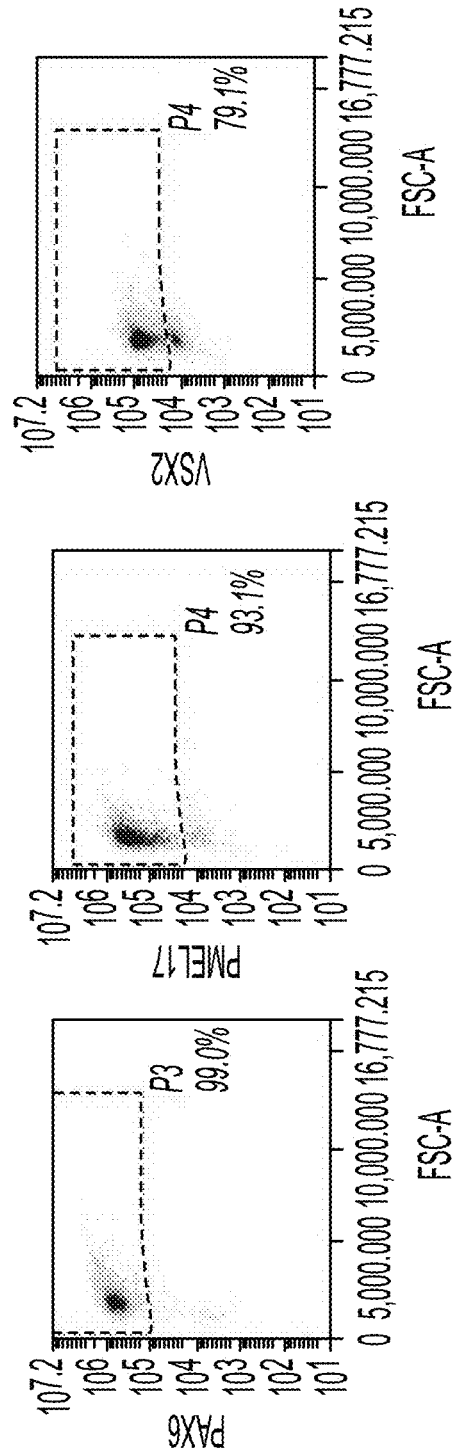
FIG. 14A
FIG. 14B
FIG. 14C

| Enrichment markers | Recoverin | Pax6 | Onecut1 | Ki67 | Chx10 |
|---|---|---|---|---|---|
| Pre-MACS | 65.70% | 29.97% | 14.36% | 0.04% | 0.68% |
| CD111-enriched | 88.29% | 7.07% | 5.87% | 0.00% | 0.26% |
| CD230-enriched | 81.80% | 12.67% | 9.67% | 0.03% | 0.18% |
| CD344-enriched | 85.53% | 8.12% | 5.92% | 0.03% | 0.14% |
| CD111 eluted | 44.53% | 55.50% | 28.16% | 0.02% | 0.94% |
| CD230 eluted | 59.56% | 39.36% | 20.54% | 0.02% | 0.79% |
| CD344 eluted | 69.84% | 30.58% | 17.14% | 0.06% | 0.53% |

| Enrichment markers | Recoverin | Pax6 | Onecut1 | Ki67 |
|---|---|---|---|---|
| Pre-MACS | 78.97% | 17.55% | | |
| CD111-enriched | 90.80% | 4.49% | 1.27% | 0.00% |
| CD230-enriched | 90.64% | 4.00% | 1.40% | 0.00% |
| CD344-enriched | 94.40% | 2.58% | 0.97% | 0.00% |
| CD111 eluted | 62.54% | 31.60% | 12.86% | 0.02% |
| CD230 eluted | 58.62% | 34.05% | 12.49% | 0.00% |
| CD344 eluted | 78.99% | 14.84% | 5.44% | 0.00% |

| Enrichment markers | Recoverin | Pax6 | Ki67 | Chx10 |
|---|---|---|---|---|
| Pre-MACS | 72.38% | 18.49% | 0.02% | 30.55% |
| CD111-enriched | 66.48% | 10.73% | 0.05% | 39.21% |
| CD230-enriched | 75.66% | 7.23% | 0.04% | 32.94% |
| CD344-enriched | 84.80% | 2.80% | NA | 13.83% |
| CD111 eluted | 39.95% | 55.22% | 0.04% | 7.96% |
| CD230 eluted | 30.58% | 55.26% | 0.02% | 27.37% |
| CD344 eluted | 56.06% | 22.42% | 0.04% | 34.90% |

| Enrichment markers | Recoverin | Pax6 | Ki67 | Chx10 |
|---|---|---|---|---|
| Pre-MACS | 19.10% | 73.20% | 39.10% | 8.00% |
| CD133-enriched* | 63.70% | 37.40% | 11.90% | NA |
| CD133 eluted* | 70.00% | 22.90% | 3.00% | 3.00% |

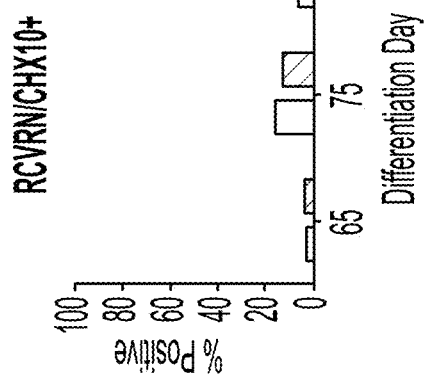
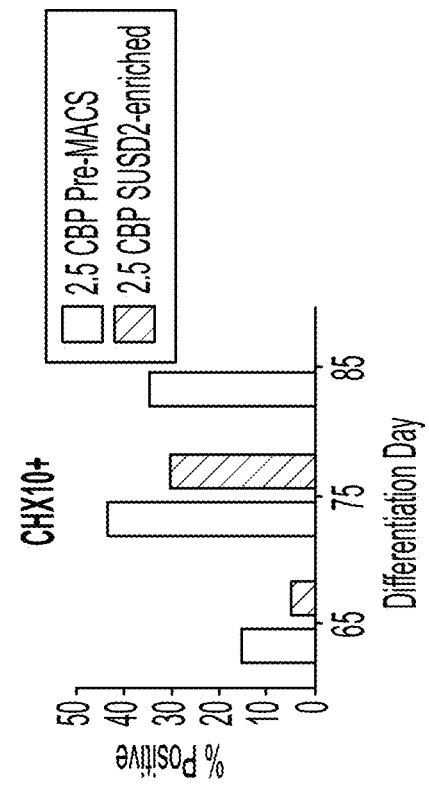
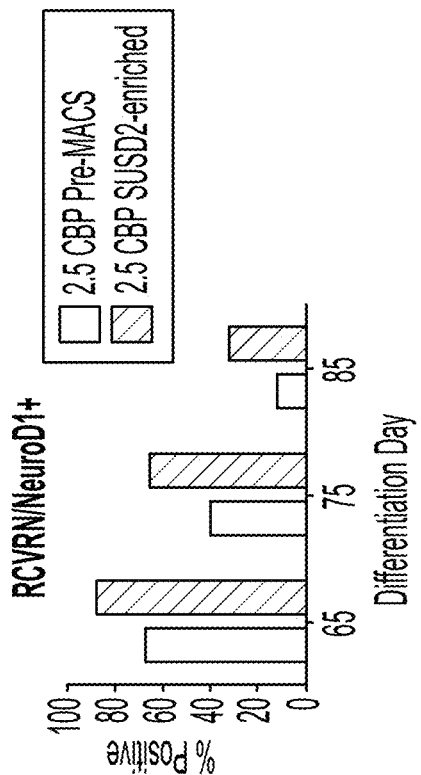
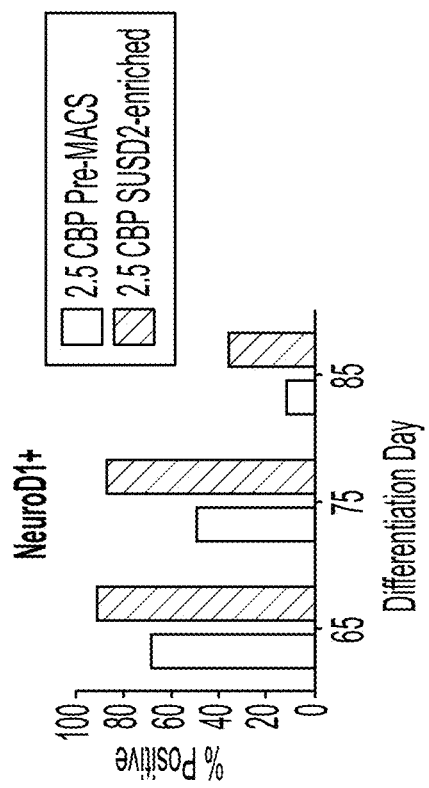
FIG. 34A
FIG. 34B
FIG. 34C
FIG. 34D

METHOD FOR DIFFERENTIATION OF OCULAR CELLS AND USE THEREOF

This application is a national phase application under 35 U.S.C. § 371 of International Application No. PCT/US2019/028557, filed Apr. 22, 2019, which claims the benefit of U.S. Provisional Patent Application No. 62/660,899, filed Apr. 20, 2018, which is incorporated herein by reference in their entirety.

BACKGROUND

1. Field

The present disclosure relates generally to the field of stem cell biology. More particularly, it concerns methods of differentiating pluripotent stem cells to various ocular cells, including photoreceptor precursor (PRP) cells.

2. Description of Related Art

The retina is a light-sensitive layer of tissue that lines the inner surface of the eye. Photoreceptor cells, either rods or cones, in the retina are directly sensitive to light and transform chemical light signals into electrical events that trigger nerve impulses. The impaired or complete loss of function of photoreceptor cells is one of the causes of irreversible blindness in retinal diseases, such as inherited retinal degenerations and age-related macular degeneration (AMD). Retinal ganglion cell (RGC) death in glaucoma also results in irreversible loss of vision. Rescuing the degenerated retina is a major challenge and cell replacement is one of the most promising approaches (Pearson et al., 2012).

The production of induced pluripotent stem cells (iPSCs) from adult somatic mouse cells in 2006 provided an important breakthrough for stem cell research, drug development, models of disease, and cellular therapeutics (Takahashi et al., 2006). Human iPSCs can be differentiated to specialized cell types and have the potential for patient-specific, immune-matched cells for regenerative medicine (Yu et al., 2007). The use of human pluripotent stem cells, embryonic stem (ES) cells and iPSCs opens up a new avenue for treating human retinal degenerative diseases.

Human ES (hES) and iPS (hiPS) cells that have the ability to be expanded indefinitely in culture while retaining their pluripotent status could be used as an unlimited source of photoreceptor cells for tissue transplantation (Comyn et al., 2010). A growing body of convergent data demonstrated hES cell neural retina commitment potential after embryoid body formation, and capacity to further differentiate into cells expressing photoreceptor markers (Zhong et al., 2014; Meyer et al., 2009). The different methods previously developed, though real advances, still suffer from drawbacks generally associated with pluripotent stem cell differentiation into highly specialized cell types. These protocols for photoreceptor-directed differentiation of hES or hiPS cells require several steps, addition of several molecules, and are rather inefficient. Current methods for differentiation into the photoreceptor cell lineage require the formation of embryoid bodies and/or require manual selection of retinal cells from culture. Thus, there is a need in the art for efficient and reliable large-scale methods for obtaining substantially pure cultures of certain human neuroepithelial lineage cells, particularly photoreceptor precursor (PRP) cells.

SUMMARY

The present embodiments provide methods and compositions for the production of ocular cells and use thereof. In a first embodiment, there are provided methods for producing a population of neural retinal progenitors (NRPs) comprising obtaining a starting population of human induced pluripotent stem cells (iPSCs); culturing the iPSCs in retinal induction medium (RIM) to initiate differentiation of the cells into anterior neuroectoderm cells; further culturing the cells in a first retinal differentiation medium (RD1) comprising a BMP inhibitor to further differentiate the cells to anterior neuroectoderm cells; inducing retinal differentiation of the anterior neuroectoderm cells by culturing the cells in a second retinal differentiation medium (RD2) essentially free of BMP inhibitors to form retinal progenitor cells (RPCs); and culturing the RPCs in a retinal maturation (RM) medium to produce NRPs. In a further embodiment, there are provided methods for producing a population of NRPs comprising obtaining a starting population of human iPSCs; culturing the cells in RD1 comprising a BMP inhibitor to further differentiate the cells to anterior neuroectoderm cells; inducing retinal differentiation of the anterior neuroectoderm cells by culturing the cells in RD2 essentially free of BMP inhibitors to form RPCs; and culturing the RPCs in RM medium to produce NRPs. In particular aspects, the culturing is further defined as adherent 2-dimensional culture.

In some aspects, the method further comprises culturing the iPSCs in retinal induction medium (RIM) to initiate differentiation of the cells into anterior neuroectoderm cells prior to culturing the cells in RD1. In certain aspects, the method further comprises culturing the population of NRPs as suspension aggregates in medium comprising a γ-secretase inhibitor and a ROCK inhibitor.

In some aspects of the above embodiments, the methods further comprise culturing the NRPs in FDSC medium comprising a γ-secretase inhibitor and FGF for a period of time sufficient to produce a population of NRPs.

In certain aspects, the RIM comprises a BMP inhibitor, a TGFβ inhibitor, and/or IGF-1. In certain aspects, the RIM comprises a BMP inhibitor, a TGFβ inhibitor, a Wnt inhibitor, and/or IGF-1. In particular aspects, the RIM is essentially free of activin A. In particular aspects, the RIM is essentially free of a Wnt inhibitor, such as CKI-7. In some aspects, culturing the iPSCs in RIM is for 1-3 days, such as 1, 2, or 3 days.

In some aspects, the RD1 medium further comprises a TGFβ inhibitor, a Wnt inhibitor, IGF-1, and a MEK inhibitor. In certain aspects, the RD1 medium further comprises a TGFβ inhibitor, a Wnt inhibitor, IGF-1, and a MEK inhibitor. In certain aspects, the RD1 media does not comprise CKI-7. In some aspects, the culturing in RD1 is for 1-3 days, such as 1, 2, or 3 days.

In some aspects, the RD2 medium comprises a TGFβ inhibitor, a Wnt inhibitor, IGF-1, and a MEK inhibitor. In certain aspects, an increase in VSX2 expression of the anterior neuroectoderm cells is measured for differentiation potential. In particular aspects, the RD2 medium is essentially free of LDN193189. In some aspects, culturing in RD2 is for 5-9 days, such as 5, 6, 7, 8, or 9 days. In certain aspects, at least 90%, 91%, 92%, 93%, 94%, 95%, 96%, 97%, 98%, 99% or 100% of the cells after culturing of in RD2 express PMEL17. In certain aspects, at least 30%, 31%, 32%, 33%, 34%, 35%, 36%, 37%, 38%, 39%, 40%, 45%, 50%, 55%, 60%, 70%, 80%, 90%, 95%, or 100% of the cells after culturing in RD2 express VSX2. In particular aspects, the RPCs express PAX6, MITF, and/or PMEL. In some aspects, the RPCs do not express or have essentially no expression of TRYP1, CRALBP, and/or BEST1.

In some aspects, the culturing from obtaining iPSCs to culturing in RM is further defined as adherent 2-dimensional culture. In some aspects, the culturing from obtaining iPSCs to culturing in RM is essentially free of aggregates.

In some aspects, the RM media comprises nicotinamide and ascorbic acid. In certain aspects, the RM medium further comprises FGF and a TGFβ inhibitor. In some aspects, the RM medium further comprises FGF, SB431542, CKI-7, and IGF-1. In some aspects, the RM medium further comprises a γ-secretase inhibitor. In certain aspects, the culturing in RM medium to produce NRPs is for 3-7 days. In some aspects, the NRPs express PAX6 and VSX2. In certain aspects, at least 70%, 71%, 72%, 73%, 74%, 75%, 76%, 77%, 78%, 79%, 80%, 85%, 90%, 95%, or 100% of the cells after culturing in RM medium to produce NRPs express PAX6 and VSX2. In particular aspects, the RPCs express PAX6, MITF, and/or PMEL.

In another embodiment, there are provided methods for producing a population of photoreceptor precursor cells (PRPs) comprising obtaining a starting population of NRPs according to the embodiments; and further culturing the NRPs in photoreceptor precursor induction medium (FDSC) medium comprising a γ-secretase inhibitor and FGF for a period of time sufficient to produce a population of PRPs. In some aspects, the culturing is further defined as adherent 2-dimensional culture.

In some aspects, the culturing of the NRPs in FDSC medium comprising a γ-secretase inhibitor and FGF for a period of time sufficient to produce a population of PRPs is for 10-20, 20-30, 30-40, or 40-50 days, such as 11, 12, 13, 14, 15, 16, 17, 18, or 19 days or more. the FDSC further comprises a TGFβ inhibitor and WNT inhibitor. In some aspects, the RM medium further comprises FGF and a TGFβ inhibitor.

In some aspects, the method to produce PRPs further comprises maturing the population of PRPs as suspension aggregates in RM medium or a photoreceptor maturation (PM) medium comprising nicotinamide, thereby producing a population of mature PRP aggregates. In some aspects, maturing is for 6-10 days, such as 6, 7, 8, 9, or 10 days. In additional aspects, the method further comprises cryopreserving the mature PRP aggregates. In some aspects, the PM medium further comprises a γ-secretase inhibitor.

In certain aspects, the method to produce PRPs further comprises dissociating the mature PRP aggregates into essentially single cells in PM medium. In some aspects, the method comprises cryopreserving the mature PRPs as single cells.

In some aspects, the PRPs are cultured as adherent cells in PM medium for 5-12 days, such as 5, 6, 7, 8, 9, 10, 11, or 12 days. In certain aspects, the PM medium further comprises a γ-secretase inhibitor. In certain aspects, the dissociated cells are re-aggregated. In some aspects, the PM medium further comprises a CDK inhibitor. In particular aspects, at least 75%, 76%, 77%, 78%, 79%, 80%, 81%, 82%, 83%, 84%, 85%, 90%, 95%, or 100% of the cells express Recoverin (RCVRN).

In some aspects, the method further comprises purifying the PRPs. In certain aspects, purifying comprises selecting cells that are positive for CD171, thereby providing a purified PRP cell population. In some aspects, purifying comprises selecting cells that are positive for CD171 and/or SUSD2, thereby providing a purified PRP cell population. In particular aspects, purifying comprises selecting cells that are positive for CD171, SUSD2, CD56 (NCAM), CD57 (LAMP-3), CD81, CD111 (Nectin 1), CD133, CD147, CD184 (CXCR4), CD200, CD230, CD276, CD298, CD344 (Frizzled), PSA-NCAM, and/or PTK7, thereby providing a purified PRP cell population. In specific aspects, purifying comprises selecting cells that are positive for CD111, CD133, CD230, and/or CD344, thereby providing a purified PRP cell population. In some aspects, purifying comprises selecting cells that are positive for CD344, thereby providing a purified PRP cell population. In some aspects, purifying is performed at Day 65 or Day 75. In certain aspects, purifying comprises depletion of cells positive for two or more of the markers selected from the group consisting of CD9, CD49f, CD340, podoplanin, CD29, CD63, and CD298.

In some aspects, at least 90%, 91%, 92%, 93%, 94%, 95%, 96%, 97%, 98%, 99%, or 100% of the cells in the purified PRP cell population express Class III β-tubulin (TUBB3). In certain aspects, at least 50%, 51%, 52%, 53%, 54%, 55%, 56%, 57%, 58%, 59%, 60%, 65%, 70%, 75%, 80%, 85%, 90%, 95%, or 100% of the cells in the purified PRP cell population express RCVRN. In some aspects, at least 70%, 71%, 72%, 73%, 74%, 75%, 76%, 77%, 78%, 79%, 80%, 85%, 90%, 95%, or 100% of the cells in the purified PRP cell population express RCVRN. In some aspects, the PRPs express one or more markers selected from the group consisting of OTX2, CRX, BLIMP1, NEUROD1, RCVRN, TUBB3 and CD171/L1CAM. In certain aspects, the PRPs do not express or have essentially no expression of TRYP1, CRALBP, BEST1, Ki67, MITF, and/or PMEL17. In some aspects, the cells have low or essentially no expression of PAX6, CHX10 (also referred to herein as VSX2; both terms are used interchangeably herein) and/or Onecut1. In particular aspects, less than 15%, 10%, or 5% (e.g., less than 4%, 3%, 2%, or 1%) of the cells in the purified PRP population express PAX6.

A further embodiment provides methods for producing a population of PRPs comprising obtaining a starting population of NRPs according to the embodiments; and further culturing the NRPs in PRP maturation medium (PM) comprising a cyclin-dependent kinase inhibitor for a period of time sufficient to produce a population of PRPs.

In some aspects, at least 70% (e.g., 71%, 72%, 73%, 74%, 75%, 76%, 77%, 78%, 79%, 80%, 85%, 90%, 95%, or 100%) of the cells are positive for PAX6 and CHX10 prior to culturing in PM medium. In certain aspects, the NRPs are cultured as aggregates in the presence of a γ-secretase inhibitor and a ROCK inhibitor. In some aspects, the PM further comprises a γ-secretase inhibitor. In particular aspects, the PM further comprises a MEK inhibitor.

In additional aspects, the method further comprising dissociating the PRPs into essentially single cells in PM medium. In some aspects, the PRPs are cultured as adherent cells in PM medium.

In some aspects, the method further comprises enriching for PRPs by selecting for cells that are positive for CD171, SUSD2, CD56 (NCAM), CD57 (LAMP-3), CD81, CD111 (Nectin 1), CD133, CD147, CD184 (CXCR4), CD200, CD230, CD276, CD298, CD344 (Frizzled), PSA-NCAM, and/or PTK7, and/or removing cells that are positive for CD9, CD49f, CD340, podoplanin CD29, CD63, and/or CD298. In some aspects, at least 90% (e.g., 91%, 92%, 93%, 94%, 95%, 96%, 97%, 98%, 99%, or 100%) of the cells are positive for TUBB3 and/or at least 70% (e.g., 71%, 72%, 73%, 74%, 75%, 76%, 77%, 78%, 79%, 80%, 85%, 90%, 95%, or 100%) of the cells are positive for RCVRN.

In yet another embodiment, there are provided methods for producing a population of optic vesicles (OVs) comprising obtaining a starting population of PRPs according to the embodiments; and further culturing the PRPs as suspension aggregates in RM medium or PRP maturation (PM) medium for a period of time sufficient to produce a population of OVs.

In some aspects, the culturing of PRPs as suspension aggregates in RM medium or PRP maturation (PM) medium for a period of time sufficient to produce a population of OVs is for at least 20 days, such as at least, 21, 22, 23, 24, 25, 26, 27, 28, 29, 30, 35, 40, 45, 50 or more days. In some aspects, the RM medium further comprises a γ-secretase inhibitor. In certain aspects, the RM medium further comprises FGF and SB431542. In some aspects, at least 50%, 51%, 52%, 53%, 54%, 55%, 56%, 57%, 58%, 59%, 60%, 65%, 70%, 75%, 80%, 85%, 90%, 95%, or 100% of the cells in the population of OVs express VSX2. In some aspects, at least 10%, 11%, 12%, 13%, 14%, 15%, 16%, 17%, 18%, 19%, 20%, 25%, 30%, 40%, 50%, 60% or higher of the cells in the population of OVs express RCVRN. In some aspects, the OVs express Gamma-synuclein (SNCG), Opsin, RCVRN, and Rhodopsin. In certain aspects, the FDSC further comprises a TGFβ inhibitor and a Wnt inhibitor.

In some aspects, the culturing of NRPs in RM medium comprising aγ-secretase inhibitor and FGF for a period of time sufficient to produce a population of PRPs is for 10-20 days, such as 11, 12, 13, 14, 15, 16, 17, 18, 19, 20 or more days. In some aspects, at least 65%, 70%, 75%, 80%, 85%, 90%, 95% or higher of the cells in the population of PRPs express TUBB3. In some aspects, at least 30%, 31%, 32%, 33%, 34%, 35%, 36%, 37%, 38%, 39%, 40%, 45%, 50%, 55%, 60%, 70%, 80%, 90%, 95%, or 100% of the cells in the population of PRPs express RCVRN.

In additional aspects, the methods further comprise culturing the population of NRPs as suspension aggregates in medium comprising a γ-secretase inhibitor and a ROCK inhibitor. In some aspects, the medium further comprises ascorbic acid and nicotinamide. In certain aspects, at least 75%, 76%, 77%, 78%, 79%, 80%, 85%, 90%, 95%, or 100% of the cells in the population of NRPs express VSX2.

In another embodiments, there are provided pharmaceutical compositions comprising the PRPs produced according to the embodiments, the OVs produced according to the embodiments, or the NRPs produced according to the embodiments, and a pharmaceutically acceptable carrier.

A further embodiment provides methods of treating injury or degeneration of retinal neurons in a subject comprising administering an effective amount of the pharmaceutical composition of the embodiments (e.g., PRPs, OVs, or NRPs produced herein) to an eye of the subject. In some aspects, the retinal neurons are photoreceptors.

The ocular cells, such as PRP cells, produced by the methods herein may be used in any methods and applications currently known in the art for photoreceptor cells. For example, a method of assessing a compound may be provided, comprising assaying a pharmacological or toxicological property of the compound on the photoreceptor cell. There may also be provided a method of assessing a compound for an effect on a PRP cell, comprising: a) contacting the PRP cells provided herein with the compound; and b) assaying an effect of the compound on the PRP cells.

In certain aspects of the above embodiments, the RIM comprises LDN193189, SB431542, CKI-7, and IGF-1. In some aspects, the RD1 medium further comprises a TGFβ inhibitor, a Wnt inhibitor, IGF-1, and a MEK inhibitor. In certain aspects, the RD2 medium comprises a TGFβ inhibitor, a Wnt inhibitor, IGF-1, and a MEK inhibitor. In some aspects, the BMP inhibitor is LDN193189. In some aspects, the TGFβ is further defined as a type I receptor activin receptor-like kinase (ALK5) inhibitor. In certain aspects, the TGFβ inhibitor is SB431542, 6SB525334, SB-505124, Lefty, A 83-01, D 4476, GW 788388, LY 364847, R 268712, or RepSox. In some aspects, the WNT inhibitor is CKI-7, IWP2, IWP4, PNU 74654 XAV939, TAK 715, DKK1, or SFRP1. In particular aspects, the MEK inhibitor is PD0325901. In some aspects, RD2 medium comprises SB431542, CKI-7, IGF-1, and PD0325901. In specific aspects, the RM medium further comprises FGF, SB431542, CKI-7, and IGF-1. In some aspects, the γ-secretase inhibitor is DAPT, Begacestat, Compound W, JLK6, L-685,485, Flurizan, DBZ, MRK560, PF3084014 hydrobromide, or BMS299897. In some aspects, the cycling dependent kinase (CDK) inhibitor is a CDK4/6 inhibitor, such as PD0332991 (palbociclib).

In another embodiment, there is provided a composition comprising a NRP population, wherein at least 90% (e.g., 91%, 92%, 93%, 94%, 95%, 96%, 97%, 98%, 99% or 100%) of the cells in the NRP population express PAX6, at least 90% (e.g., 91%, 92%, 93%, 94%, 95%, 96%, 97%, 98%, 99% or 100%) of the cells in the NRP population express PMEL17, and/or at least 70%, 71%, 72%, 73%, 74%, 75%, 76%, 77%, 78%, 79%, 80%, 85%, 90%, 95%, or 100% of the cells in the NRP population express VSX2. In some aspects, at least 95% of the cells in the NRP population express PAX6, at least 90% (e.g., 91%, 92%, 93%, 94%, 95%, 96%, 97%, 98%, 99% or 100%) of the cells in the NRP population express PMEL17, and/or at least 75% of the cells in the NRP population express VSX2. In certain aspects, at least 95% of the cells in the NRP population express PAX6, at least 90% (e.g., 91%, 92%, 93%, 94%, 95%, 96%, 97%, 98%, 99% or 100%) of the cells in the NRP population express PMEL17, and at least 75% of the cells in the NRP population express VSX2. In some aspects, the cells in the NRP population further express Ki67.

In another embodiment, there is provided a composition comprising a PRP population, wherein at least 90% (e.g., 91%, 92%, 93%, 94%, 95%, 96%, 97%, 98%, 99% or 100%) of the cells in the PRP population express TUBB3, at least 50%, 51%, 52%, 53%, 54%, 55%, 56%, 57%, 58%, 59%, 60%, 65%, 70%, 75%, 80%, 85%, 90%, 95%, or 100% of the cells in the PRP cell population express RCVRN, and/or less than 15% of the cells in the PRP population express PAX6. In some aspects, at least 70%, 71%, 72%, 73%, 74%, 75%, 76%, 77%, 78%, 79%, 80%, 85%, 90%, 95%, or 100% of the cells in the PRP population express RCVRN. In certain aspects, less than 10% or 5% of the cells in the PRP population express PAX6. In some aspects, at least 90% of the cells in the PRP population express TUBB3, at least 50%, 51%, 52%, 53%, 54%, 55%, 56%, 57%, 58%, 59%, 60%, 65%, 70%, 75%, 80%, 85%, 90%, 95%, or 100% of the cells in the PRP cell population express RCVRN, and less than 15% of the cells in the PRP population express PAX6. In some aspects, at least 90% of the cells in the PRP population express TUBB3, at least 70%, 71%, 72%, 73%, 74%, 75%, 76%, 77%, 78%, 79%, 80%, 85%, 90%, 95%, or 100% of the cells in the PRP cell population express RCVRN, and/or less than 5% of the cells in the PRP population express PAX6. In certain aspects, the PRPs express one or more markers selected from the group consisting of OTX2, IRBP, SUSD2, CRX, BLIMP1, NEUROD1, RCVRN, TUBB3 and CD171/L1CAM. In some aspects, the PRPs do not express or have essentially no expression of TRYP1, CRALBP, BEST1, Ki67, MITF, and/or PMEL17.

A further embodiment provides a composition comprising a population of OVs, wherein at least 50%, 51%, 52%, 53%, 54%, 55%, 56%, 57%, 58%, 59%, 60%, 65%, 70%, 75%, 80%, 85%, 90%, 95%, or 100% of the cells express VSX2 and/or at least 20% of the cells express RCVRN. In some aspects, at least 65% of the cells express VSX2 and/or at least 30%, 31%, 32%, 33%, 34%, 35%, 36%, 37%, 38%, 39%, 40%, 45%, 50%, 55%, 60%, 70%, 80%, 90%, 95%, or 100% of the cells express RCVRN. In certain aspects, at least 65% of the cells express VSX2 and at least 30% of the cells express RCVRN.

Another embodiment provides a method for providing an enriched population of PRP cells comprising obtaining a starting cell population comprising PRP cells; and enriching said starting cell population for PRP cells by selecting for cells that are positive for CD171, SUSD2, CD56 (NCAM), CD57 (LAMP-3), CD81, CD111 (Nectin 1), CD133, CD147, CD184 (CXCR4), CD200, CD230, CD276, CD298, CD344 (Frizzled), PSA-NCAM, and/or PTK7, and/or removing therefrom cells that are positive for CD9, CD49f, CD340, podoplanin, CD29, CD63, and/or CD298, thereby providing a PRP-enriched cell population that is enriched for PRP cells as compared to the starting cell population. In some aspects, the method further comprises determining a level of enrichment of the PRP cells in said PRP-enriched population. In some aspects, the level of enrichment is determined through the use of a cell marker selected from the group consisting of TUBB3, RCVRN, OTX2, IRBP, SUSD2, CRX, BLIMP1, NEUROD1, and CD171/L1CAM. In certain aspects, the PRP-enriched cell population is enriched for PRP cells as compared to the starting cell population as determined by RCVRN sorting. In some aspects, the PRP-enriched population is at least 50%, 51%, 52%, 53%, 54%, 55%, 56%, 57%, 58%, 59%, 60%, 65%, 70%, 75%, 80%, 85%, 90%, 95%, or 100% PRP cells.

In certain aspects, the PRP-enriched population is at least 70%, 71%, 72%, 73%, 74%, 75%, 76%, 77%, 78%, 79%, 80%, 85%, 90%, 95%, or 100% PRP cells. In some aspects, the PRP-enriched population is essentially pure PRP cells. In particular aspects, the PRP cells are human PRP cells. In some aspects, the starting cell population is prepared from iPSCs. In some aspects, selecting and/or removing is performed by magnetic bead-based sorting or fluorescence-based sorting. In some aspects, the method comprises selecting for cells that are positive for CD171, SUSD2, CD111, CD133, CD230, and/or CD344.

Another embodiment provides a method for performing quality control during the production of an NRP cell product comprising detecting the expression of cell markers selected from the group consisting of PAX6, CHX10 (VSX2), Ki67, and PMEL. In some aspects, at least 70%, 71%, 72%, 73%, 74%, 75%, 76%, 77%, 78%, 79%, 80%, 85%, 90%, 95%, or 100% of the cells are positive for PAX6, CHX10 (VSX2), Ki67, and PMEL. In certain aspects, at least 90% of the cells are positive for PAX6, CHX10 (VSX2), Ki67, and PMEL.

In a further embodiment, there is provided a method for performing quality control during the production of a PRP cell product comprising detecting the expression of off-target cell markers selected from the group consisting of PAX6, ONECUT1, HNCHF6, CHX10, and Ki67. In some aspects, the off-target cells are positive for PAX6 and ISL1. In some aspects, a PRP cell product passing quality control comprises less than 10% or 5% PAX6-positive cells. In certain aspects, a PRP cell product passing quality control comprises less than 10% PAX6-positive cells, less than 0.05% Ki67-positive cells, less than 30%, 31%, 32%, 33%, 34%, 35%, 36%, 37%, 38%, 39%, 40%, 45%, 50%, 55%, 60%, 70%, 80%, 90%, 95%, or 100% CHX10-positive cells, and/or less than 2% ONECUT1-positive cells. In some aspects, a PRP cell product passing quality control comprises less than 5% PAX6-positive cells, less than 0.04% Ki67-positive cells, less than 15% CHX10-positive cells, and/or less than 1% ONECUT1-positive cells. In certain aspects, a PRP cell product passing quality control comprises less than 5% PAX6-positive cells, less than 0.04% Ki67-positive cells, less than 15% CHX10-positive cells, and less than 1% ONECUT1-positive cells.

A further embodiment provides a method for performing quality control during the production of an OV cell product comprising detecting the expression of one or more cell markers selected from the group consisting of RCVRN, CHX10, PAX6, and Ki67. In certain aspects, the cells markers are RCVRN and CHX10. In particular aspects, at least 60% of the cells in the OV cell product are positive for RCVRN and at least 30%, 31%, 32%, 33%, 34%, 35%, 36%, 37%, 38%, 39%, 40%, 45%, 50%, 55%, 60%, 70%, 80%, 90%, 95%, or 100% of the cells in the OV cell product are positive for CHX10. In some aspects, the cell markers are PAX6 and Ki67. In some aspects, the method further comprises detecting the absence of TYRP1. In some aspects, the method further comprises detecting the expression of one or more markers selected from the group consisting of MITF, CRALBP, BEST1, OTX2, CRX, BLIMP1, NEUROD1, TUBB3, ONECUT1, and CD171/L1CAM.

Other objects, features and advantages of the present disclosure will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3C) Pre- and post-MACS flow cytometry analysis summary for 2-D PRP differentiations (n=5).

(FIG. 4A) Image of day 2 post-thaw 2-D PRP aggregates (10× objective). (FIG. 4B) Immunofluorescence staining of day 1 post-thaw 2-D PRPs for TUBB3 and RCVRN (20× objective). (FIG. 4C) Immunofluorescence staining of day 1 post-thaw 2-D PRPs for CRX and RCVRN (20× objective).

(FIG. 4D) Single cell gene expression analysis of day 2 post-thaw 2-D PRP aggregates.

(FIG. 8A) Morphology of late-stage plated PRP in PM medium with or without the addition of PD0332991 or Activin A. (FIG. 8B) Flow cytometry analysis of late-stage plated C-2 PRP in PM medium with or without the addition of PD0332991 or Activin A.

(FIG. 10A) Image of day 2 post-thaw Hybrid PRP aggregates (10× objective). (FIG. 10B) Immunofluorescence staining of day 1 post-thaw Hybrid PRP for TUBB3 and RCVRN (20× objective). (FIG. 10C) Immunofluorescence staining of day 1 post-thaw Hybrid PRP for CRX and RCVRN (20× objective). (FIG. 10D). Single cell gene expression analysis of day 2 post-thaw Hybrid PRP aggregates.

(FIG. 12A) Image of day 68 differentiating Hybrid OV. (FIG. 12B) Immunofluorescence staining time course of differentiating Hybrid OV for VSX2 and RCVRN. (FIG. 12C) Immunofluorescence staining of late-stage Hybrid OV for Gamma-synuclein (SNCG; retinal ganglion cell marker), RCVRN (PRP and photoreceptor marker), Green-sensitive Opsin (OPN1MW; cone marker), cone-arrestin (ARR3; cone marker) and Rhodopsin (RHO; rod marker). (FIG. 12D) Flow cytometry time course analysis of differentiating Hybrid OV for VSX2 and RCVRN.

FIGS. 14A-14C: 2-D NRP Characterization. (FIG. 14A) Image of day 2 post-thaw NRP aggregates. (FIG. 14B) Immunofluorescence staining of day 1 post-thaw adherent NRP for PAX6 (left) and VSX2 (right). (FIG. 14C) Flow cytometry analysis of day 2 post-thaw NRP for PAX6, PMEL17 and VSX2.

FIGS. 24A-24B: (FIG. 24A) Flow cytometry analysis of Ki67 and CHX10 expression with or without CKI-7 at Day 15 and Day 25 of PRP differentiation. *Using conjugated CHX10 shifted the plot (higher) but in this case reduced the expression level; it may be possible that the antibody did not label maximum epitopes due to steric hindrance. (FIG. 24B) Percent expression of Ki67 and CHX10 with or without CKI-7 at Day 15 and Day 25 of PRP differentiation.

FIGS. 25A-25B: (FIG. 25A) Flow cytometry analysis of TYRP1 and PMEL expression with or without CKI-7 at Day 15 and Day 25 of PRP differentiation. (FIG. 25B) Percent expression of TYRP1 and PMEL with or without CKI-7 at Day 15 and Day 25 of PRP differentiation.

(FIG. 31A) SUSD2-enriched RCVRN-positive population. (FIG. 31B) CD171-enriched RCVRN-positive population.

FIGS. 34A-34E: At D65, the height pre-MACS SUSD2 and pre- and post-MACS recoverin expression, CHX10 expression is at its lowest but significantly increases by D75 and D85 (FIG. 34A). Co-expression of recoverin-CHX10 was <3% at D65, rising and falling at D75 and D85, respectively, suggesting a short-lived bipolar cell population (FIG. 34B). NeuroD1 expression was highest at D65 pre- and post-enrichment compared to D75 and D85 (FIG. 34C) and NeuroD1 co-expression was also greatest at D65 and further enhanced post-SUSD2 enrichment (FIG. 34D). An additional experiment (FIG. 34E) confirmed low CHX10 at D55, and also showed substantial reduction in CHX10 after SUSD2 MACS enrichment at D75.

I. DESCRIPTION OF ILLUSTRATIVE EMBODIMENTS

Figure 1:
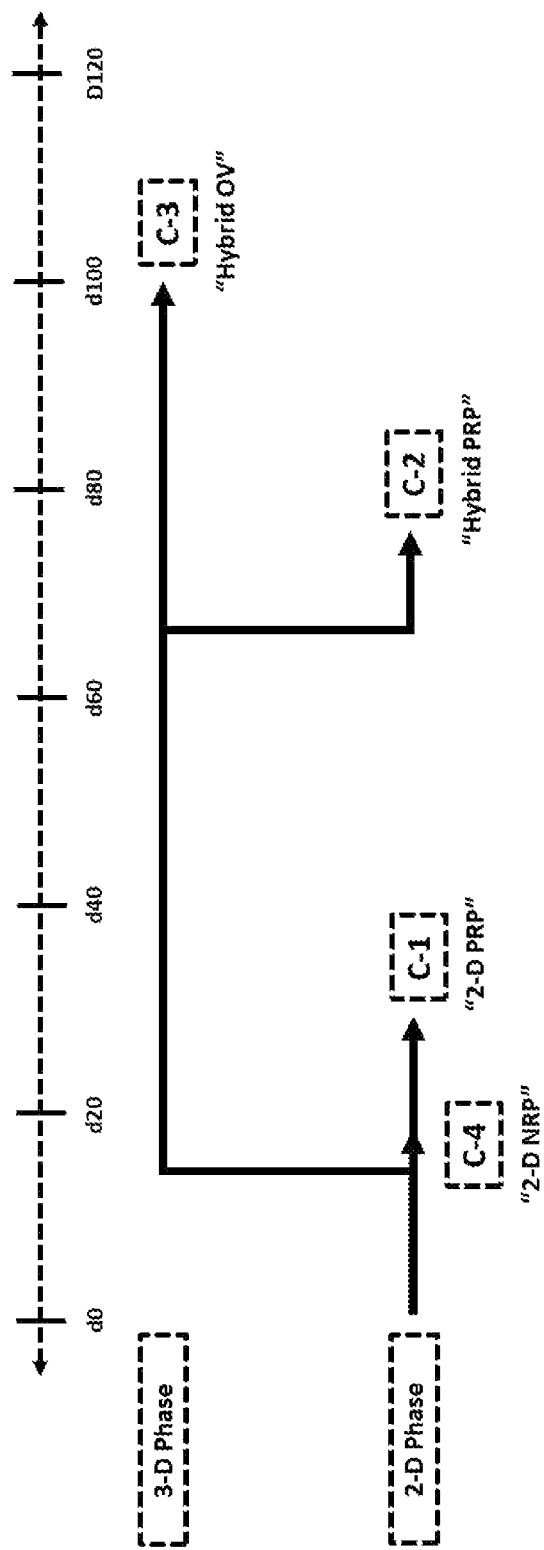
FIG. 1: Candidate Overview. Schematic of iPSC-derived ocular cell differentiation including neural retinal progenitor cells (NRPs), photoreceptor precursor cells (PRPs) and optic vesicles (OVs). Candidate 1 (C-1) represents PRP differentiated under adherent 2-dimensional (2-D) conditions (2-D PRP). Candidate 2 (C-2) represents PRP differentiated under both 2-D and suspension aggregate 3-dimensional (3-D) conditions (Hybrid PRP). Candidate 3 (C-3) represents OVs differentiated under both 2-D and 3-D conditions (Hybrid OV). Candidate 4 (C-4) represents NRPs differentiated under 2-D conditions.
Figure 2:
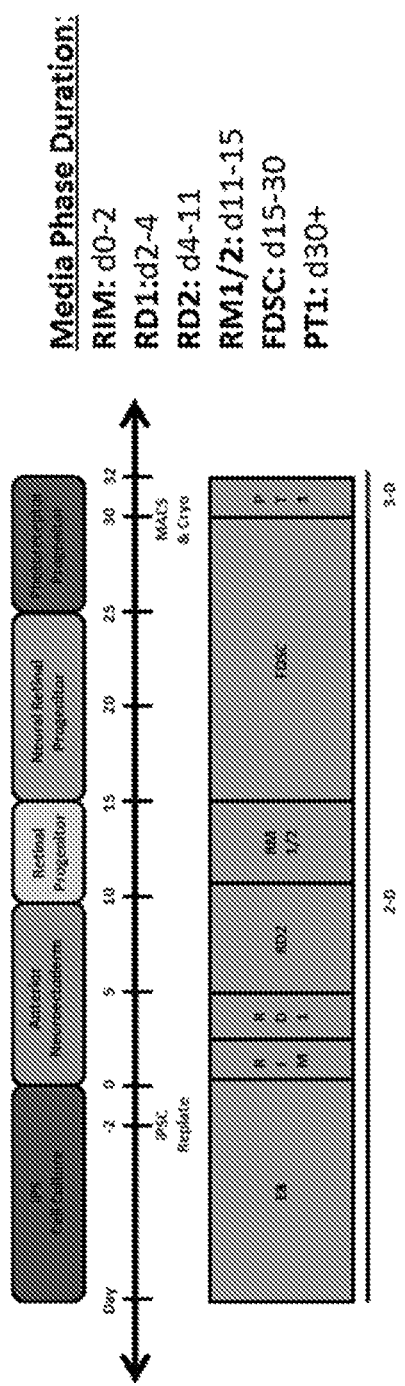
FIG. 2: Schematic of the 2-D PRP differentiation process including media phase duration.
Figure 3A:
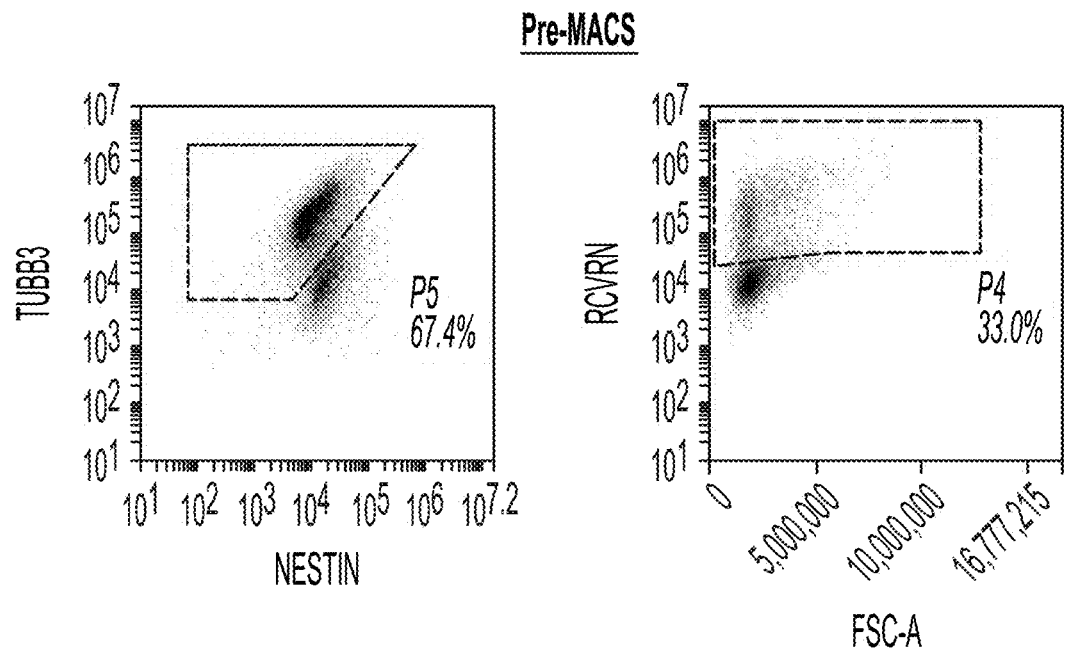
FIGS. 3A-3C: 2-D PRP MACS Enrichment. Flow cytometry analysis of 2-D PRP for βIII-tubulin (TUBB3) and Recoverin (RCVRN) expression both (FIG. 3A) pre- and (FIG. 3B) post-MACS enrichment.
Figure 3B:
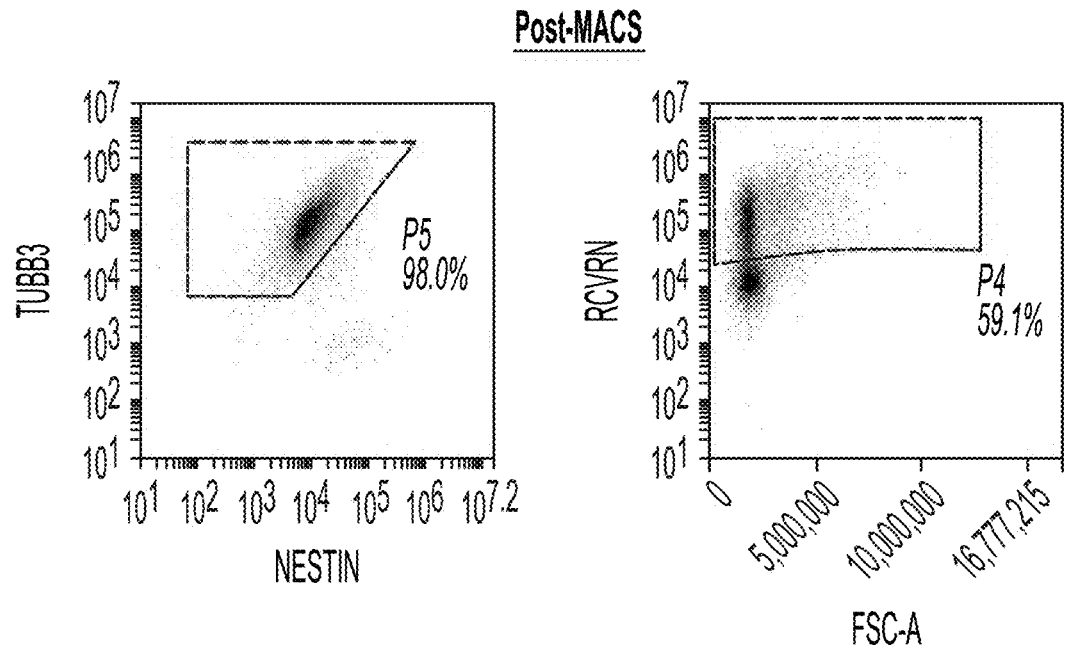
Figure 3C:
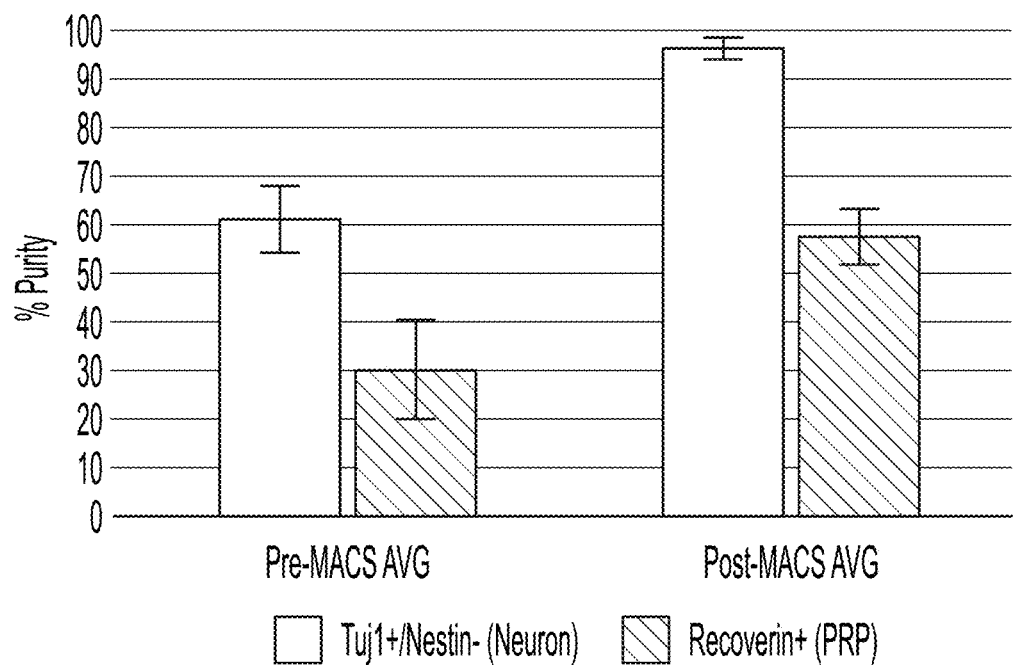

In certain embodiments, the present disclosure provides methods for producing ocular cells, including a photoreceptor precursor (PRP) cell population. PRP cells can be derived from pluripotent stem cells such as ES cells or iPS cells in a defined 2D cell culture without the need for formation of embryoid bodies or selecting colonies of cells. Alternatively, the PRP cells may be derived in a hybrid adherent 2-D and suspension aggregate 3-D culture. Briefly, the PSCs may be differentiated to anterior neuroectoderm cells which are cultured in a retinal differentiation media comprising a BMP inhibitor for a short period and then further cultured in a retinal differentiation media without the BMP inhibitor. Interestingly, the inventors found that the removal of the BMP inhibitor enhances the neural retinal differentiation potential of the anterior neuroectoderm cells. The cells may then be further differentiated into retinal progenitor cells (RPCs) in the presence of nicotinamide and the absence of Activin A to direct the cells toward a photoreceptor lineage instead of other retinal lineages, such as retinal pigment epithelial cells. Finally, the RPCs, may be differentiated in the presence of a TGFβ inhibitor, a WNT inhibitor, basic FGF, and a γ-secretase inhibitor to produce neural retinal progenitor (NRP) cells which may then be differentiated to PRP cells. Thus, the present disclosure provides a highly efficient and reproducible method of differentiating PSCs into PRP cells.

The present disclosure also provides methods for the production of PRP cells or optic vesicles through the combination of a 2D and 3D aggregate culture. The RPCs may be cultured as aggregates in retinal maturation media free of Activin A for a period of time to produce PRP aggregates which may then be dissociated and cultured as a monolayer. Alternatively, the RPCs may be cultured in the retinal maturation media free of Activin A for an extended period of time to produce the PRP aggregates and eventually produce optic vesicles.

Further embodiments of the present disclosure provide a method of purifying the population of PRP cells that are obtained by the above methods. The purification method can comprise positive and/or negative selection. For example, cells which express CD171 may be selected for by cell sorting. Therefore, the purification process yields a PRP-enriched cell population that has a greater percentage of PRP cells than the population obtained after differentiation from the RPCs.

Thus, the present methods are more time- and cost-efficient, and may enable manufacture of PRP-enriched cell populations for therapeutics from a renewable source, stem cells, at a clinical scale. They may be used to uncover mechanisms, new genes, soluble or membrane-bound factors that are important for the development, differentiation, maintenance, survival and function of photoreceptor cells.

The PRP cells and photoreceptor cells provided herein may be used in a variety of in vivo and in vitro methods. For example, the PRP cells may be used in vivo to treat conditions of the retina, including but not limited to macular degeneration and retinitis pigmentosa. The PRP cells and photoreceptor cells may also be used in vitro in screening assays to identify putative therapeutic or prophylactic treatment candidates. Further embodiments and advantages of the present disclosure are described below.

I. DEFINITIONS

The term "purified" does not require absolute purity; rather, it is intended as a relative term. Thus, a purified population of cells is greater than about 90% 91%, 92%, 93%, 94%, 95%, 96%, 97%, 98%, 99% or 100% pure, or, most preferably, essentially free of other cell types.

As used herein, "essentially" or "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein in the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "cell population" is used herein to refer to a group of cells, typically of a common type. The cell population can be derived from a common progenitor or may comprise more than one cell type. An "enriched" cell population refers to a cell population derived from a starting cell population (e.g., an unfractionated, heterogeneous cell population) that contains a greater percentage of a specific cell type than the percentage of that cell type in the starting population. The cell populations may be enriched for one or more cell types and depleted of one or more cell types.

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs".

The term "pluripotent" refers to the property of a cell to differentiate into all other cell types in an organism, with the exception of extraembryonic, or placental, cells. Pluripotent stem cells are capable of differentiating to cell types of all three germ layers (e.g., ectodermal, mesodermal, and endodermal cell types) even after prolonged culture. A pluripotent stem cell is an embryonic stem cell derived from the inner cell mass of a blastocyst. In other embodiments, the pluripotent stem cell is an induced pluripotent stem cell derived by reprogramming somatic cells.

The term "differentiation" refers to the process by which an unspecialized cell becomes a more specialized type with changes in structural and/or functional properties. The mature cell typically has altered cellular structure and tissue-specific proteins.

As used herein, "undifferentiated" refers to cells that display characteristic markers and morphological characteristics of undifferentiated cells that clearly distinguish them from terminally differentiated cells of embryo or adult origin.

"Embryoid bodies (EBs)" are aggregates of pluripotent stem cells that can undergo differentiation into cells of the endoderm, mesoderm, and ectoderm germ layers. The spheroid structures form when pluripotent stem cells are allowed to aggregate under non-adherent culture conditions and thus form EBs in suspension.

An "isolated" cell has been substantially separated or purified from others cells in an organism or culture. Isolated cells can be, for example, at least 99%, at least 98% pure, at least 95% pure or at least 90% pure.

An "embryo" refers to a cellular mass obtained by one or more divisions of a zygote or an activated oocyte with an artificially reprogrammed nucleus.

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs)" are cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

An "allele" refers to one of two or more forms of a gene. Diploid organisms such as humans contain two copies of each chromosome, and thus carry one allele on each.

The term "homozygous" is defined as containing two of the same alleles at a particular locus. The term "heterozygous" refers to as containing two different alleles at a particular locus.

A "haplotype" refers to a combination of alleles at multiple loci along a single chromosome. A haplotype can be based upon a set of single-nucleotide polymorphisms (SNPs) on a single chromosome and/or the alleles in the major histocompatibility complex.

As used herein, the term "haplotype-matched" is defined as the cell (e.g. iPS cell) and the subject being treated share one or more major histocompatibility locus haplotypes.

The haplotype of the subject can be readily determined using assays well known in the art. The haplotype-matched iPS cell can be autologous or allogeneic. The autologous cells which are grown in tissue culture and differentiated to PRP cells inherently are haplotype-matched to the subject.

"Substantially the same HLA type" indicates that the Human Leukocyte Antigen (HLA) type of donor matches with that of a patient to the extent that the transplanted cells, which have been obtained by inducing differentiation of iPSCs derived from the donor's somatic cells, can be engrafted when they are transplanted to the patient.

"Super donors" are referred to herein as individuals that are homozygous for certain MHC class I and II genes. These homozygous individuals can serve as super donors and their cells, including tissues and other materials comprising their cells, can be transplanted in individuals that are either homozygous or heterozygous for that haplotype. The super donor can be homozygous for the HLA-A, HLA-B, HLA-C, HLA-DR, HLA-DP or HLA-DQ locus/loci alleles, respectively.

"Feeder-free" or "feeder-independent" is used herein to refer to a culture supplemented with cytokines and growth factors (e.g., TGFβ, bFGF, LIF) as a replacement for the feeder cell layer. Thus, "feeder-free" or feeder-independent culture systems and media may be used to culture and maintain pluripotent cells in an undifferentiated and proliferative state.

In some cases, feeder-free cultures utilize an animal-based matrix (e.g. MATRIGEL™) or are grown on a substrate such as fibronectin, collagen, or vitronectin. These approaches allow human stem cells to remain in an essentially undifferentiated state without the need for mouse fibroblast "feeder layers."

"Feeder layers" are defined herein as a coating layer of cells such as on the bottom of a culture dish. The feeder cells can release nutrients into the culture medium and provide a surface to which other cells, such as pluripotent stem cells, can attach.

The term "defined" or "fully-defined," when used in relation to a medium, an extracellular matrix, or a culture condition, refers to a medium, an extracellular matrix, or a culture condition in which the chemical composition and amounts of approximately all the components are known. For example, a defined medium does not contain undefined factors such as in fetal bovine serum, bovine serum albumin or human serum albumin. Generally, a defined medium comprises a basal media (e.g., Dulbecco's Modified Eagle's Medium (DMEM), F12, or Roswell Park Memorial Institute Medium (RPMI) 1640, containing amino acids, vitamins, inorganic salts, buffers, antioxidants, and energy sources) which is supplemented with recombinant albumin, chemically defined lipids, and recombinant insulin. An example of a fully defined medium is Essential 8™ medium.

For a medium, extracellular matrix, or culture system used with human cells, the term "Xeno-Free (XF)" refers to a condition in which the materials used are not of non-human animal-origin.

"Pre-confluent" refers to a cell culture in which the proportion of the culture surface which is covered by cells is about 60-80%. Usually, pre-confluent refers to a culture in which about 70% of the culture surface is covered by cells.

The term "retinal progenitor cells", also called "retinal precursor cells" or "RPCs", encompass cells which are competent for generating all cell types of the retina, including neural retina cells, such as rods, cones, photoreceptor precursor cells, as well as cells which can differentiate into RPE.

The term "neural retinal progenitors" or "NRPs" refers to cells which are restricted in their differentiation potential to neural retina cell types.

The terms "photoreceptor precursor cells" and "PRP" cells refer to cells differentiated from embryonic stem cells or induced pluripotent stem cells which can differentiate into photoreceptor cells that expresses the cell marker rhodopsin or any of the three cone opsins, and optionally express the rod or cone cGMP. The photoreceptors may be rod and/or cone photoreceptors.

The term "optic vesicles" or "OVs" refers to cell aggregates or organoids, including PRP cell aggregates, with a morphology comprising optic vesicle structures.

"Retinal pigment epithelium" refers to a layer of pigmented cells between the choroid, a layer filled with blood vessels, and the neural retina.

"Retinal Induction Medium (RIM)" refers herein to a growth media that comprises a WNT pathway inhibitor and a BMP pathway inhibitor and can result in the differentiation of PSCs to retinal lineage cells. The RIM also comprises a TGFβ pathway inhibitor, and may comprise IGF-1 and ascorbic acid.

The "Retinal Differentiation Medium (RD)" is defined herein as a medium that comprises a WNT inhibitor, a TGFβ inhibitor and a MEK inhibitor and differentiates anterior neuroectoderm cells. The RDM may (i.e., RD1) or may not (i.e., RD2) comprise a BMP inhibitor, and may comprise IGF-1 and ascorbic acid.

The "Retinal Maturation Medium (RM)" is defined as a growth medium for the culture of retinal cells comprising Nicotinamide and ascorbic acid. The RM is preferably free of Activin A. The RM may (i.e., RM1) or may not (i.e., RM2) comprise a γ secretase inhibitor, such as DAPT, or a TGFβ inhibitor, such as SB431542, and may comprise IGF-1 and ascorbic acid.

The "PRP Maturation Medium (PM)" is referred to herein as a growth medium for the culture of PRP cells comprising Nicotinamide and a 7 secretase inhibitor, such as DAPT. The PM may (i.e., PM1) or may not (i.e., PM2) contain a CDK inhibitor, such as PD0332991, a TGF-β pathway activator, such as Activin A, or a mitogen, such as retinoic acid.

The "Photoreceptor Precursor Induction Medium (FDSC)" refers to a growth medium which comprises a TGFβ inhibitor, a WNT inhibitor, and a γ-secretase inhibitor. The FDSC may comprise basic FGF and ascorbic acid.

The term "retinal degeneration-related disease" is intended to refer to any disease resulting from innate or postnatal retinal degeneration or abnormalities. Examples of retinal degeneration-related diseases include retinal dysplasia, retinal degeneration, age-related macular degeneration, diabetic retinopathy, retinitis pigmentosa, congenital retinal dystrophy, Leber congenital amaurosis, retinal detachment, glaucoma, optic neuropathy, and trauma.

A "therapeutically effective amount" used herein refers to the amount of a compound that, when administered to a subject for treatment of a disease or condition, is sufficient to affect such treatment.

II. PLURIPOTENT STEM CELLS

A. Embryonic Stem Cells

ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913).

Methods for producing mouse ES cells are well known. In one method, a preimplantation blastocyst from the 129 strain of mice is treated with mouse antiserum to remove the trophectoderm, and the inner cell mass is cultured on a feeder cell layer of chemically-inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated (U.S. Pat. No. 6,833, 269). In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as MATRIGEL™ or laminin in the presence of "conditioned" medium containing basic fibroblast growth factor (Xu et al., 2001).

ES cells can also be derived from other organisms including rhesus monkey and marmoset by previously described methods (Thomson, and Marshall, 1998; Thomson et al., 1995; Thomson and Odorico, 2000), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

B. Induced Pluripotent Stem Cells

The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. Pluripotent stem cells can be maintained in an undifferentiated state and can differentiate into any adult cell type.

With the exception of germ cells, any somatic cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. In one embodiment, the somatic cell is itself a PRP cell, such as a human PRP cell. The PRP cell can be an adult or a fetal PRP cell. iPSCs can be grown under conditions that are known to differentiate human ES cells into specific cell types, and express human ES cell markers including: SSEA-1, SSEA-3, SSEA-4, TRA-1-60, and TRA-1-81.

Somatic cells can be reprogrammed to produce induced pluripotent stem cells (iPSCs) using methods known to one of skill in the art. One of skill in the art can readily produce induced pluripotent stem cells; see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least two, at least three, or at least four, of Klf4, c-Myc, Oct3/4, Sox2, Nanog, and Lin28 are utilized. In other embodiments, Oct3/4, Sox2, c-Myc and Klf4 are utilized.

The cells are treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. As disclosed in published U.S. Patent Application No. 20120196360, exemplary reprogramming factors for the production of iPSCs include (1) Oct3/4, Klf4, Sox2, L-Myc (Sox2 can be replaced with Sox1, Sox3, Sox15, Sox17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV)16 E6; (4) Oct3/4, Klf4, Sox2, L-Myc, TERT, HPV16 E7 (5) Oct3/4, Klf4, Sox2, L-Myc, TERT, HPV16 E6, HPV16 E7; (6) Oct3/4, Klf4, Sox2, L-Myc, TERT, Bmi1; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Esrrb, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HP VI 6 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmi1; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg). In one non-limiting example, Oct3/4, Klf4, Sox2, and c-Myc are utilized. In other embodiments, Oct4, Nanog, and Sox2 are utilized; see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized. Factors like Nanog, Lin28, Klf4, or c-Myc can increase reprogramming efficiency and can be expressed from several different expression vectors. For example, an integrating vector such as the EBV element-based system can be used (U.S. Pat. No. 8,546,140). In a further aspect, reprogramming proteins could be introduced directly into somatic cells by protein transduction. Reprogramming may further comprise contacting the cells with one or more signaling receptors including glycogen synthase kinase 3 (GSK-3) inhibitor, a mitogen-activated protein kinase kinase (MEK) inhibitor, a transforming growth factor beta (TGF-β) receptor inhibitor or signaling inhibitor, leukemia inhibitory factor (LIF), a p53 inhibitor, an NF-kappa B inhibitor, or a combination thereof. Those regulators may include small molecules, inhibitory nucleotides, expression cassettes, or protein factors. It is anticipated that virtually any iPS cells or cell lines may be used.

Mouse and human cDNA sequences of these nuclear reprogramming substances are available with reference to the NCBI accession numbers mentioned in WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF.

Other methods for the culture and maintenance of iPSCs, as would be known to one of skill in the art, may be used.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™ medium (Chen et al., 2011).

In some embodiments, the iPSC can be modified to express exogenous nucleic acids, such as to include an enhancer operably linked to a promoter and a nucleic acid sequence encoding a first marker. Suitable promoters include, but are not limited to, any promoter expressed in photoreceptor cells, such as a rhodopsin kinase promoter. The construct can also include other elements, such as a ribosome binding site for translational initiation (internal ribosomal binding sequences), and a transcription/translation terminator. Generally, it is advantageous to transfect cells with the construct. Suitable vectors for stable transfection include, but are not limited to retroviral vectors, lentiviral vectors and Sendai virus.

In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector.

Markers include, but are not limited to, fluorescence proteins (for example, green fluorescent protein or red fluorescent protein), enzymes (for example, horse radish peroxidase or alkaline phosphatase or firefly/renilla luciferase or nanoluc), or other proteins. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Nucleic acid sequences encoding these markers can be operably linked to the tyrosinase enhancer. In addition, other genes can be included, such as genes that may influence stem cell to PRP differentiation, or photoreceptor function, or physiology, or pathology.

1. MHC Haplotype Matching

Major Histocompatibility Complex (MHC) is the main cause of immune-rejection of allogeneic organ transplants. There are three major class I MHC haplotypes (A, B, and C) and three major MHC class II haplotypes (DR, DP, and DQ). The HLA loci are highly polymorphic and are distributed over 4 Mb on chromosome 6. The ability to haplotype the HLA genes within the region is clinically important since this region is associated with autoimmune and infectious diseases and the compatibility of HLA haplotypes between donor and recipient can influence the clinical outcomes of transplantation. HLAs corresponding to MHC class I present peptides from inside the cell and HLAs corresponding to MHC class II present antigens from outside of the cell to T-lymphocytes. Incompatibility of MHC haplotypes between the graft and the host triggers an immune response against the graft and leads to its rejection. Thus, a patient can be treated with an immunosuppressant to prevent rejection. HLA-matched stem cell lines may overcome the risk of immune rejection.

Because of the importance of HLA in transplantation, the HLA loci are usually typed by serology and the polymerase chain reaction (PCR) for identifying favorable donor-recipient pairs. Serological detection of HLA class I and II antigens can be accomplished using a complement mediated lymphocytotoxicity test with purified T or B lymphocytes. This procedure is predominantly used for matching HLA-A and -B loci. Molecular-based tissue typing can often be more accurate than serologic testing. Low resolution molecular methods such as SSOP (sequence specific oligonucleotide probes) methods, in which PCR products are tested against a series of oligonucleotide probes, can be used to identify HLA antigens, and currently these methods are the most common methods used for Class II-HLA typing. High resolution techniques such as SSP (sequence specific primer) methods which utilize allele specific primers for PCR amplification can identify specific MHC alleles.

MHC compatibility between a donor and a recipient increases significantly if the donor cells are HLA homozygous, i.e. contain identical alleles for each antigen-presenting protein. Most individuals are heterozygous for MHC class I and II genes, but certain individuals are homozygous for these genes. These homozygous individuals can serve as super donors, and grafts generated from their cells can be transplanted in all individuals that are either homozygous or heterozygous for that haplotype. Furthermore, if homozygous donor cells have a haplotype found in high frequency in a population, these cells may have application in transplantation therapies for a large number of individuals.

Accordingly, iPSCs can be produced from somatic cells of the subject to be treated, or another subject with the same or substantially the same HLA type as that of the patient. In one case, the major HLAs (e.g., the three major loci of HLA-A, HLA-B and HLA-DR) of the donor are identical to the major HLAs of the recipient. In some cases, the somatic cell donor may be a super donor; thus, iPSCs derived from a MHC homozygous super donor may be used to generate PRP cells. Thus, the iPSCs derived from a super donor may be transplanted in subjects that are either homozygous or heterozygous for that haplotype. For example, the iPSCs can be homozygous at two HLA alleles such as HLA-A and HLA-B. As such, iPSCs produced from super donors can be used in the methods disclosed herein, to produce PRP cells that can potentially "match" a large number of potential recipients.

2. Episomal Vectors

In certain aspects, reprogramming factors are expressed from expression cassettes comprised in one or more exogenous episomal genetic elements (see U.S. Patent Publication 2010/0003757, incorporated herein by reference). Thus, iPSCs can be essentially free of exogenous genetic elements, such as from retroviral or lentiviral vector elements. These iPSCs are prepared by the use of extra-chromosomally replicating vectors (i.e., episomal vectors), which are vectors capable of replicating episomally to make iPSCs essentially free of exogenous vector or viral elements (see U.S. Pat. No. 8,546,140, incorporated herein by reference; Yu et al., 2009). A number of DNA viruses, such as adenoviruses, Simian vacuolating virus 40 (SV40) or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors. For example, a lymphotrophic herpes virus-based including or Epstein Barr Virus (EBV) as defined above may replicate extra-chromosomally and help deliver reprogramming genes to somatic cells. Useful EBV elements are OriP and EBNA-1, or their variants or functional equivalents. An additional advantage of episomal vectors is that the exogenous elements will be lost with time after being introduced into cells, leading to self-sustained iPSCs essentially free of these elements.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also, other sources of episome-based vectors are contemplated, such as yeast ARS, adenovirus, SV40, or BPV.

C. Somatic Cell Nuclear Transfer

Pluripotent stem cells can be prepared through the method of somatic cell nuclear transfer. Somatic cell nuclear transfer involves the transfer of a donor nucleus into a spindle-free oocyte. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, and then incubated until the blastocyst stage. The inner cell masses of selected blastocysts are then cultured to produce embryonic stem cell lines. The embryonic stem cell lines show normal ES cell morphology, express various ES cell markers, and differentiate into multiple cell types both in vitro and in vivo.

III. PHOTORECEPTOR PRECURSOR CELLS

In some embodiments, neural retinal progenitor (NRP) cells, photoreceptor precursor (PRP) cells, or optic vesicles (OV) are produced in the methods disclosed herein. The cells in the retina that are directly sensitive to light are the photoreceptor cells. Photoreceptors are photosensitive neurons in the outer part of the retina and can be either rods or cones. In the process of phototransduction, the photoreceptor cells convert incident light energy focused by the lens to electric signals which are then sent via the optic nerve to the brain. Vertebrates have two types of photoreceptor cells including cones and rods. Cones are adapted to detect fine detail, central and color vision and function well in bright light. Rods are responsible for peripheral and dim light vision. Neural signals from the rods and cones undergo processing by other neurons of the retina.

PRP cells can express markers such as OTX2, CRX, PRDM1 (BLIMP1), NEUROD1, RCVRN, TUBB3 and L1CAM (CD171). PRP cells express several proteins that can serve as markers for detection by the use of methodologies, such as immunocytochemistry, Western blot analysis, flow cytometry, or enzyme-linked immunoassay (ELISA). For example, one characteristic PRP-marker is RCVRN. PRP cells may not express (at any detectable level) the embryonic stem cells markers OCT-4, NANOG or REX-1. Specifically, expression of these genes is approximately 100-1000 fold lower in PRP cells than in ES cells or iPSC cells, when assessed by quantitative RT-PCR.

PRP cell markers may be detected at the mRNA level, for example, by reverse transcriptase polymerase chain reaction (RT-PCR), Northern blot analysis, or dot-blot hybridization analysis using sequence-specific primers in standard amplification methods using publicly available sequence data (GENBANK®). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, 50-fold or higher above that of a control cell, such as an undifferentiated pluripotent stem cell or other unrelated cell type.

Dysfunction, injury and loss of photoreceptor cells are factors of many eye diseases and disorders including age-related macular degeneration (AMD), hereditary macular degenerations including Best disease, and retinitis pigmentosa. A potential treatment for such diseases is the transplantation of PRP or photoreceptor cells into the retina of those in need of such treatment. It is speculated that the replenishment of PRP or photoreceptor cells by their transplantation may delay, halt or reverse degradation, improve retinal function and prevent blindness stemming from such conditions. However, obtaining PRP or photoreceptor cells directly from human donors and embryos is a challenge.

In some embodiments, methods are provided for producing PRP cells from an essentially single cell suspension of PSCs such as human iPSCs. In some embodiments, the PSCs are cultured to pre-confluency to prevent any cell aggregates. In certain aspects, the PSCs are dissociated by incubation with a cell dissociation solution or enzyme, such as exemplified by Versene, Trypsin, ACCUTASE™ or TRYPLE™. PSCs can also be dissociated into an essentially single cell suspension by pipetting.

In addition, Blebbistatin (e.g., about 2.5 µM) can be added to the medium to increase PSC survival after dissociation into single cells while the cells are not adhered to a culture vessel. A ROCK inhibitor instead of Blebbistatin may alternatively be used to increase PSC survival after dissociation into single cells.

To efficiently differentiate PRP cells from the single cell PSCs, an accurate count of the input density can increase PRP differentiation efficiency. Thus, the single cell suspension of PSCs is generally counted before seeding. For example, the single cell suspension of PSCs is counted by a hemocytometer or an automated cell counter, such as VICELL® or TC20. The cells may be diluted to a cell density of about 10,000 to about 500,000 cells/mL, about 50,000 to about 200,000 cells/mL, or about 75,000 to about 150,000 cells/mL. In a non-limiting example, the single cell suspension of PSCs is diluted to a density of about 100,000 cells/mL in a fully defined cultured medium such as ESSENTIAL 8™ (E8™) medium.

Once a single cell suspension of PSCs is obtained at a known cell density, the cells are generally seeded in an appropriate culture vessel, such as a tissue culture plate, such as a flask, 6-well, 24-well, or 96-well plate. A culture vessel used for culturing the cell(s) can include, but is particularly not limited to: flask, flask for tissue culture, dish, Petri dish, dish for tissue culture, multi dish, micro plate, micro-well plate, multi plate, multi-well plate, micro slide, chamber slide, tube, tray, CELLSTACK® Chambers, culture bag, and roller bottle, as long as it is capable of culturing the stem cells therein. The cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system ex vivo that supports a biologically active environment such that cells can be propagated. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

In certain aspects, the PSCs, such as iPSCs, are plated at a cell density appropriate for efficient differentiation. Generally, the cells are plated at a cell density of about 1,000 to about 75,000 cells/cm$^2$, such as of about 5,000 to about 40,000 cells/cm$^2$. In a 6 well plate, the cells may be seeded at a cell density of about 50,000 to about 400,000 cells per well. In exemplary methods, the cells are seeded at a cell density of about 100,000, about 150,000, about 200,000, about 250,000, about 300,000 or about 350,000 cells per well, such as about 200,000 cells per well.

The PSCs, such as iPSCs, are generally cultured on culture plates coated by one or more cellular adhesion proteins to promote cellular adhesion while maintaining cell viability. For example, preferred cellular adhesion proteins include extracellular matrix proteins such as vitronectin, laminin, collagen, and/or fibronectin, which may be used to coat a culturing surface as a means of providing a solid support for pluripotent cell growth. The term "extracellular matrix (ECM)" is recognized in the art. Its components can include, but are not limited to, one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. Other ECM components may include synthetic peptides for adhesion (e.g., RGD or IKVAV motifs), synthetic hydrogels (e.g., PEG, PLGA, etc.) or natural hydrogels, such as alginate. In exemplary methods, the PSCs are grown on culture plates coated with vitronectin. In some embodiments, the cellular adhesion proteins are human proteins.

The extracellular matrix proteins may be of natural origin and purified from human or animal tissues or, alternatively, the ECM proteins may be genetically engineered recombinant proteins or synthetic in nature. The ECM proteins may be a whole protein or in the form of peptide fragments, native or engineered. Examples of ECM protein that may be useful in the matrix for cell culture include laminin, collagen I, collagen IV, fibronectin and vitronectin. In some embodiments, the matrix composition is xeno-free. For example, in the xeno-free matrix to culture human cells, matrix components of human origin may be used, wherein any non-human animal components may be excluded.

In some aspects, the total protein concentration in the matrix composition may be about 1 ng/mL to about 1 mg/mL. In some preferred embodiments, the total protein concentration in the matrix composition is about 1 μg/mL to about 300 μg/mL. In more preferred embodiments, the total protein concentration in the matrix composition is about 5 μg/mL to about 200 μg/mL.

Cells, such as PRP cells or PSCs, can be cultured with the nutrients necessary to support the growth of each specific population of cells. Generally, the cells are cultured in growth media including a carbon source, a nitrogen source and a buffer to maintain pH. The medium can also contain fatty acids or lipids, amino acids (such as non-essential amino acids), vitamin(s), growth factors, cytokines, antioxidant substances, pyruvic acid, buffering agents, pH indicators, and inorganic salts. An exemplary growth medium contains a minimal essential media, such as Dulbecco's Modified Eagle's medium (DMEM) or ESSENTIAL 8™ (E8™) medium, supplemented with various nutrients, such as non-essential amino acids and vitamins, to enhance stem cell growth. Examples of minimal essential media include, but are not limited to, Minimal Essential Medium Eagle (MEM) Alpha medium, Dulbecco's modified Eagle medium (DMEM), RPMI-1640 medium, 199 medium, and F12 medium. Additionally, the minimal essential media may be supplemented with additives such as horse, calf or fetal bovine serum. Alternatively, the medium can be serum free. In other cases, the growth media may contain "knockout serum replacement," referred to herein as a serum-free formulation optimized to grow and maintain undifferentiated cells, such as stem cell, in culture. KNOCKOUT™ serum replacement is disclosed, for example, in U.S. Patent Application No. 2002/0076747, which is incorporated herein by reference. Preferably, the PSCs are cultured in a fully-defined and feeder-free media.

Accordingly, the single cell PSCs are generally cultured in a fully defined culture medium after plating. In certain aspects, about 18-24 hours after seeding, the medium is aspirated and fresh medium, such as E8™ medium, is added to the culture. In certain aspects, the single cell PSCs are cultured in the fully defined culture medium for about 1, 2 or 3 days after plating. Preferably, the single cells PSCs are cultured in the fully defined culture medium for about 2 days before proceeding with the differentiation process.

In some embodiments, the medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3-thioglycerol, or equivalents thereto. The alternatives to serum can be prepared by the method disclosed in International Publication No. WO 98/30679, for example. Alternatively, any commercially available materials can be used for more convenience. The commercially available materials include KNOCKOUT™ Serum Replacement (KSR), Chemically-defined Lipid concentrated (Gibco), and GLUTAMAX™ (Gibco).

Other culturing conditions can be appropriately defined. For example, the culturing temperature can be about 30 to 40° C., for example, at least or about 31, 32, 33, 34, 35, 36, 37, 38, 39° C. but particularly not limited to them. In one embodiment, the cells are cultured at 37° C. The C02 concentration can be about 1 to 10%, for example, about 2 to 5%, or any range derivable therein. The oxygen tension can be at least, up to, or about 1, 2, 3, 4, 5, 6, 7, 8, 9, 10, 20%, or any range derivable therein.

A. Differentiation Media

Retinal Induction Medium

After the single cell PSCs have adhered to the culture plate, the cells are preferably cultured in Retinal Induction Medium (RIM) to start the differentiation process into retinal lineage cells. The RIM comprises a WNT pathway inhibitor and can result in the differentiation of PSCs to retinal lineage cells. The RIM additionally comprises a TGFβ pathway inhibitor and a BMP pathway inhibitor. One exemplary RIM medium is shown in Table 1.

The RIM can include DMEM and F12 at about a 1:1 ratio. In exemplary methods, a WNT pathway inhibitor is included in the RIM, such as CKI-7, a BMP pathway inhibitor is included, such as LDN193189, and the TGFβ pathway inhibitor is included, such as SB431542. For example, the RIM comprises about 5 nM to about 50 nM, such as about 10 nM, of LDN193189, about 0.1 μM to about 5 μM, such as about 0.5 μM, of CKI-7, and about 0.5 μM to about 10 μM, such as about 1 μM, of SB431542. Additionally, the RIM can include knockout serum replacement, such as about 1% to about 5%, MEM non-essential amino acids (NEAA), sodium pyruvate, N-2 supplement, B-27 supplement, ascorbic acid, and insulin growth factor 1 (IGF1). Preferably, the IGF1 is animal free IGF1 (AF-IGF1) and is comprised in the RIM from about 0.1 ng/mL to about 10 ng/mL, such as about 1 ng/mL. The media is aspirated each day and replaced with fresh RIM. The cells are generally cultured in the RIM for about 1 to about 5 days, such as about 1, 2, 3, 4 or 5 days, such as for about 2 days to produce anterior neuroectoderm cells.

Retinal Differentiation Medium

The anterior neuroectoderm cells can then be cultured in Retinal Differentiation Medium (RD) for further differentiation. The RD comprises a WNT pathway inhibitor, a TGFβ pathway inhibitor and a MEK inhibitor. In one embodiment, the RD comprises a WNT pathway inhibitor, such as CKI-7, optionally a BMP pathway inhibitor, such as LDN193189, a TGFβ pathway inhibitor, such as SB431542, and a MEK inhibitor, such as PD0325901. Generally, the concentrations of the WNT pathway inhibitor, BMP pathway inhibitor and TGFβ pathway inhibitor are higher in the RDM as compared to the RIM, such as about 9 to about 11 times higher, such as about 10 times higher. In exemplary methods, the RD comprises about 50 nM to about 200 nM, such as about 100 nM of LDN193189, about 1 μM to about 10 μM, such as about 5 μM, of CKI-7, about 1 μM to about 50 μM, such as about 10 μM, of SB431542, and about 0.1 μM to about 10 μM, such as about 1 μM, 2 μM, 3 μM, 4 μM, 5 μM, 6 μM, 7 μM, 8 μM, or 9 μM of PD0325901. Exemplary RD are shown in Table 1.

In some aspects, the cells may be first differentiated in the presence of a BMP inhibitor, such as LDN1913189, for a period of time before differentiation in the absence of a BMP inhibitor. First, the anterior neuroectoderm cells are cultured in RD1 comprising a BMP pathway inhibitor, such as LDN193189, for about 1-3 days, such as 2 days. Next, the cells are cultured in RD2 that does not comprise a BMP pathway inhibitor. The second step may be for about 5-10 days, such as about 7 days, to continue differentiating the anterior neuroectoderm cells. This method was found to increase expression of VSX2 in the subsequently produced PRP cells. VSX2 is the earliest specific marker of neural RPC within the optic vesicle and cup (Rowan, et al., 2004). VSX2$^+$ retinal progenitors can give rise to all cell types of the neural retina: cones, rods, ganglion cells, amacrine cells, bipolar cells, horizontal cells and Muller glia.

Generally, the RD comprises DMEM and F12 at about a 1:1 ratio, knockout serum replacement (e.g., about 1% to about 5%, such as about 1.5%), MEM NEAA, sodium pyruvate, N-2 supplement, B-27 supplement, ascorbic acid and IGF1 (e.g., about 1 ng/mL to about 50 ng/mL, such as about 10 ng/mL). In particular methods, the cells are given fresh RD each day after aspiration of the media from the previous day. Generally, the cells are cultured in the RDM for about 2, 3, 4, 5, 6, 7, 8, 9, 10, 11, 12, 13, 14, 15, or 16 days, such as for about 7 days to differentiate the anterior neuroectoderm cells towards RPCs.

Retinal Maturation Medium

Next, the anterior neuroectoderm cells can be even further differentiated and expanded by culturing the cells in Retinal Maturation Medium (RM) to produce RPCs. The RM may comprise nicotinamide. The RM can comprise about 1 mM to about 50 mM, such as about 10 mM, of nicotinamide. The RM may further comprise ascorbic acid, such as 50-500 μm, particularly about 100-300 μm, such as about 200 μm. Preferably, the RM is free of or essentially free of Activin A. Exemplary RM media are shown in Table 1. The RM (e.g., RM2) may further comprise a γ-secretase inhibitor, such as DAPT, basic FGF, and/or a TGFβ pathway inhibitor, such as SB431542.

The RM can include DMEM and F12 at about a 1:1 ratio, knockout serum replacement at about 1% to about 5%, such as about 1.5%, MEM non-essential amino acids (NEAA), sodium pyruvate, N-2 supplement, B-27 supplement, and ascorbic acid. The medium can be changed daily with room temperature RM. The cells are generally cultured in the RM for about 8, 9, 10, 11, 12, 13, 14, 15, 16 or 17 days, such as for about 10 days to derive expanded RPCs.

PRP Maturation Medium (PM)

The PRPs may be matured in PRP maturation medium (PM). Exemplary PM medium is shown in Table 1. The PM medium comprises ascorbic acid, nicotinamide, and a γ-secretase inhibitor, such as DAPT (e.g., about 1 μM to about 10 μM, such as 5 μM of DAPT). The PM (e.g., PM2) may also comprise a CDK inhibitor, such as a CDK4/6 inhibitor, such as PD0332991 (e.g., about 1 μM to about 50 μM, such as about 10 μM of PD0332991).

The PM Medium can include DMEM and F12 at about a 1:1 ratio, knockout serum replacement at about 1% to about 5%, such as about 1.5%, MEM non-essential amino acids (NEAA), sodium pyruvate, N-2 supplement, B-27 supplement, and ascorbic acid. The medium can be changed daily with room temperature PM Medium. The cells are generally cultured in the PM medium for about 4, 5, 6, 7, 8, 9, 10, 11, 12, 13, 14, 15, 16, 17, 18, 19, or 20 days, such as for about 10 days to derive mature PRP cells.

Photoreceptor Precursor Induction Medium (FDSC)

For further differentiation of the RPCs, the cells are preferably cultured in FDSC Medium. Exemplary FDSC Medium is shown in Table 1. The FDSC Medium comprises a WNT pathway inhibitor, a γ-secretase inhibitor, and a TGFβ pathway inhibitor. In one embodiment, the FDSC comprises a WNT pathway inhibitor, such as CKI-7, a TGFβ pathway inhibitor, such as SB431542, and a γ-secretase inhibitor, such as DAPT. In exemplary methods, the FDSC Medium comprises about 1 μM to about 10 μM, such as about 5 μM, of CKI-7, about 1 μM to about 50 μM, such as about 10 μM, of SB431542, and about 1 μM to about 10 μM, such as about 5 μM of DAPT. The FDSC may also comprise basic FGF.

The FDSC Medium can include DMEM and F12 at about a 1:1 ratio, knockout serum replacement at about 1% to about 5%, such as about 1.5%, MEM non-essential amino acids (NEAA), sodium pyruvate, N-2 supplement, B-27 supplement, and ascorbic acid. In addition, the medium can comprise basic FGF, such as about 5 ng/mL to about 15 ng/mL, such as about 10 ng/mL. The medium can be changed daily with room temperature FDSC Medium. The cells are generally cultured in the FDSC for about 10, 11, 12, 13, 14, 15, 16, 17, 18, 19, or 20 days, such as for about 15 days to derive PRP cells.

TABLE 1

Exemplary Medium Components

| Component | Vendor | Cat# | Final Conc. |
|---|---|---|---|
| Essential 8 Medium | | | |
| Essential 8 ™ Basal Medium | Thermo Fisher | A1517001 | 98% |
| Essential 8 ™ Supplement | Thermo Fisher | | 2% |
| Essential 8 Thawing Medium | | | |
| Complete Essential 8 ™ Medium | Thermo Fisher | As prepared above | 100% |
| Rho Kinase Inhibitor (H1152) | Millipore Sigma | 555550 | 1 μM |
| Essential 8 Plating Medium | | | |
| Complete Essential 8 ™ Medium | Thermo Fisher | As prepared above | 100% |
| Blebbistatin | Millipore Sigma | B0560 | 2.5 μM |
| Retinal Induction Medium (RIM) | | | |
| DMEM/F12 | Thermo Fisher | 11330-032 | 99% |
| CTS ™ KnockOut ™ SR XenoFree | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| CTS ™ N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| LDN-193189 | Stemgent | 04-0074 | 10 nM |
| SB 431542 | R&D Systems | 1614/10 | 1.0 μM |
| CKI-7 Dihydrochloride | Millipore Sigma | C0742 | 0.5 μM |
| AF-IGF-1 | R&D Systems | AFL291 | 1 ng/ml |
| Retinal Differentiation Medium #1 (RD1) | | | |
| DMEM/F12 | Thermo Fisher | 11330-032 | 99% |
| CTS ™ KnockOut ™ SR XenoFree | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| LDN-193189 | Stemgent | 04-0074 | 100 nM |
| SB 431542 | R&D Systems | 1614/10 | 10 μM |
| CKI-7 Dihydrochloride | Millipore Sigma | C0742 | 5 μM |
| AF-IGF-1 | R&D Systems | AFL291 | 10 ng/ml |
| PD0325901 | Stemgent | 04-0006 | 1 μM |
| Retinal Differentiation Medium #2 (RD2) | | | |
| DMEM/F12 | Thermo Fisher | 11330-032 | 99% |
| CTS ™ KnockOut ™ SR XenoFree | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| SB 431542 | R&D Systems | 1614/10 | 10 μM |
| CKI-7 Dihydrochloride | Millipore Sigma | C0742 | 5 μM |
| AF-IGF-1 | R&D Systems | AFL291 | 10 ng/ml |
| PD0325901 | Stemgent | 04-0006 | 1 μM |
| Retinal Maturation Medium #1 (RM1) | | | |
| DMEM/F12 | Thermo Fisher | 11330-032 | 99% |
| CTS ™ KnockOut ™ SR XenoFree Kit | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| CTS ™ N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| Nicotinamide | Millipore Sigma | N0636 | 10 mM |
| Retinal Maturation Medium #2 (RM2) | | | |
| DMEM/F12 | Thermo Fisher | 11330-032 | 99% |
| CTS ™ KnockOut ™ SR XenoFree Kit | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| CTS ™ N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| Nicotinamide | Millipore Sigma | N0636 | 10 mM |
| basic FGF | R&D Systems | AFL233 | 10-100 ng/ml |
| SB 431542 | R&D Systems | 1614/10 | 10 μM |
| PRP Maturation Medium #1 (PM1) | | | |
| DMEM/F12 | Thermo Fisher | 11330-032 | 99% |
| CTS ™ KnockOut ™ SR XenoFree Kit | Thermo Fisher | A1099201 | 1.50% |
| MEM non-essential AA | Thermo Fisher | 11140 | 0.1 mM |

TABLE 1-continued

Exemplary Medium Components

| Component | Vendor | Cat# | Final Conc. |
|---|---|---|---|
| Sodium Pyruvate | Thermo Fisher | 11360-070 | 1 mM |
| CTS ™ N-2 Supplement | Thermo Fisher | A13707-01 | 1% |
| B-27® Supplement (+VitA) | Thermo Fisher | 17504-044 | 2% |
| Ascorbic Acid | Millipore Sigma | A4544 | 200 μM |
| Nicotinamide | Millipore Sigma | N0636 | 10 mM |
| DAPT | Millipore Sigma | D5942 | 5 μM |
| PRP Maturation Medium #1 (PM2) | | | |
| DMEM/F12 | Thermo Fisher | 11330-032 | 99% |
| CTS ™ KnockOut ™ SR XenoFree Kit | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| CTS ™ N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| Nicotinamide | Millipore Sigma | N0636 | 10 mM |
| DAPT | Millipore Sigma | D5942 | 5 μM |
| PD0332991 | Tocris | 4786 | 10 μM |
| Photoreceptor Precursor Induction Medium (FDSC) | | | |
| DMEM/F12 | Thermo Fisher | 11330-032 | 99% |
| CTS ™ KnockOut ™ SR XenoFree Kit | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| CTS ™ N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| basic FGF | R&D Systems | AFL233 | 10 ng/mL |
| DAPT | Millipore Sigma | D5942 | 5 μM |
| SB 431542 | R&D Systems | 1614/10 | 10 μM |
| CKI-7 Dihydrochloride | Millipore Sigma | C0742 | 5 μM |
| MACS Buffer | | | |
| DPBS (without calcium and magnesium) | Thermo Fisher | 14190-144 | 98% |
| Fetal Bovine Serum | GE Life Sciences | SH30071.03 | 2% |
| UltraPure ™ EDTA Solution | Thermo Fisher | 15575-020 | 2 mM |
| Post-thaw Medium #1 (PT1) | | | |
| Neurobasal CTS Grade | Thermo Fisher | A13712-01 | 99% |
| CTS ™ N-2 Supplement | Thermo Fisher | A13707-01 | 1% |
| Glutamax | Thermo Fisher | 35050-061 | 1% |
| Y-27632 | Tocris | 1254/10 | 10 μM |
| Post-thaw Medium #2 (PT2) | | | |
| DMEM/F12 | Thermo Fisher | 11330-032 | 99% |
| CTS ™ KnockOut ™ SR XenoFree Kit | Thermo Fisher | A1099201 | 1.50% |
| MEM non-essential AA | Thermo Fisher | 11140 | 0.1 mM |
| Sodium Pyruvate | Thermo Fisher | 11360-070 | 1 mM |
| CTS ™ N-2 Supplement | Thermo Fisher | A13707-01 | 1% |
| B-27 ® Supplement (+VitA) | Thermo Fisher | 17504-044 | 2% |
| Ascorbic Acid | Millipore Sigma | A4544 | 200 μM |
| Nicotinamide | Millipore Sigma | N0636 | 10 mM |
| Y-27632 (optional) | Tocris | 1254/10 | 10 μM |

In addition, Blebbistatin (e.g., about 2.5 μM) can be added to the medium to increase PRP survival and maintain purity by promoting aggregate formation. A ROCK inhibitor instead of Blebbistatin may alternatively be used to increase PRP survival after dissociation into single cells, such as by using TRYPLE™.

The PRP aggregates may be cultured to produce hybrid photoreceptor cells or optic vesicles.

B. Cryopreservation of PRP Cells

The photoreceptor precursor cells produced by the methods disclosed herein can be cryopreserved, see for example, PCT Publication No. 2012/149484 A2, which is incorporated by reference herein. The cells can be cryopreserved with or without a substrate. In several embodiments, the storage temperature ranges from about −50° C. to about −60° C., about −60° C. to about −70° C., about −70° C. to about −80° C., about −80° C. to about −90° C., about −90° C. to about −100° C., and overlapping ranges thereof. In some embodiments, lower temperatures are used for the storage (e.g., maintenance) of the cryopreserved cells. In several embodiments, liquid nitrogen (or other similar liquid coolant) is used to store the cells. In further embodiments, the cells are stored for greater than about 6 hours. In additional embodiments, the cells are stored about 72 hours. In several embodiments, the cells are stored 48 hours to about one week. In yet other embodiments, the cells are stored for about 1, 2, 3, 4, 5, 6, 7, or 8 weeks. In further embodiments, the cells are stored for 1, 2, 3, 4, 5, 6, 7, 8, 9, 10, 11 or 12 months. The cells can also be stored for longer times. The cells can be cryopreserved separately or on a substrate, such as any of the substrates disclosed herein.

In some embodiments, additional cryoprotectants can be used. For example, the cells can be cryopreserved in a cryopreservation solution comprising one or more cryoprotectants, such as DM80, serum albumin, such as human or bovine serum albumin. In certain embodiments, the solution comprises about 1%, about 1.5%, about 2%, about 2.5%, about 3%, about 4%, about 5%, about 6%, about 7%, about 8%, about 9%, or about 10% DMSO. In other embodiments, the solution comprises about 1% to about 3%, about 2% to about 4%, about 3% to about 5%, about 4% to about 6%, about 5% to about 7%, about 6% to about 8%, about 7% to about 9%, or about 8% to about 10% dimethylsulfoxide (DMSO) or albumin. In a specific embodiment, the solution comprises 2.5% DMSO. In another specific embodiment, the solution comprises 10% DMSO.

Cells may be cooled, for example, at about 1° C./minute during cryopreservation. In some embodiments, the cryopreservation temperature is about −80° C. to about −180° C., or about −125° C. to about −140° C. In some embodiments, the cells are cooled to 4° C. prior to cooling at about 1° C./minute. Cryopreserved cells can be transferred to vapor phase of liquid nitrogen prior to thawing for use. In some embodiments, for example, once the cells have reached about −80° C., they are transferred to a liquid nitrogen storage area. Cryopreservation can also be done using a controlled-rate freezer. Cryopreserved cells may be thawed, e.g., at a temperature of about 25° C. to about 40° C., and typically at a temperature of about 37° C.

Alternatively, the cells may be cryopreserved as aggregates without dissociation into a single cell suspension. For example, following PRP enrichment, single cells may be allowed to re-aggregate in tissue culture flasks for two days in minimal medium (RMN). Aggregates may be pooled and a sample aliquot obtained for cell counts. Following a series of washes, aggregates can be resuspended in CryoSTOR CS10 Freeze Medium and the aggregate suspensions may be transferred to liquid nitrogen storage vials, such as at 25×10^6 aggregated cell products/vial.

C. Inhibitors

WNT Pathway Inhibitors

WNT is a family of highly conserved secreted signaling molecules that regulate cell-to-cell interactions and are related to the *Drosophila* segment polarity gene, wingless. In humans, the WNT family of genes encodes 38 to 43 kDa cysteine rich glycoproteins. The WNT proteins have a hydrophobic signal sequence, a conserved asparagine-linked oligosaccharide consensus sequence (see e.g., Shimizu et al Cell Growth Differ 8: 1349-1358 (1997)) and 22 conserved cysteine residues. Because of their ability to promote stabilization of cytoplasmic beta-catenin, WNT proteins can act as transcriptional activators and inhibit apoptosis. Overexpression of particular WNT proteins has been shown to be associated with certain cancers.

A WNT inhibitor (also referred to as a WNT pathway inhibitor) herein refers to WNT inhibitors in general. Thus, a WNT inhibitor refers to any inhibitor of a member of the WNT family proteins including Wnt1, Wnt2, Wnt2b, Wnt3, Wnt4, Wnt5A, Wnt6, Wnt7A, Wnt7B, Wnt8A, Wnt9A, Wnt10a, Wnt11, and Wnt16. Certain embodiments of the present methods concern a WNT inhibitor in the differentiation medium. Examples of suitable WNT inhibitors, already known in the art, include N-(2-Aminoethyl)-5-chloroisoquinoline-8-sulphonamide dihydrochloride (CKI-7), N-(6-Methyl-2-benzothiazolyl)-2-[(3,4,6,7-tetrahydro-4-oxo-3-phenylthieno[3,2-d]pyrimidin-2-yl)thio]-acetamide (IWP2), N-(6-Methyl-2-benzothiazolyl)-2-[(3,4,6,7-tetrahydro-3-(2-methoxyphenyl)-4-oxothieno[3,2-d]pyrimidin-2-yl)thio]-acetamide (IWP4), 2-Phenoxybenzoic acid-[(5-methyl-2-furanyl)methylene]hydrazide (PNU 74654) 2,4-diamino-quinazoline, quercetin, 3,5,7,8-Tetrahydro-2-[4-(trifluoromethyl)phenyl]-4H-thiopyrano[4,3-d]pyrimidin-4-one (XAV939), 2,5-Dichloro-N-(2-methyl-4-nitrophenyl) benzenesulfonamide (FH 535), N-[4-[2-Ethyl-4-(3-methylphenyl)-5-thiazolyl]-2-pyridinyl]benzamide (TAK 715), Dickkopf-related protein one (DKK1), and Secreted frizzled-related protein (SFRP1) 1. In addition, inhibitors of WNT can include antibodies to, dominant negative variants of, and siRNA and antisense nucleic acids that suppress expression of WNT. Inhibition of WNT can also be achieved using RNA-mediated interference (RNAi).

BMP Pathway Inhibitors

Bone morphogenic proteins (BMPs) are multi-functional growth factors that belong to the transforming growth factor beta (TGFβ) superfamily. BMPs are considered to constitute a group of pivotal morphogenetic signals, orchestrating architecture through the body. The important functioning of BMP signals in physiology is emphasized by the multitude of roles for dysregulated BMP signaling in pathological processes.

BMP pathway inhibitors (also referred to herein as BMP inhibitors) may include inhibitors of BMP signaling in general or inhibitors specific for BMP1, BMP2, BMP3, BMP4, BMP5, BMP6, BMP7, BMP8a, BMP8b, BMP10 or BMP15. Exemplary BMP inhibitors include 4-(6-(4-(piperazin-1-yl)phenyl)pyrazolo[1,5-a]pyrimidin-3-yl)quinoline hydrochloride (LDN193189), 6-[4-[2-(1-Piperidinyl) ethoxy]phenyl]-3-(4-pyridinyl)-pyrazolo[1,5-a]pyrimidine dihydrochloride (Dorsomorphin), 4-[6-[4-(1-Methylethoxy) phenyl]pyrazolo[1,5-a]pyrimidin-3-yl]-quinoline (DMH1), 4-[6-[4-[2-(4-Morpholinyl)ethoxy]phenyl]pyrazolo[1,5-a] pyrimidin-3-yl]quinoline (DMH-2), and 5-[6-(4-Methoxyphenyl)pyrazolo[1,5-a]pyrimidin-3-yl]quinoline (ML 347).

TGFβ Pathway Inhibitors

Transforming growth factor beta (TGFβ) is a secreted protein that controls proliferation, cellular differentiation, and other functions in most cells. It is a type of cytokine which plays a role in immunity, cancer, bronchial asthma, lung fibrosis, heart disease, diabetes, and multiple sclerosis. TGF-β exists in at least three isoforms called TGF-β1, TGF-β2 and TGF-β3. The TGF-β family is part of a superfamily of proteins known as the transforming growth factor beta superfamily, which includes inhibins, activin, anti-mullerian hormone, bone morphogenetic protein, decapentaplegic and Vg-1.

TGFβ pathway inhibitors (also referred to herein as TGFβ inhibitors) may include any inhibitors of TGFβ signaling in general. For example, the TGFβ inhibitor is 4-[4-(1,3-benzodioxol-5-yl)-5-(2-pyridinyl)-1H-imidazol-2-yl]benzamide (SB431542), 6-[2-(1,1-Dimethylethyl)-5-(6-methyl-2-pyridinyl)-1H-imidazol-4-yl]quinoxaline (SB525334), 2-(5-Benzo[1,3]dioxol-5-yl-2-ieri-butyl-3H-imidazol-4-yl)-6-methylpyridine hydrochloride hydrate (SB-505124), 4-(5-Benzol[1,3]dioxol-5-yl-4-pyridin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, left-right determination factor (Lefty), 3-(6-Methyl-2-pyridinyl)-N-phenyl-4-(4-quinolinyl)-1H-pyrazole-1-carbothioamide (A 83-01), 4-[4-(2,3-Dihydro-1,4-benzodioxin-6-yl)-5-(2-pyridinyl)-1H-imidazol-2-yl]benzamide (D 4476), 4-[4-[3-(2-Pyridinyl)-1H-pyrazol-4-yl]-2-pyridinyl]-N-(tetrahydro-2H-pyran-4-yl)-benzamide (GW 788388), 4-[3-(2-Pyridinyl)-1H-pyrazol-4-yl]-quinoline (LY 364847), 4-[2-Fluoro-5-[3-(6-methyl-2-pyridinyl)-1H-pyrazol-4-yl] phenyl]-1H-pyrazole-1-ethanol (R 268712) or 2-(3-(6-Methylpyridine-2-yl)-1H-pyrazol-4-yl)-1,5-naphthyridine (RepSox).

MEK Inhibitors

A MEK inhibitor is a chemical or drug that inhibits the mitogen-activated protein kinase enzymes MEK1 or MEK2. They can be used to affect the MAPK/ERK pathway. For example, MEK inhibitors include N-[(2R)-2,3-Dihydroxypropoxy]-3,4-difluoro-2-[(2-fluoro-4-iodophenyl)amino]-benzamide (PD0325901), N-[3-[3-cyclopropyl-5-(2-fluoro-4-iodoanilino)-6,8-dimethyl-2,4,7-trioxopyrido[4,3-d] pyrimidin-1-yl]phenyl]acetamide (GSK1120212), 6-(4-bromo-2-fluoroanilino)-7-fluoro-N-(2-hydroxyethoxy)-3-methylbenzimidazole-5-carboxamide (MEK162), N-[3,4- difluoro-2-(2-fluoro-4-iodoanilino)-6-methoxyphenyl]-1-(2,3-dihydroxypropyl)cyclopropane-1-sulfonamide (RDEA119), and 6-(4-bromo-2-chloroanilino)-7-fluoro-N-(2-hydroxyethoxy)-3-methylbenzimidazole-5-carboxamide (AZD6244).

Gamma-Secretase Inhibitors

Gamma secretase is a multi-subunit protease complex, itself an integral membrane protein, that cleaves single-pass transmembrane proteins at residues within the transmembrane domain. Proteases of this type are known as intramembrane proteases. The most well-known substrate of gamma secretase is amyloid precursor protein, a large integral membrane protein that, when cleaved by both gamma and beta secretase, produces a short amino acid peptide called amyloid beta whose abnormally folded fibrillar form is the primary component of amyloid plaques found in the brains of Alzheimer's disease patients.

Gamma secretase inhibitors herein refer to γ-secretase inhibitors in general. For example, γ-secretase inhibitors include, but are not limited to N-[(3,5-Difluorophenyl) acetyl]-L-alanyl-2-phenyl]glycine-1,1-dimethylethyl ester (DAPT), 5-Chloro-N-[(1S)-3,3,3-trifluoro-1-(hydroxymethyl)-2-(trifluoromethyl)propyl]-2-thiophenesulfonamide (Begacestat), MDL-28170,3,5-Bis(4-nitrophenoxy)benzoic acid (Compound W), 7-Amino-4-chloro-3-methoxy-1H-2-benzopyran (JLK6), (5S)-(tert-Butoxycarbonylamino)-6-phenyl-(4R)-hydroxy-(2R)-benzylhexanoyl)-L-leucy-L-phenylalaninamide (L-685,485), (R)-2-Fluoro-α-methyl[1, 1'-biphenyl]-4-acetic acid ((R)-Flurbiprofen; Flurizan), N-[(1S)-2-[[(7S)-6,7-Dihydro-5-methyl-6-oxo-5H-dibenz [b,d]azepin-7-yl]amino]-1-methyl-2-oxoethyl]-3,5-difluorobenzeneacetamide (Dibenzazepine; DBZ), N-[cis-4-[(4-Chlorophenyl)sulfonyl]-4-(2,5-difluorophenyl)cyclohexyl]-1,1,1-trifluoromethanesulfonamide (MRK560), (2S)-2-[[(2S)-6,8-Difluoro-1,2,3,4-tetrahydro-2-naphthalenyl] amino]-N-[1-[2-[(2,2-dimethylpropyl)amino]-1,1-dimethylethyl]-1H-imidazol-4-yl]pentanamide dihydrobromide (PF3084014 hydrobromide) and 2-[(1R)-1-[[(4-Chlorophenyl)sulfonyl](2,5-difluorophenyl)amino]ethyl-5-fluorobenzenebutanoic acid (BMS299897).

Cyclin Dependent Kinase Inhibitors

Cyclin dependent kinases (CDKs) are a family of sugar kinases first discovered for their role in regulating the cell cycle. They are also involved in regulating transcription, mRNA processing, and the differentiation of nerve cells. In many human cancers, CDKs are overactive or CDK-inhibiting proteins are not functional. CDK inhibitors may be CDK1, CDK2, CDK3, CDK4, CDK5, CDK6, CDK7, CDK8, and/or CDK9 inhibitors. In particular aspects, the CDK inhibitor is a CDK4/6 inhibitor.

CDK inhibitors may include, but are not limited to, Palbociclib (PD-0332991) HCl, Roscovitine (Seliciclib, CYC202), SNS-032 (BMS-387032), Dinaciclib (SCH727965), Flavopiridol (Alvocidib), MSC2530818, JNJ-7706621, AZD5438, MK-8776 (SCH 900776), PHA-793887, BS-181 HCl, A-674563, abemaciclib (LY2835219), BMS-265246, PHA-767491, or Milciclib (PHA-848125).

IV. USE OF PHOTORECEPTOR PRECURSOR CELLS

Certain aspects provide a method to produce a PRP or PRP-enriched cell population which can be used for a number of important research, development, and commercial purposes.

In some aspects, the methods disclosed herein result in a cell population of at least or about $10^6$, $10^7$, $10^8$, $5\times10^8$, $10^9$, $10^{10}$ cells (or any range derivable therein) comprising at least or about 50% (for example, at least or about 60%, 70%, 80%, 85%, 90%, 95%, 96%, 97%, 98%, 99%, 99.5%, or any range derivable therein) PRP cells.

In certain aspects, starting cells for the present methods may comprise the use of at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about $10^1$, $10^2$, $10^3$, $10^4$, $10^5$, $10^6$, $10^7$, $10^8$ cells/mL, or any range derivable therein.

The PRP cells or photoreceptor cells produced by the methods disclosed herein may be used in any methods and applications currently known in the art for PRP or photoreceptor cells. For example, a method of assessing a compound may be provided, comprising assaying a pharmacological or toxicological property of the compound on the PRP or photoreceptor cell. There may also be provided a method of assessing a compound for an effect on a PRP cell, comprising: a) contacting the PRP cells provided herein with the compound; and b) assaying an effect of the compound on the PRP cells.

The PRP cells or cells derived from the PRP cells may be used for transplantation such as cell rescue therapy or whole tissue replacement therapy. The cells of the present embodiments may also be used to produce retinal disease models to study pathophysiology and for drug screening.

A. Test Compound Screening

PRP cells can be used commercially to screen for factors (such as solvents, small molecule drugs, peptides, oligonucleotides) or environmental conditions (such as culture conditions or manipulation) that affect the characteristics of such cells and their various progeny. For example, test compounds may be chemical compounds, small molecules, polypeptides, growth factors, cytokines, or other biological agents.

In one embodiment, a method includes contacting a PRP cell with a test agent and determining if the test agent modulates activity or function of PRP cells within the population. In some applications, screening assays are used for the identification of agents that modulate PRP cell proliferation, alter PRP cell differentiation, or affect cell viability. Screening assays may be performed in vitro or in vivo. Methods of screening and identifying ocular agents or PRP agents include those suitable for high-throughput screening. For example, PRP cells can be positioned or placed on a culture dish, flask, roller bottle or plate (e.g., a single multi-well dish or dish such as 8, 16, 32, 64, 96, 384 and 1536 multi-well plate or dish), optionally at defined locations, for identification of potentially therapeutic molecules. Libraries that can be screened include, for example, small molecule libraries, siRNA libraries, and adenoviral transfection vector libraries.

Other screening applications relate to the testing of pharmaceutical compounds for their effect on retinal tissue maintenance or repair. Screening may be done either because the compound is designed to have a pharmacological effect on the cells, or because a compound designed to have effects elsewhere may have unintended side effects on cells of this tissue type.

B. Therapy and Transplantation

Other embodiments can also provide use of PRP cells to enhance ocular tissue maintenance and repair for any condition in need thereof, including retinal degeneration or significant injury. Retinal degeneration may be associated with age-related macular degeneration (AMD), Stargardt's macular dystrophy, retinitis pigmentosa, glaucoma, retinal vascular disease, viral infection of the eye, and other retinal/ ocular disease. The photoreceptor precursor progenitor cells may comprise at least 50%, at least 75%, at least 85%, at least 95%, at least 99% or about 100% of the cells in the culture.

In another aspect, the disclosure provides a method of treatment of an individual in need thereof, comprising administering a composition comprising photoreceptor precursor cells to said individual. Said composition may be administered to the eye, subretinal space, or intravenously. Such individuals may have macular degeneration including age-related macular degeneration, and such macular degeneration may be early or late stage. Such individuals may have retinitis pigmentosa, Stargardt's disease, retinal dysplasia, retinal degeneration, diabetic retinopathy, congenital retinal dystrophy, Leber congenital amaurosis, retinal detachment, glaucoma, or optic neuropathy.

To determine suitability of cell compositions for therapeutics administration, the cells can first be tested in a suitable animal model. In one aspect, the PRP cells are evaluated for their ability to survive and maintain their phenotype in vivo. Cell compositions are administered to immunodeficient animals (e.g., nude mice or animals rendered immunodeficient chemically or by irradiation). Tissues are harvested after a period of growth, and assessed as to whether the pluripotent stem cell-derived cells are still present.

A number of animals are available for testing of the suitability of the PRP cell compositions. For example, the Royal College of Surgeon's (RCS) rat is a well-known model of retinal dystrophy (Lund et al., 2006). In addition, PRP cell suitability and survival can be determined by transplantation (e.g., subcutaneous or subretinal) in Matrigel in immunodeficient animals such as NOG mice (Kanemura et al., 2014). Other models that may be used include, but are not limited to, the S334ter rat model of retinal degeneration and the NIH Rowett nude (RNU) rat model.

The human PRP cells described herein, or a pharmaceutical composition including these cells, can be used for the manufacture of a medicament to treat a condition in a patient in need thereof. The PRP cells can be previously cryopreserved. In certain aspects, the disclosed PRP cells are derived from iPSCs, and thus can be used to provide "personalized medicine" for patients with eye diseases. In some embodiments, somatic cells obtained from patients can be genetically engineered to correct the disease-causing mutation, differentiated into PRP, and engineered to form a PRP tissue. This PRP tissue can be used to replace the endogenous degenerated PRP of the same patient. Alternatively, iPSCs generated from a healthy donor or from HLA homozygous "super-donors" can be used.

Various eye conditions may be treated or prevented by the introduction of the PRP cells obtained using the methods disclosed herein. The conditions include retinal diseases or disorders generally associated with retinal dysfunction or degradation, retinal injury, and/or loss of retinal pigment epithelium. Conditions that can be treated include, without limitation, degenerative diseases of the retina, such as Stargardt's macular dystrophy, retinitis pigmentosa, macular degeneration (such as age-related macular degeneration), glaucoma, and diabetic retinopathy. Additional conditions include Lebers congenital amaurosis, hereditary or acquired macular degeneration, Best disease, retinal detachment, gyrate atrophy, choroideremia, pattern dystrophy, other dystrophies of photoreceptor cells, and retinal damage due to damage caused by any one of photic, laser, inflammatory, infectious, radiation, neovascular or traumatic injury. In certain embodiments, methods are provided for treating or preventing a condition characterized by retinal degeneration, comprising administering to a subject in need thereof an effective amount of a composition comprising PRP cells. These methods can include selecting a subject with one or more of these conditions, and administering a therapeutically effective amount of the PRP cells sufficient to treat the condition and/or ameliorate symptoms of the condition. The PRP cells may be transplanted in various formats. For example, the PRP cells may be introduced into the target site in the form of cell suspension, or adhered onto a matrix, extracellular matrix or substrate such as a biodegradable polymer, as a monolayer, or a combination. The PRP cells may also be transplanted together (co-transplantation) with other retinal cells, such as with retinal pigment epithelium cells. In some embodiments, the PRP cells are produced from iPSCs from the subject to be treated, and thus are autologous. In other embodiments, the PRP cells are produced from an MHC-matched donor.

Advantageously, the pharmaceutical preparations of the present disclosure may be used to compensate for a lack or diminution of photoreceptor cell function. Examples of retinal dysfunction that can be treated by the retinal cell populations and methods of the invention include but are not limited to: photoreceptor degeneration (as occurs in, e.g., retinitis pigmentosa, cone dystrophies, cone-rod and/or rod-cone dystrophies, and macular degeneration); retina detachment and retinal trauma; photic lesions caused by laser or sunlight; a macular hole; a macular edema; night blindness and color blindness; ischemic retinopathy as caused by diabetes or vascular occlusion; retinopathy due to prematurity/premature birth; infectious conditions, such as CMV, retinitis and toxoplasmosis; inflammatory conditions, such as the uveitidies; tumors, such as retinoblastoma and ocular melanoma; and for the replacement of inner retinal neurons, which are affected in ocular neuropathies including glaucoma, traumatic optic neuropathy, and radiation optic neuropathy and retinopathy.

In one aspect, the cells can treat or alleviate the symptoms of retinitis pigmentosa in a patient in need of the treatment. In another aspect, the cells can treat or alleviate the symptoms of macular degeneration, such as age-related macular degeneration (wet or dry), Stargardt's disease, myopic macular degeneration or the like, in a patient in need of this treatment. For all of these treatments, the cells can be autologous or allogeneic to the patient. In a further aspect, the cells of the present disclosure can be administered in combination with other treatments.

In some embodiments, the PRP cells can be used for autologous PRP grafts to those subjects suitable for receiving regenerative medicine. The PRP cells may be transplanted in combination with other retinal cells, such as with photoreceptors. Transplantation of the PRP cells produced by the disclosed methods can be performed by various techniques known in the art. In accordance with one embodiment, the transplantation is performed via pars pana vitrectomy surgery followed by delivery of the cells through a small retinal opening into the sub-retinal space or by direct injection. The PRP cells can be introduced into the target site in the form of cell suspension, cell aggregates, adhered onto a matrix, such as extracellular matrix, or provided on substrate such as a biodegradable polymer. The PRP cells can also be transplanted together (co-transplantation) with other cells, such as PRP cells with retinal pigment epithelial (RPE) cells. Thus, a composition comprising PRP cells obtained by the methods disclosed herein is provided.

The PRP cells, and optionally the photoreceptor cells differentiated therefrom, can be used to generate neurosensory retinal structures. For instance, the present disclosure contemplates the generation of multilayer cellular structures comprised of RPE cells and photoreceptor cells (or PRP cells). These structures can be used for drug screening, as models for diseases, or as or in a pharmaceutical preparation. In the latter case, the pharmaceutical preparation can be an RPE-photoreceptor graft, which may be disposed on a biocompatible solid support or matrix (preferably a bioresorbable matrix or support) that can be implanted like a "patch".

To further illustrate, the biocompatible support for the cells can be a biodegradable synthetic, such as polyester, film support for retinal progenitor cells. The biodegradable polyester can be any biodegradable polyester suitable for use as a substrate or scaffold for supporting the proliferation and differentiation of retinal progenitor cells. The polyester should be capable of forming a thin film, preferably a micro-textured film, and should be biodegradable if used for tissue or cell transplantation. Suitable biodegradable polyesters for use in the invention include polylactic acid (PLA), polylactides, polyhydroxyalkanoates, both homopolymers and co-polymers, such as polyhydoxybutyrate (PHB), polyhydroxybutyrate co-hydroxyvalerate (PHBV), polyhydroxybutyrate co-hydroxyhexanote (PHBHx), polyhydroxybutyrate co-hydroxyoctonoate (PHBO) and polyhydroxybutyrate co-hydroxyoctadecanoate (PHBOd), polycaprolactone (PCL), polyesteramide (PEA), aliphatic copolyesters, such as polybutylene succinate (PBS) and polybutylene succinate/adipate (PBSA), aromatic copolyesters. Both high and low molecular weight polyesters, substituted and unsubstituted polyester, block, branched or random, and polyester mixtures and blends can be used. Preferably the biodegradable polyester is polycaprolactone (PCL).

Pharmaceutical compositions of the PRP cells produced by the methods disclosed herein. These compositions can include at least about $1 \times 10^3$ PRP cells, about $1 \times 10^4$ PRP cells, about $1 \times 10^5$ PRP cells, about $1 \times 10^6$ PRP cells, about $1 \times 10^7$ PRP cells, about $1 \times 10^8$ PRP cells, or about $1 \times 10^9$ PRP cells. In certain embodiments, the compositions are substantially purified (with respect to non-PRP cells) preparations comprising differentiated PRP cells produced by the methods disclosed herein. Compositions are also provided that include a scaffold, such as a polymeric carrier and/or an extracellular matrix, and an effective amount of the PRP cells produced by the methods disclosed herein. For example, the cells are provided as a monolayer of cells. The matrix material is generally physiologically acceptable and suitable for use in in vivo applications. For example, the physiologically acceptable materials include, but are not limited to, solid matrix materials that are absorbable and/or non-absorbable, such as small intestine submucosa (SIS), crosslinked or non-crosslinked alginate, hydrocolloid, foams, collagen gel, collagen sponge, polyglycolic acid (PGA) mesh, fleeces and bioadhesives.

Suitable polymeric carriers also include porous meshes or sponges formed of synthetic or natural polymers, as well as polymer solutions. For example, the matrix is a polymeric mesh or sponge, or a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers. For example, biodegradable polymers include polymers of hydroxy acids such as polyactic acid (PLA), polyglycolic acid (PGA) and polylactic acid-glycolic acid (PGLA), polyorthoesters, polyanhydrides, polyphosphazenes, and combinations thereof. Non-biodegradable polymers include polyacrylates, polymethacrylates, ethylene vinyl acetate, and polyvinyl alcohols.

Polymers that can form ionic or covalently crosslinked hydrogels which are malleable can be used. A hydrogel is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as PLURON1CS™ or TETRON1CS™, polyethylene oxide-polypropylene glycol block copolymers which are crosslinked by temperature or H, respectively. Other materials include proteins such as fibrin, polymers such as polyvinylpyrrolidone, hyaluronic acid and collagen.

The pharmaceutical compositions can be optionally packaged in a suitable container with written instructions for a desired purpose, such as the reconstitution of PRP cell function to improve a disease or abnormality of the retinal tissue. In some embodiments, the PRP cells produced by the disclosed methods may be used to replace degenerated photoreceptor cells of a subject in need therein.

C. Distribution for Commercial, Therapeutic, and Research Purposes

In some embodiments, a reagent system is provided that includes a set or combination of cells comprising a PRP or PRP-enriched cell population that exists at any time during manufacture, distribution or use. The cell sets comprise any combination of the cell population described herein in combination with undifferentiated pluripotent stem cells or other differentiated cell types, often sharing the same genome. Each cell type may be packaged together, or in separate containers in the same facility, or at different locations, at the same or different times, under control of the same entity or different entities sharing a business relationship.

Pharmaceutical compositions may optionally be packaged in a suitable container with written instructions for a desired purpose, such as the reconstitution of PRP cell function to improve a disease or injury of the ocular tissue.

V. KITS

In some embodiments, a kit that can include, for example, one or more media and components for the production of PRP cells is provided. Such formulations may comprise a cocktail of retinal differentiation and/or trophic factors, in a form suitable for combining with photoreceptor precursor or photoreceptor cells. The reagent system may be packaged either in aqueous media or in lyophilized form, where appropriate. The container means of the kits will generally include at least one vial, test tube, flask, bottle, syringe or other container means, into which a component may be placed, and preferably, suitably aliquoted.

Where there is more than one component in the kit, the kit also will generally contain a second, third or other additional container into which the additional components may be separately placed. However, various combinations of components may be comprised in a vial. The components of the kit may be provided as dried powder(s). When reagents and/or components are provided as a dry powder, the powder can be reconstituted by the addition of a suitable solvent. It is envisioned that the solvent may also be provided in another container means. The kits also will typically include a means for containing the kit component(s) in close confinement for commercial sale. Such containers may include injection or blow molded plastic containers into which the desired vials are retained. The kit can also include instructions for use, such as in printed or electronic format, such as digital format.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Preparation of Starting Pluripotent Stem Cell Population

A method was developed for the differentiation of iPSCs into different stages of photoreceptor precursors (PRPs) (FIG. 1). Briefly, a population of retinal progenitor cells (RPCs) is derived from iPSCs which are then further differentiated to neural retinal progenitors (NRPs) and then PRP cells.

First, the iPSCs were grown without mouse or human feeder layers in fully defined-culture medium, such as ESSENTIAL 8™ (E8™) medium, on a plate coated by vitronectin. The vitronectin stock was diluted 1:200 in DPBS without calcium or magnesium and the culture plates were coated with the diluted vitronectin solution and incubated at room temperature for about 1 hour. The iPSCs were split when they were pre-confluent and not allowed to overgrow to prevent unhealthy and/or differentiated cells.

To derive RPCs, the iPSCs were first dissociated into a single cell suspension. To obtain the single cell suspension, the cells were washed with DPBS (without calcium and magnesium) and incubated in a cell dissociation enzyme such as TRYPLE™ for about 10 min at 37° C. The cells were then detached by pipetting with a serological pipet and the cell suspension was collected in a conical tube. If the cells did not detach with gently pipetting, the cultures were incubated longer, such as 2-3 additional minutes. To collect all cells, the culture vessel was washed with room temperature E8™ medium, and the medium was then added to the tube containing the cell suspension. In addition, Blebbistatin (e.g. 2.5 µM) was added to the E8™ Medium to increase PSC survival after dissociation into single cells while the cells are not adhered to a culture vessel. To collect the cells, they were centrifuged at 400×g for about 5 minutes, the supernatant was aspirated and the cells were resuspended in an appropriate volume of E8™ medium.

To efficiently differentiate PRP cells from the single cell iPSCs, the input density of the single cell iPSCs was accurately counted by an automated cell counter such as VICELL™ and diluted to a cell suspension of about $1 \times 10^5$ cells/mL in room temperature E8™ medium. Once the single cell suspension of iPSCs was obtained at a known cell density (e.g., by hemocytometer), the cells were plated in an appropriate culture vessel such as a 6-well plate coated with vitronectin. The cells were seeded at a cell density of about 200,000 cells per well and placed in a humidified incubator at 5% $CO_2$ and 37° C. After about 18-24 hours, the medium was aspirated and fresh E8™ medium was added to the culture. The cells were cultured in the E8™ medium for about 2 days after seeding for proper adherence and iPSC expansion.

Example 2—Differentiation of iPSCs into RPCs

Once the single-cell iPSCs seeded at the appropriate cell density were cultured for about 2 days as in Example 1, they were cultured in various differentiation media for deriving RPCs. The E8™ medium was aspirated and room temperature Retinal Induction Medium (RIM) (e.g., Table 1) was added. Briefly, the RIM comprised DMEM and F12 at about a 1:1 ratio, knockout serum replacement, MEM non-essential amino acids (NEAA), sodium pyruvate, N-2 supplement, B-27 supplement, and ascorbic acid. In addition, the RIM comprised a WNT pathway inhibitor, a BMP pathway inhibitor, a TGFβ pathway inhibitor and insulin growth factor 1 (IGF1). Each day the media was aspirated and fresh RIM was added to the cells. The cells were cultured in the RIM for about two days to generate anterior neuroectoderm cells.

The cells were then cultured in Retinal Differentiation Medium 1 (RD1) for about one to four days, particularly about two days. Briefly, the RD1 (Table 1) comprised DMEM and F12 at about a 1:1 ratio, knockout serum replacement, MEM NEAA, sodium pyruvate, N-2 supplement, B-27 supplement, and ascorbic acid. In addition, the RD1 comprised a WNT pathway inhibitor (e.g., CKI-7), a BMP pathway inhibitor (e.g., LDN193189), a TGFβ pathway inhibitor (e.g., SB431542), and a MEK inhibitor (e.g., PD325901), and IGF-1. The concentration of the WNT pathway inhibitor, BMP pathway inhibitor and TGFβ pathway inhibitor was ten times higher in the RDM as compared to the RIM. Each day the media was aspirated and room temperature RD1 was added to the cells to produce differentiated retinal cells. In particular, the BMP inhibitor may be removed after the first few days, such as after 2 days, to enhance expression of VSX2 in the PRP cells. The RDM1 media may be replaced with RD2 (Table 1) which does not comprise the BMP inhibitor, such as LDN193189. The cells may be cultured in the RD2 for about five to ten days, such as about seven days.

To derive NRP cells, the cells were then cultured in Retinal Maturation Medium (RM1 or RM2) (Table 1) for about five days to differentiate the RPCs cells to NRPs. The RM1 comprised DMEM and F12 at about a 1:1 ratio, knockout serum replacement, MEM NEAA, sodium pyruvate, N-2 supplement, B-27 supplement and ascorbic acid. In addition, the RM1 comprised Nicotinamide, but was free of Activin A to prevent differentiation towards RPE cells. The RM1 media may further comprise a γ-secretase inhibitor, such as DAPT. The RM2 may further comprise a TGFβ inhibitor, such as SB431542, and/or bFGF. The medium was changed daily with room temperature RM1. The RPCs were then cultured in photoreceptor precursor induction medium (FDSC) medium from Days 15-18 to produce NRP cells. To analyze the NRP cells, they were thawed into post-thaw medium and assayed for expression of PAX6 and VSX2 (FIG. 14). The NRP cells were found to be almost 100% positive for PAX6, about 90% positive for PMEL17, and about 80% positive for VSX2 (FIG. 14).

Example 3—Differentiation of RPCs to PRP Cells

Figures 4A, 4B, 4C:
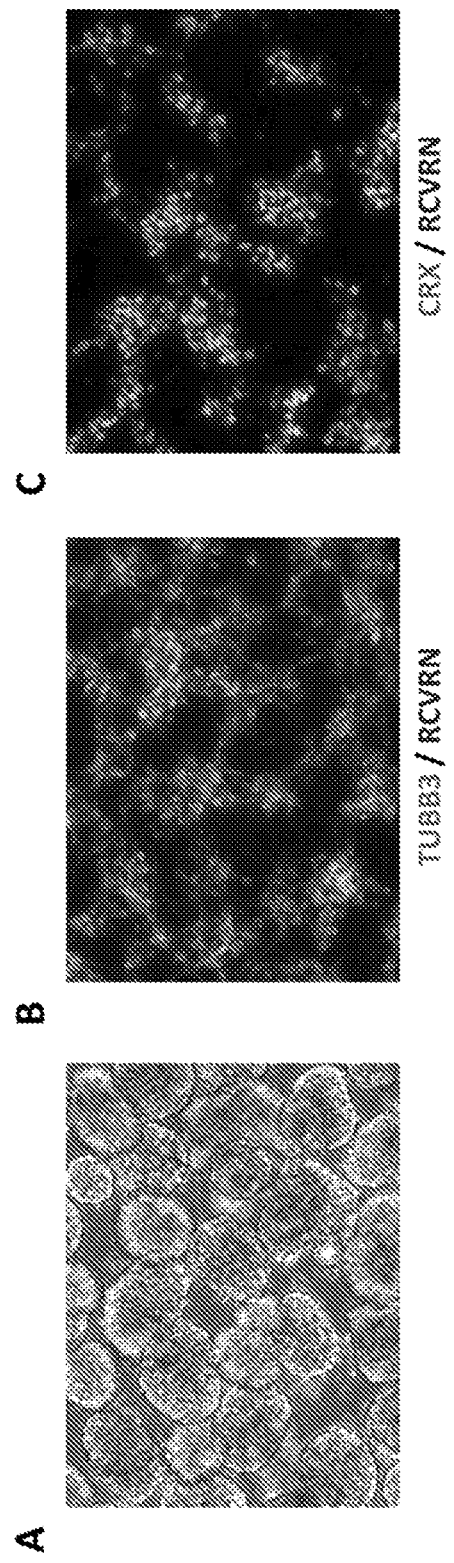
FIGS. 4A-4D: 2-D PRP Characterization.
Figures 1, 4D:
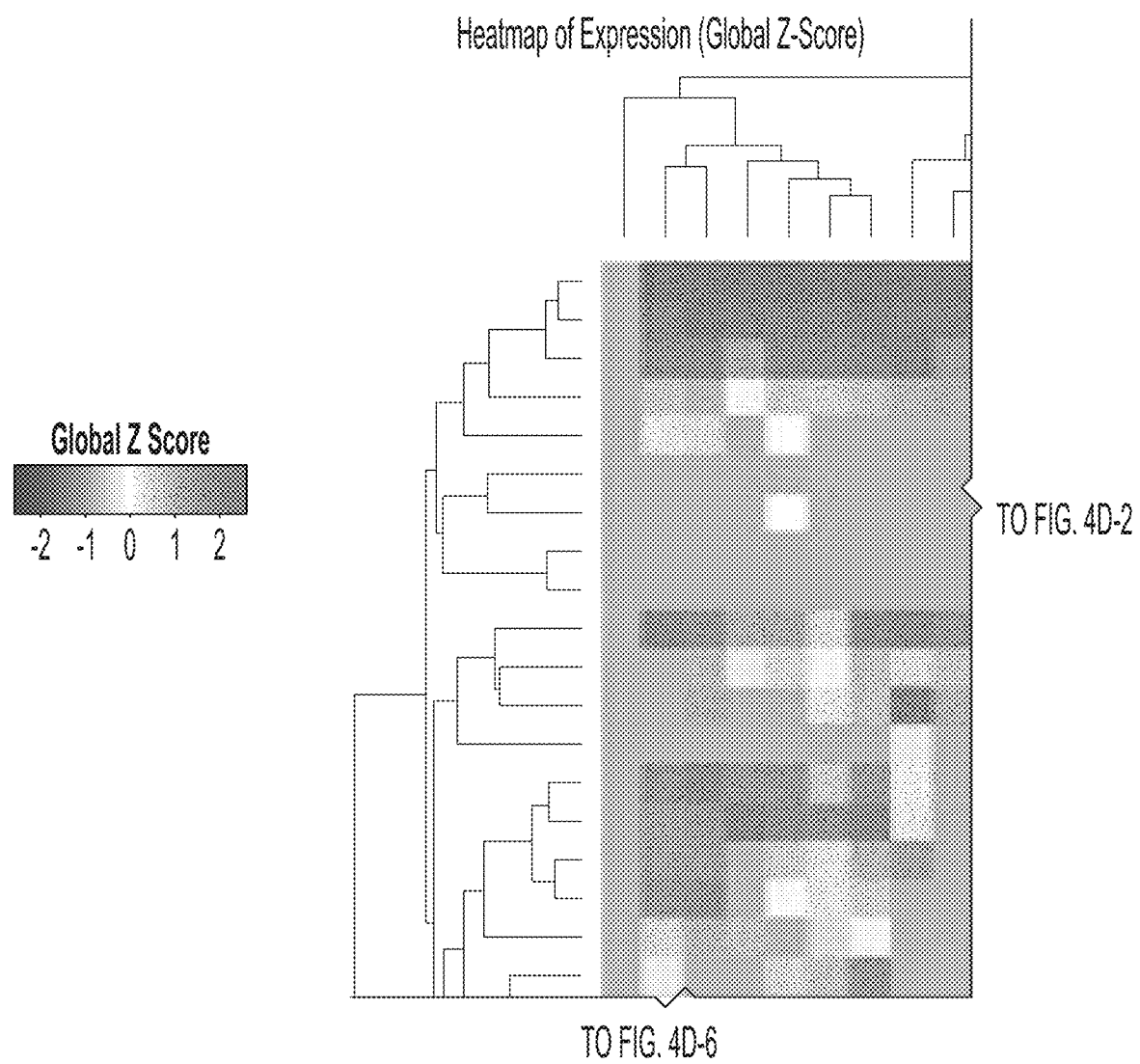
Figures 2, 4D:
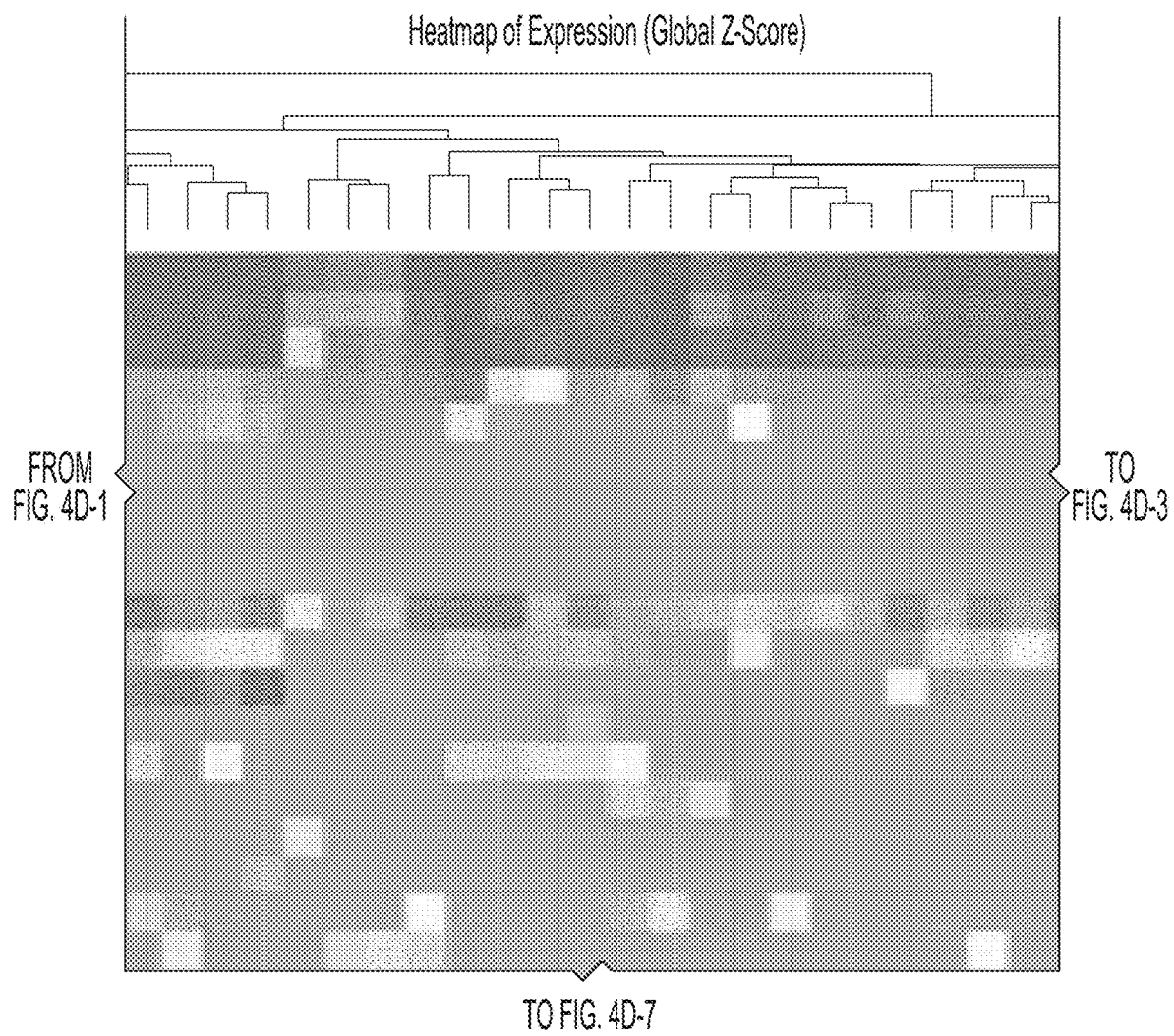

To complete the differentiation process to PRP cells, the RPC cells of Example 2 were cultured in FDSC medium (Table 1). Briefly, the FDSC Medium comprises DMEM and F12 at about a 1:1 ratio, knockout serum replacement, MEM NEAA, sodium pyruvate, N-2 supplement, B-27 supplement and ascorbic acid. In addition, the FDSC Medium may comprise basic FGF, DAPT, SB431542, and CKI-7 to differentiate the NRPs towards PRP cells. The cells were cultured in the FDSC medium for about ten to twenty days, particularly fifteen days. The PRP cells were analyzed for expression of the markers Tuj1/Nestin and RCVRN (FIGS. 4A-4C).

At this stage, the derived PRP cells can be dissociated using TRYPLE™ and cryopreserved in xenofree CS10 medium. Alternatively, the derived PRP cells can be cultured in medium comprising ROCK inhibitor or blebbistatin to promote aggregate formation for one to five days, such as three days, to promote better cell survival and transplantation. Thus, the presently disclosed methods provide PRP cells from pluripotent cells that can be consistently reproduced at a large scale for clinical applications.

Example 4—Production of Optic Vesicles

Figures 12A, 12B:
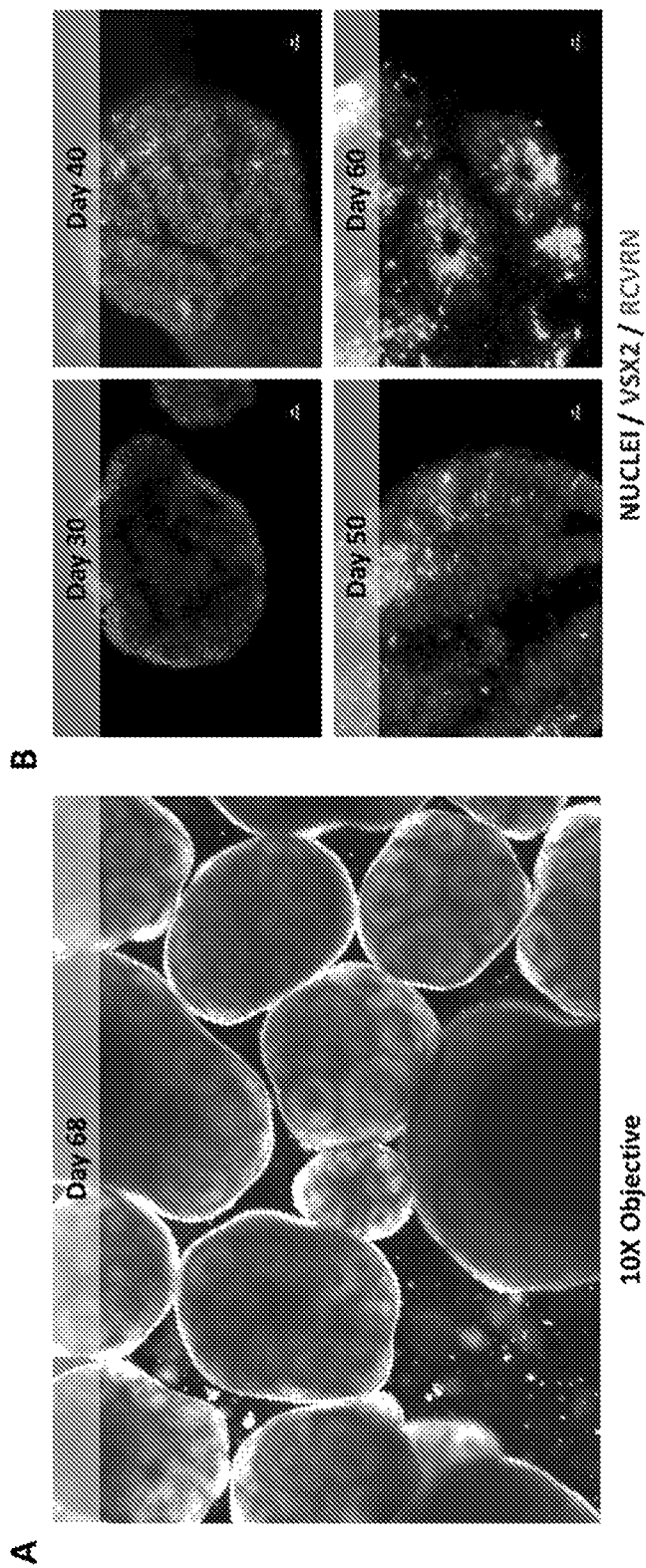
FIGS. 12A-12D: Hybrid OV Morphology and Characterization.
Figure 12C:
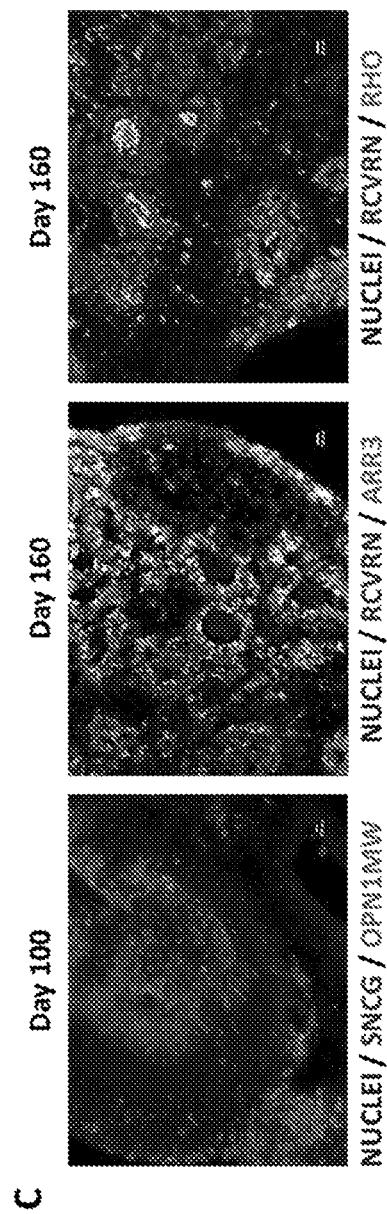
Figure 12D:
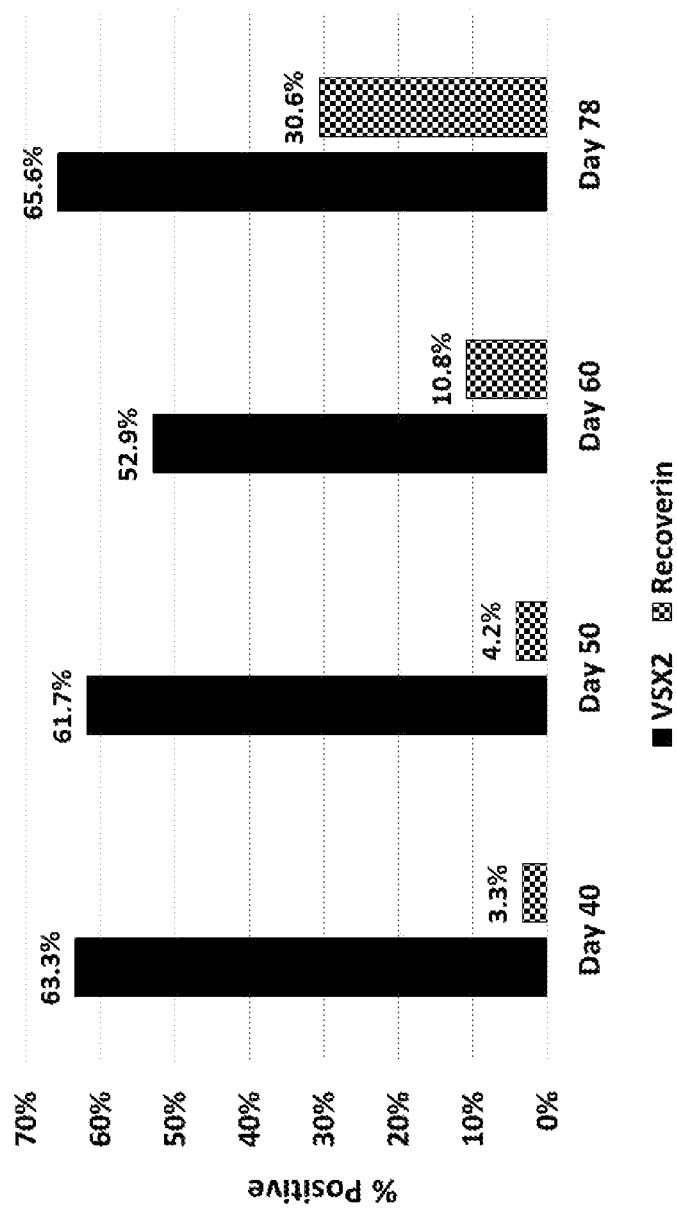
Figure 13:
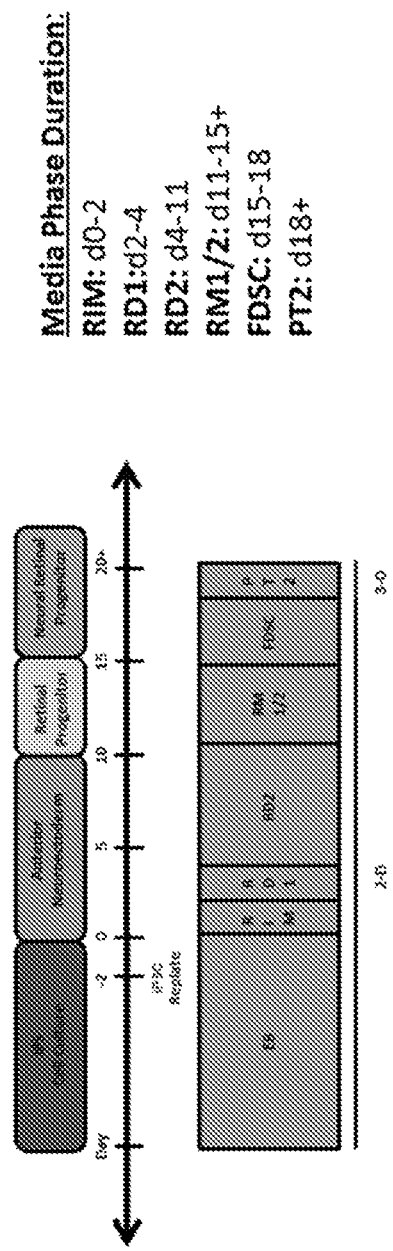
FIG. 13: Schematic of the 2-D NRP differentiation process.
Figures 1, 15A:
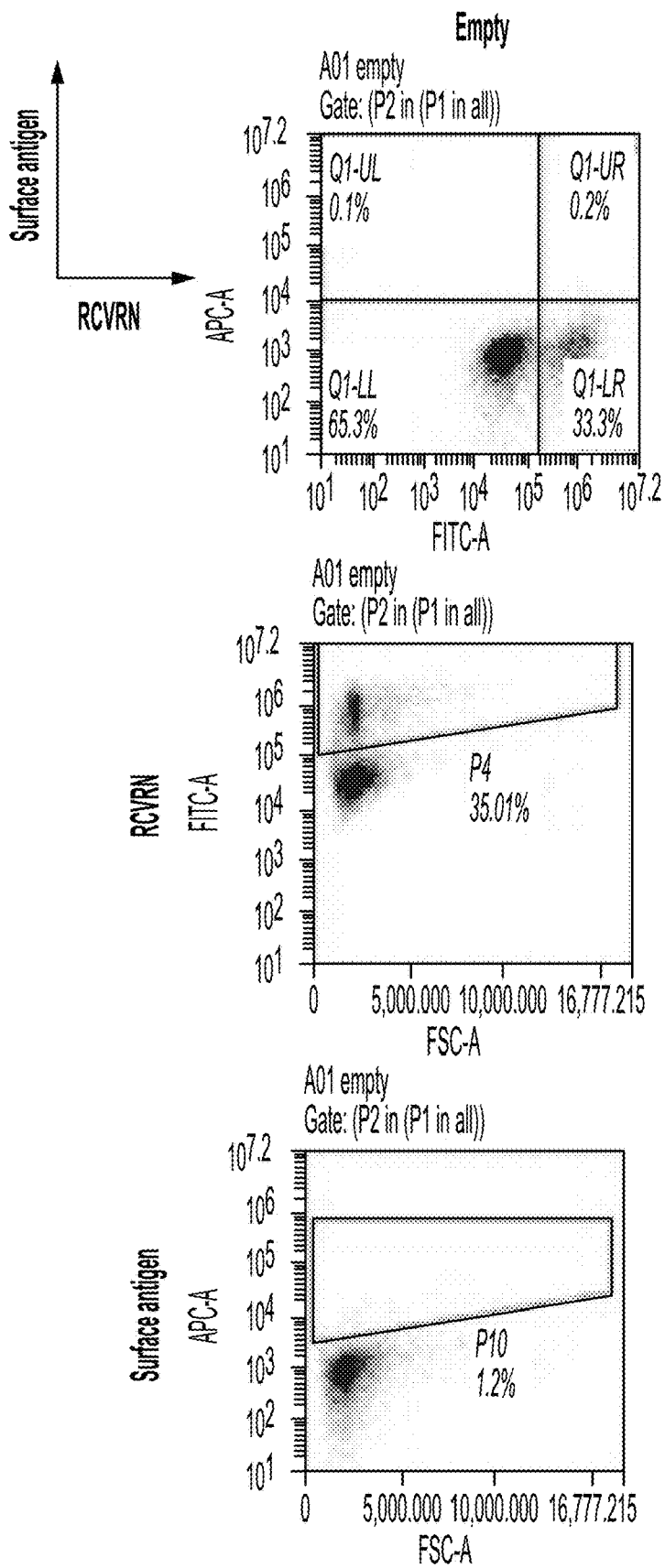
FIGS. 15A-15B: Flow analyses of surface antigens and recoverin co-expression corresponding to Table 4 was determined using a quadrant flow plot following dual-labeling with recoverin and the antibody against the respective surface antigen. Additionally, percent population of cells expressing only recoverin (in FITC, x-axis) or only the surface antigen (in APC, y-axis) was evaluated. All plots were gated against unstained (empty) cells and the corresponding isotype control (REA IgG1, MsIgG1, Ms IgG2a, MsIgG2b, MsIgM).
Figures 2, 15A:
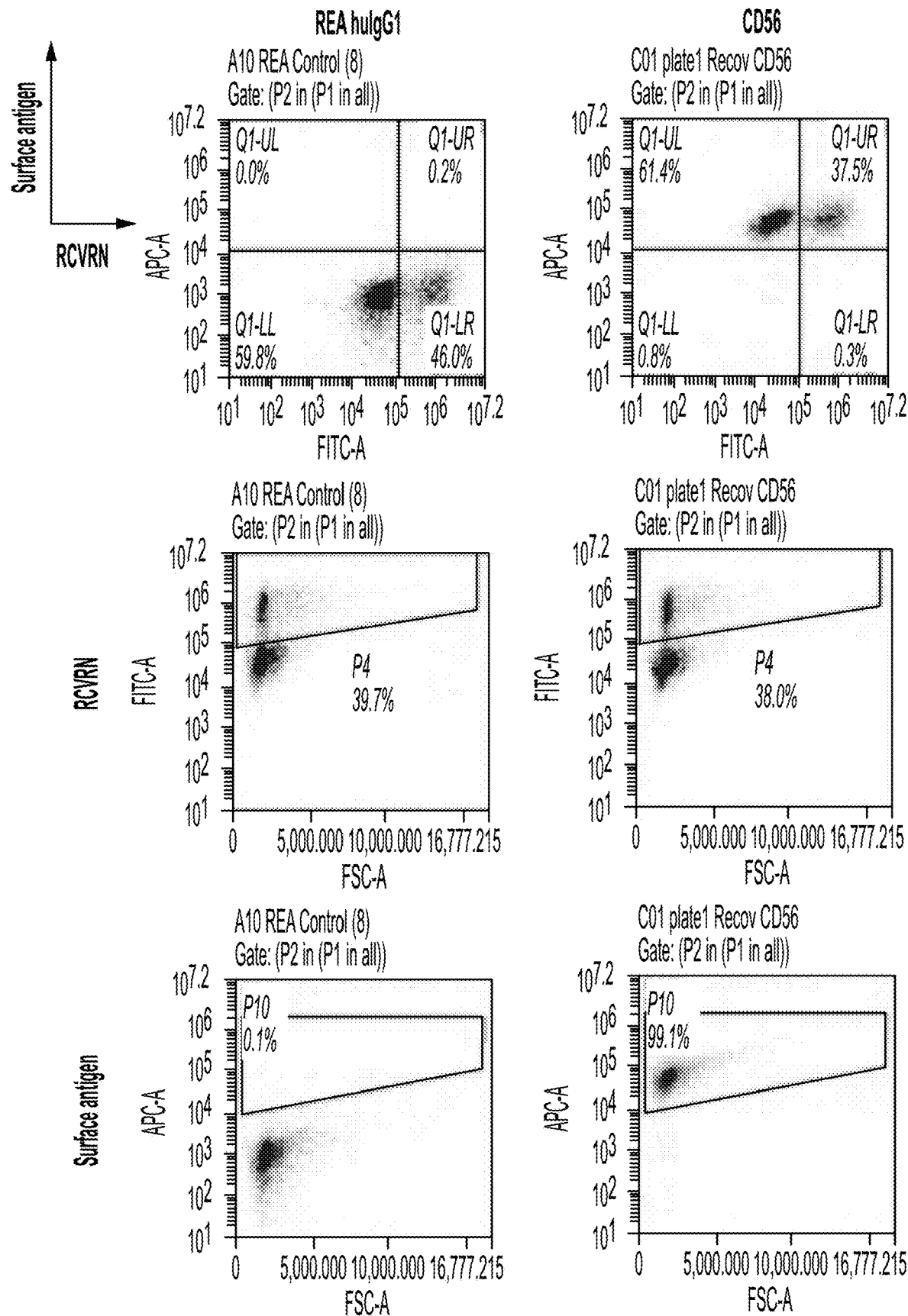
Figures 3, 15A:
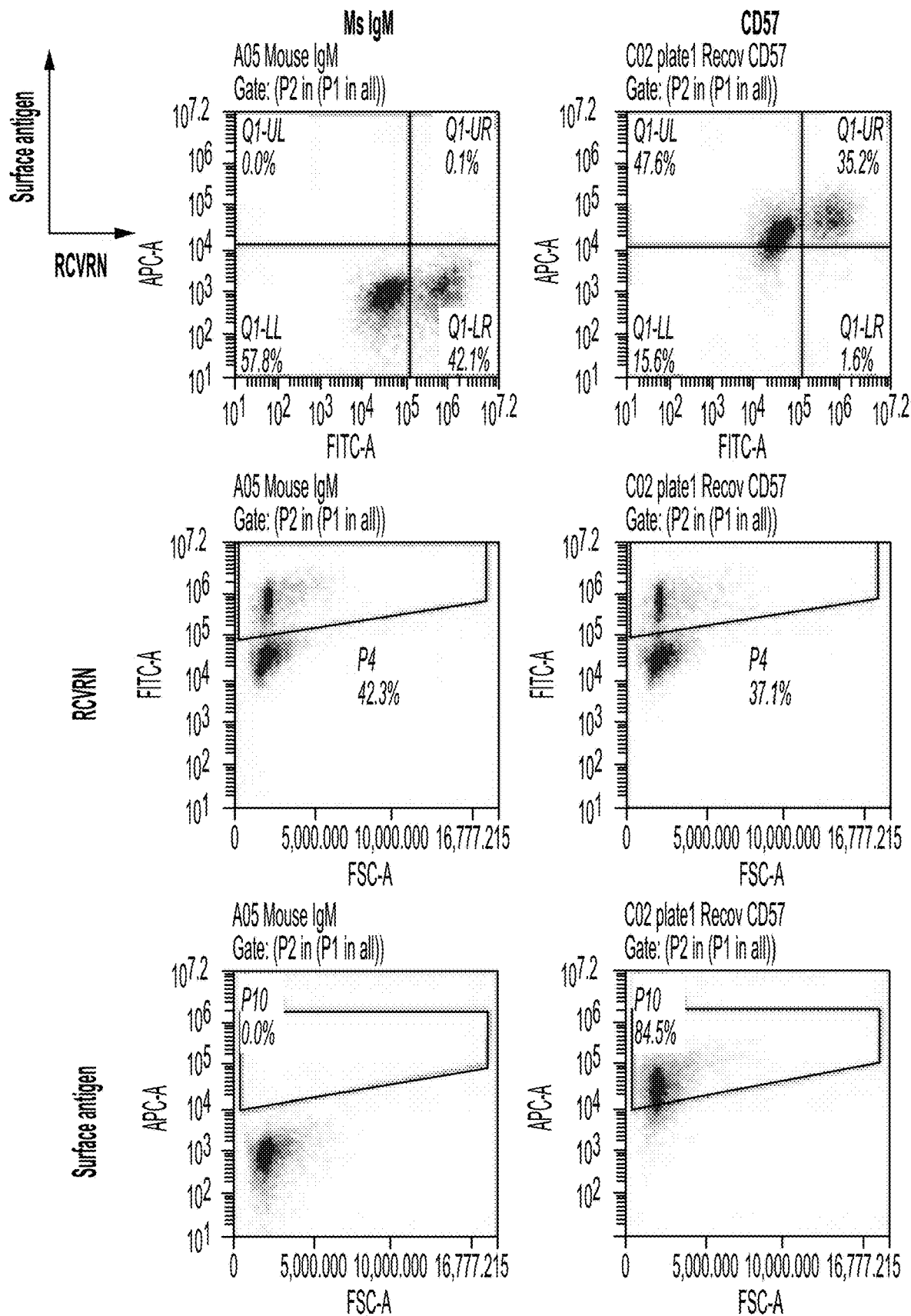
Figures 4, 15A:
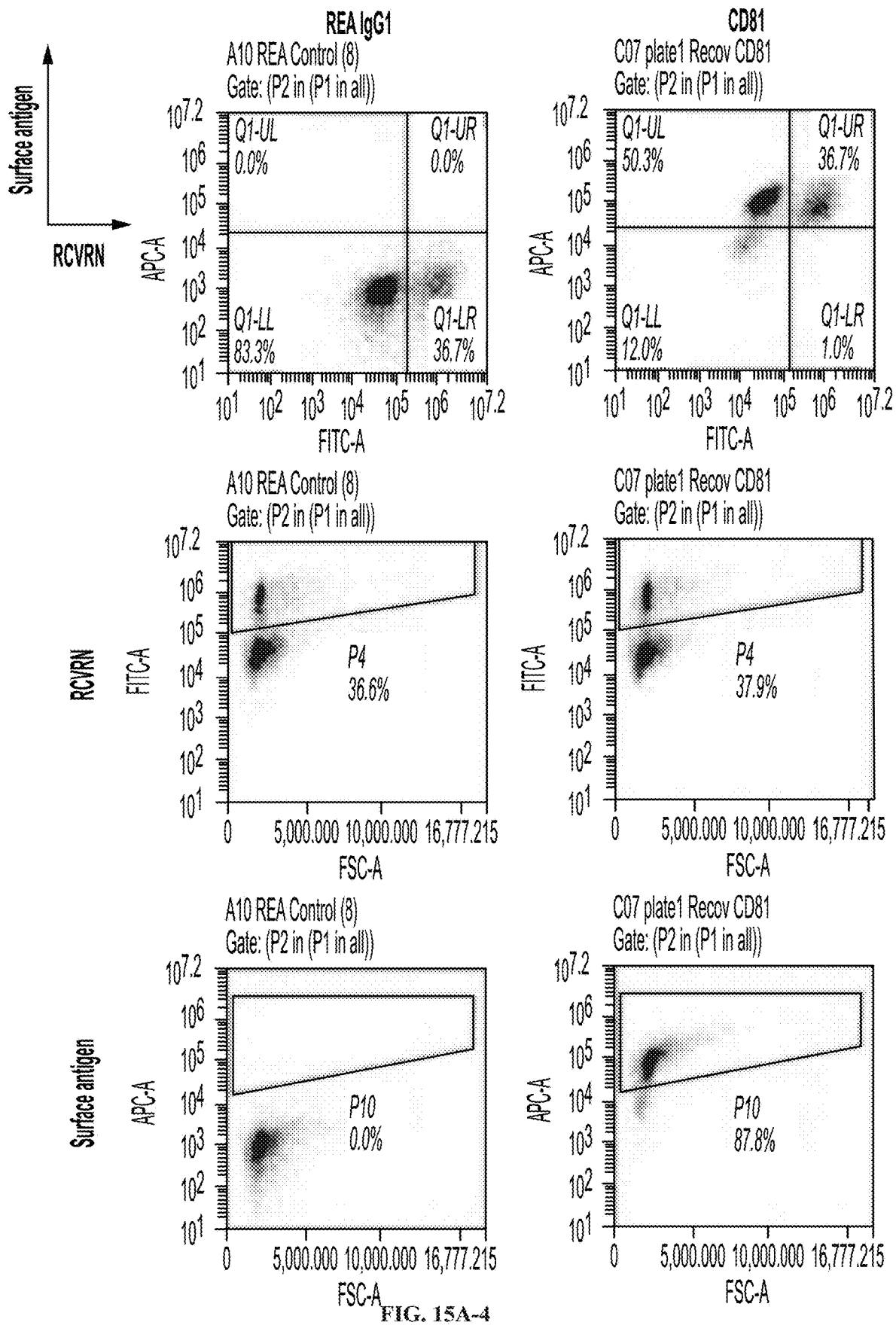
Figures 5, 15A:
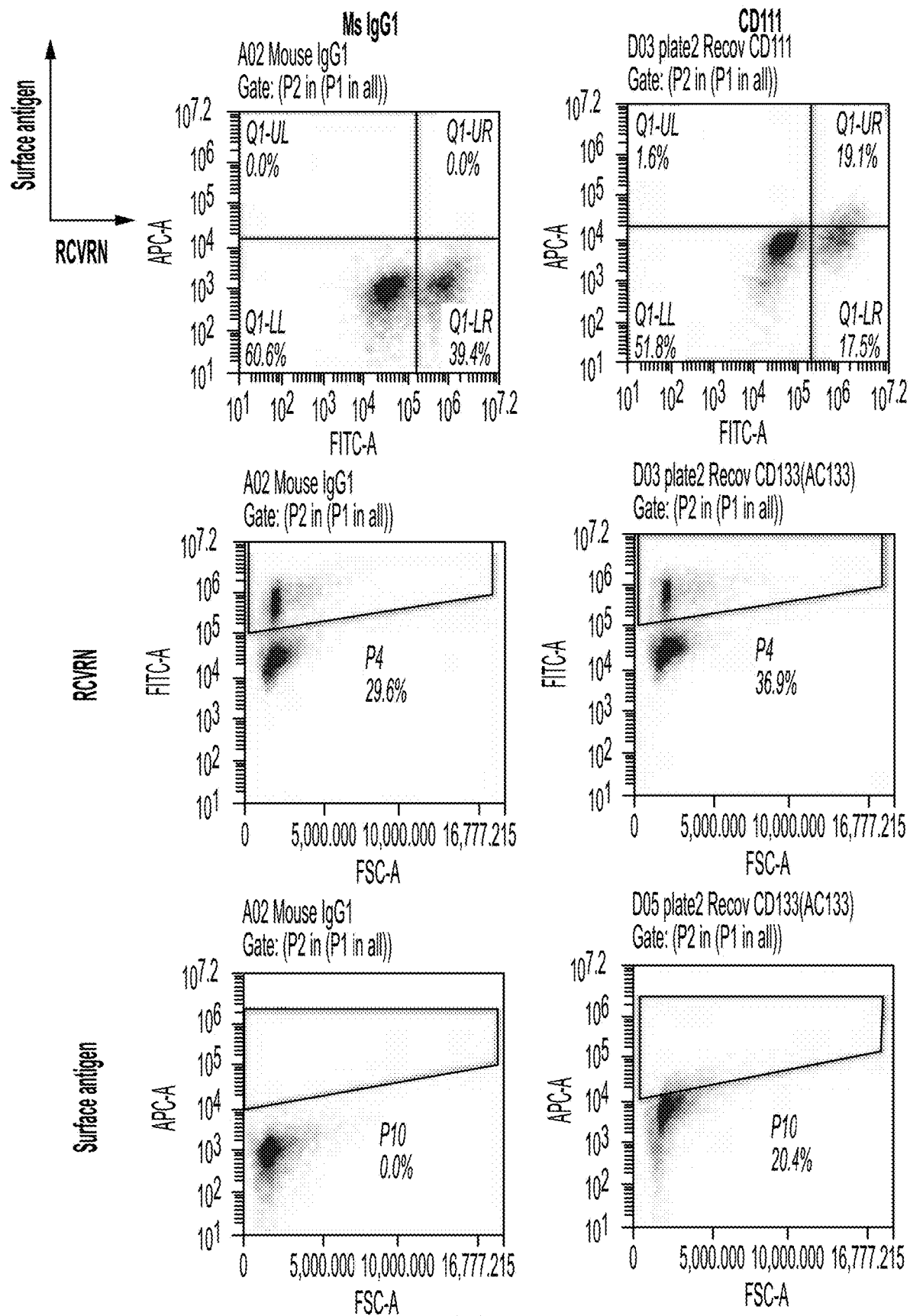
Figures 6, 15A:
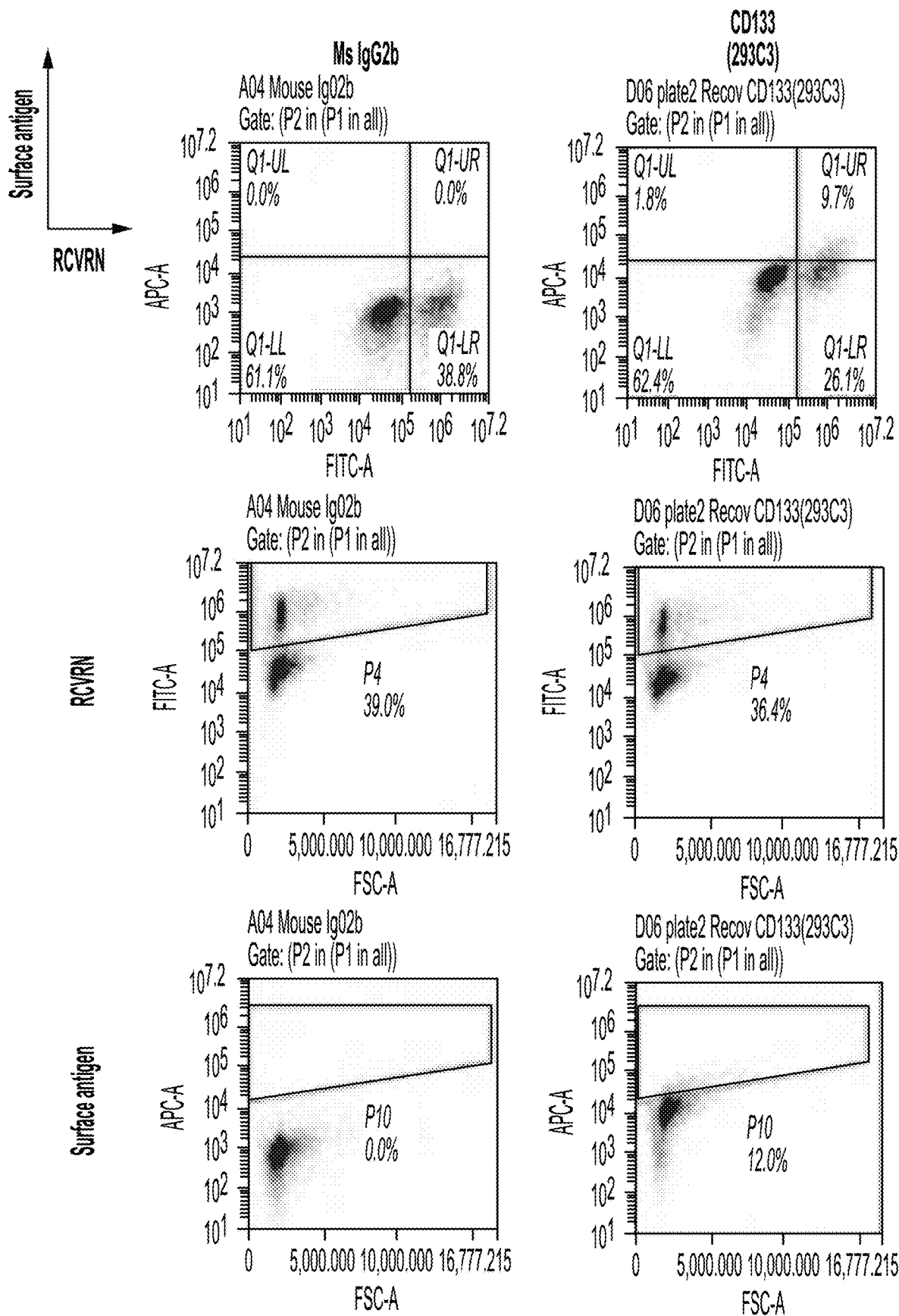
Figures 7, 15A:
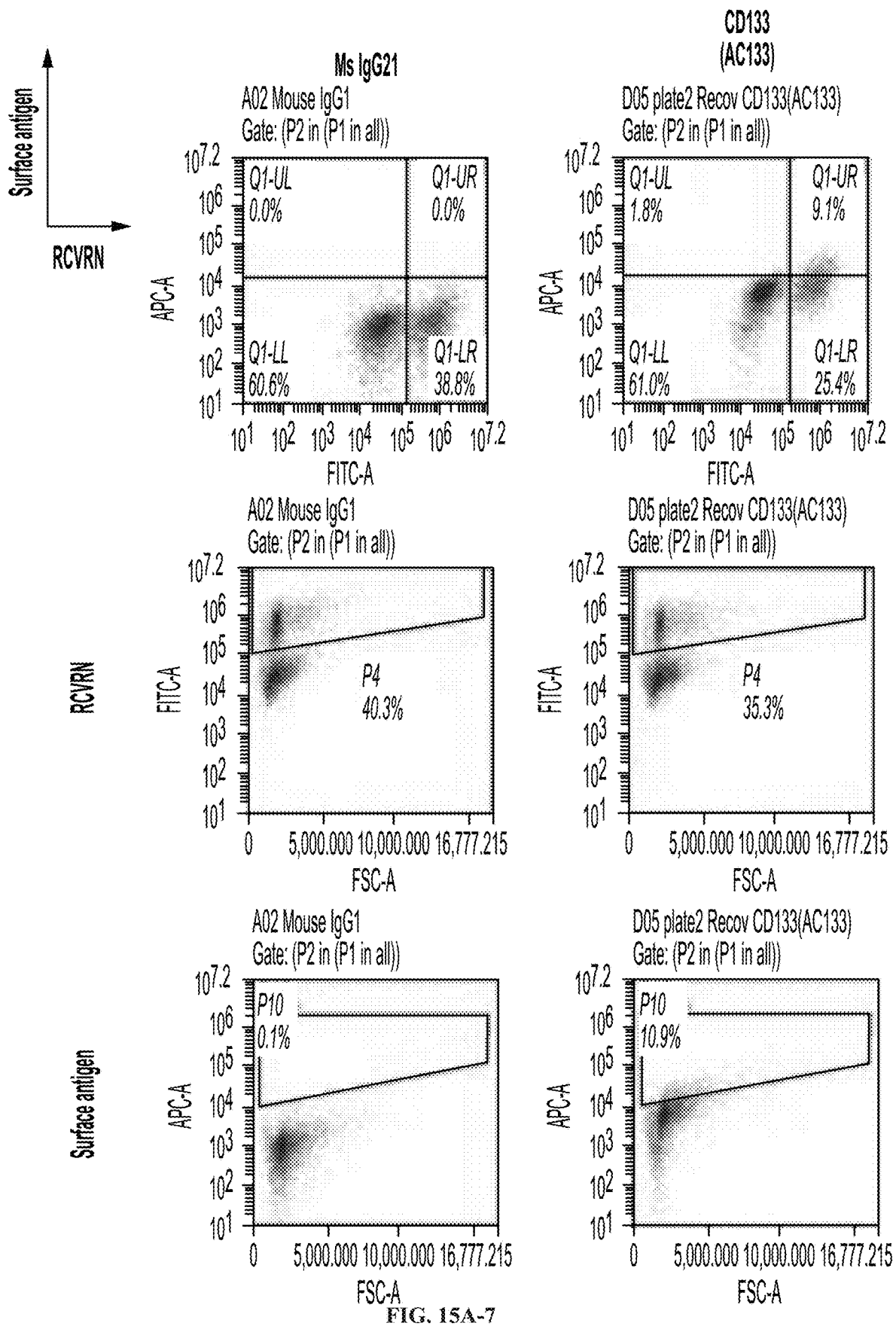
Figures 8, 15A:
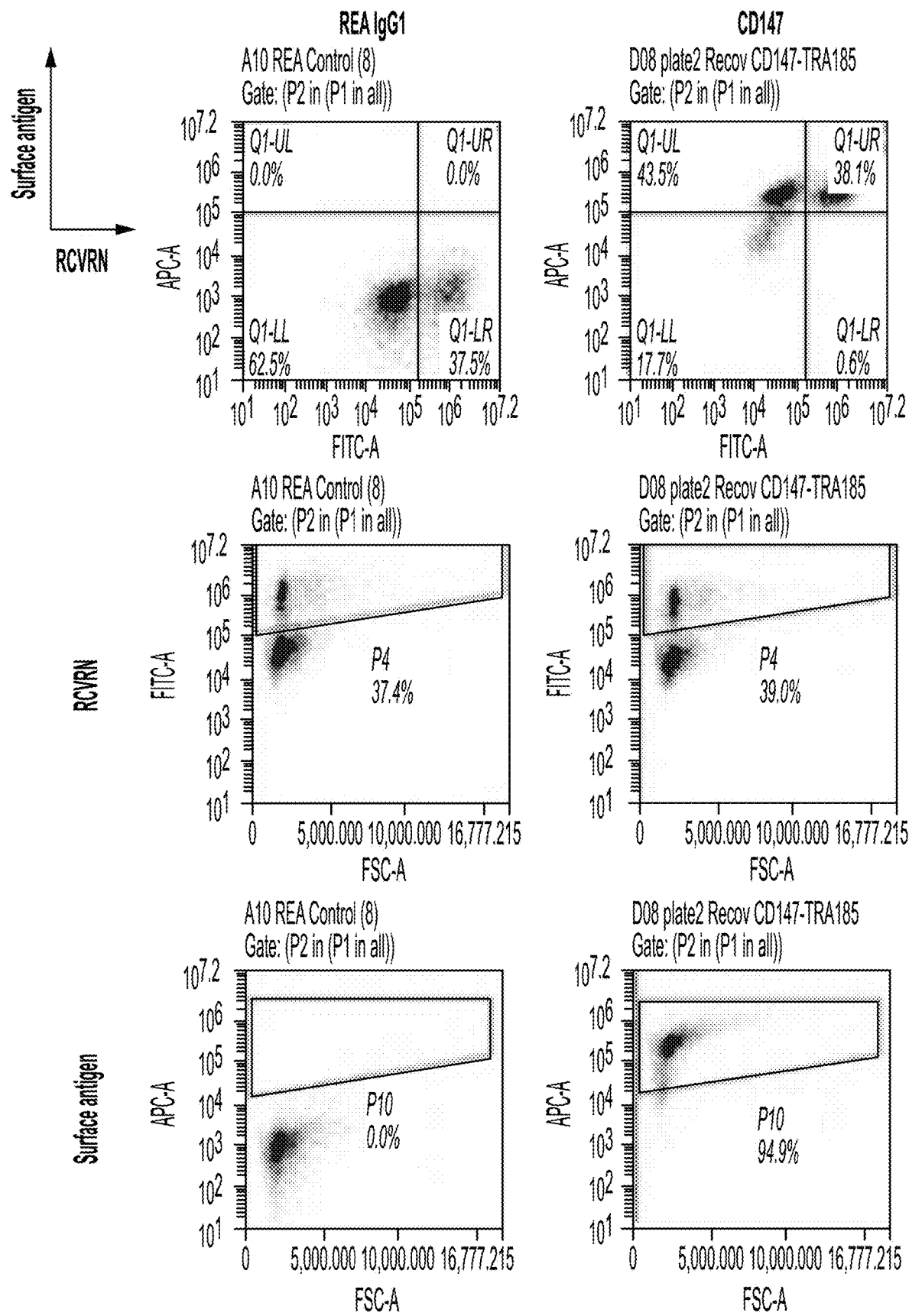
Figures 9, 15A:
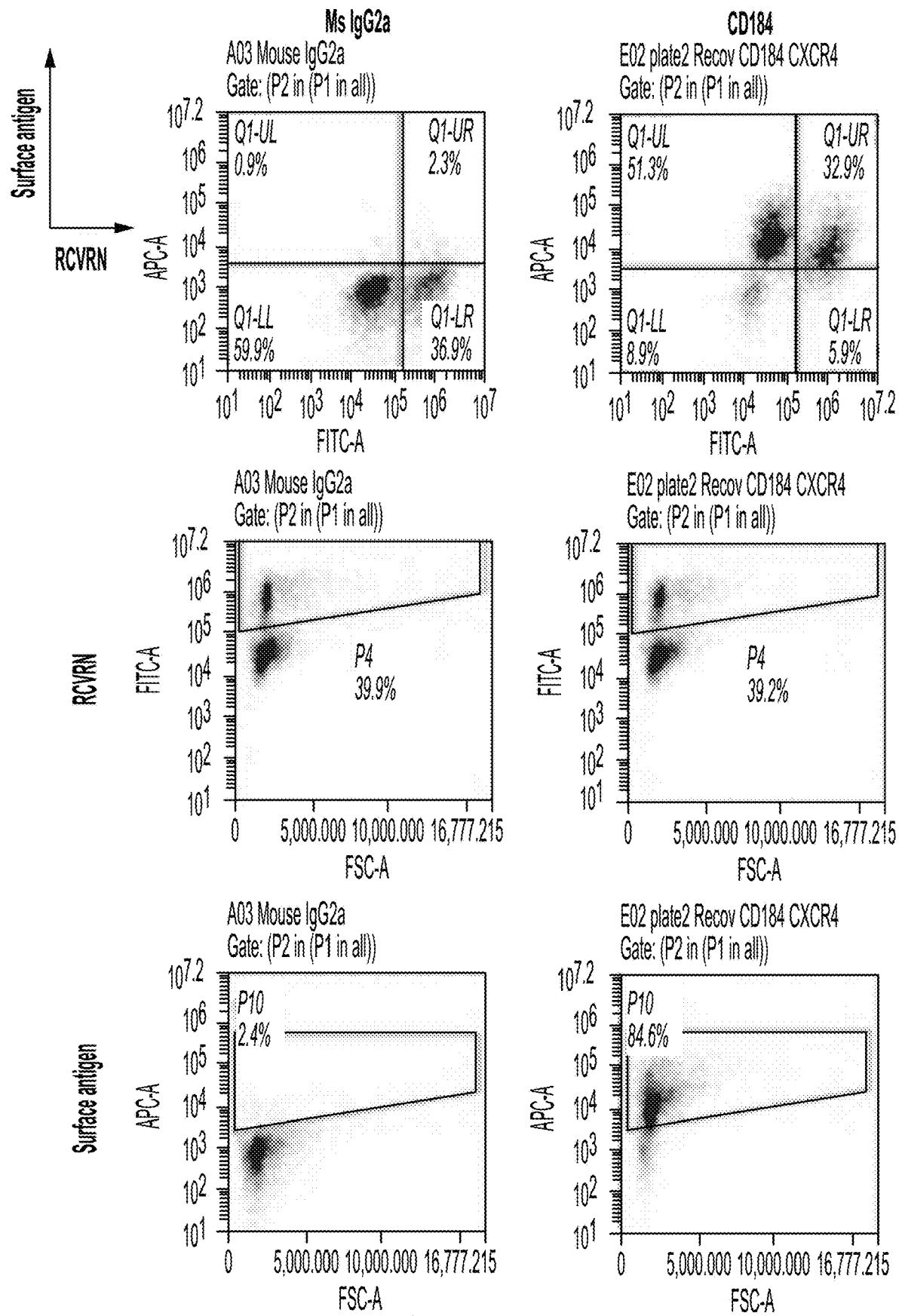
Figures 1, 15B:
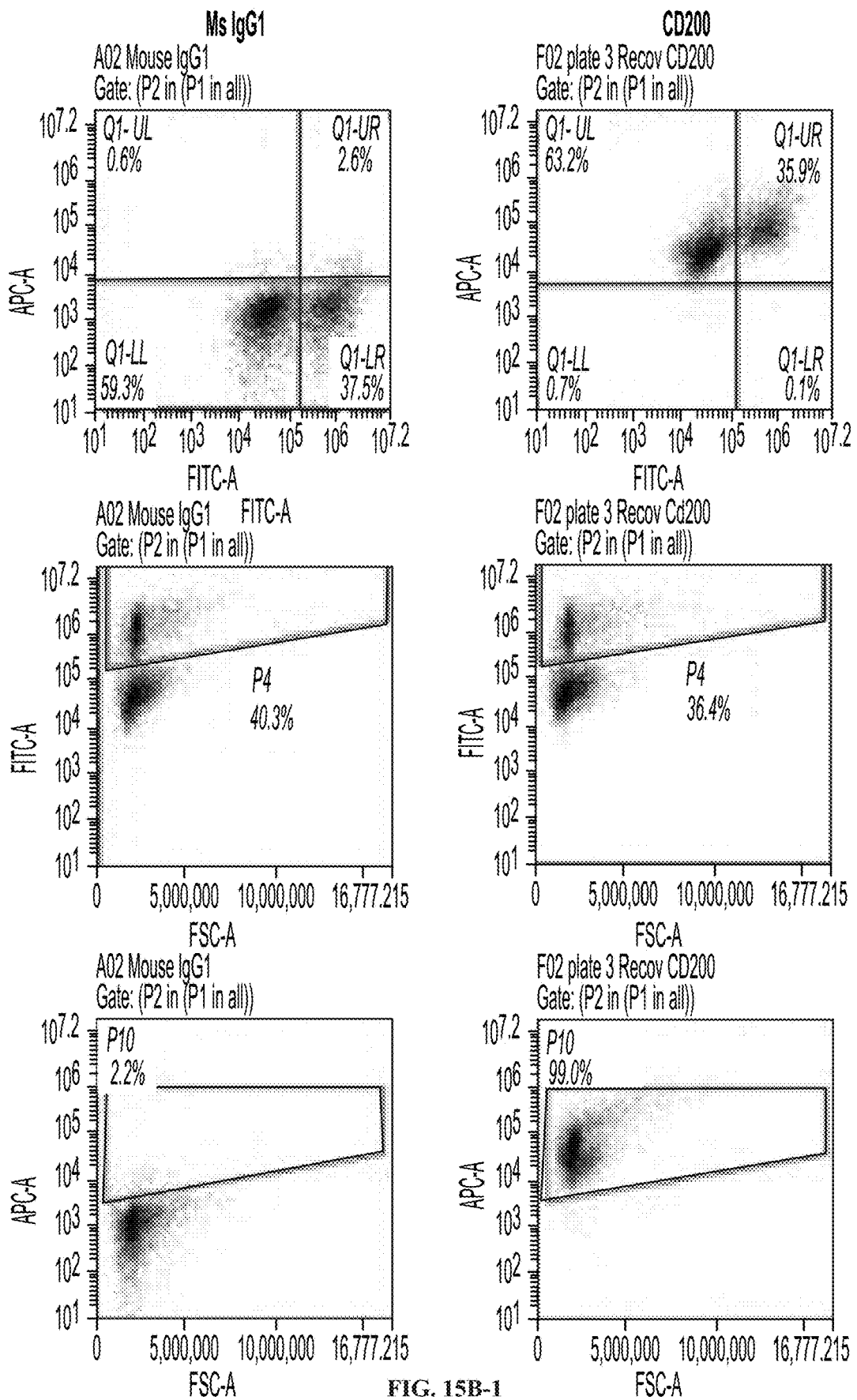
Figures 2, 15B:
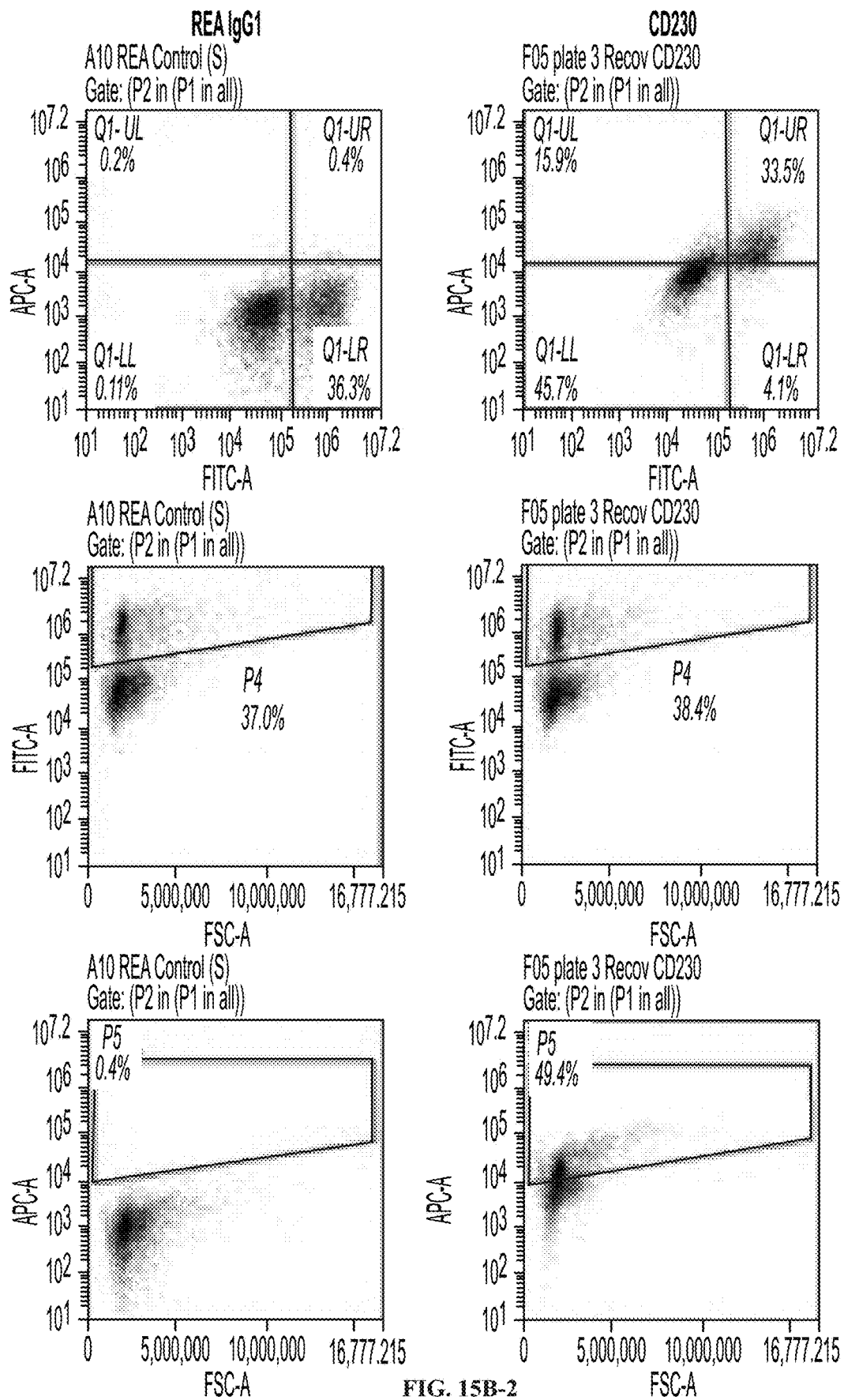
Figures 3, 15B:
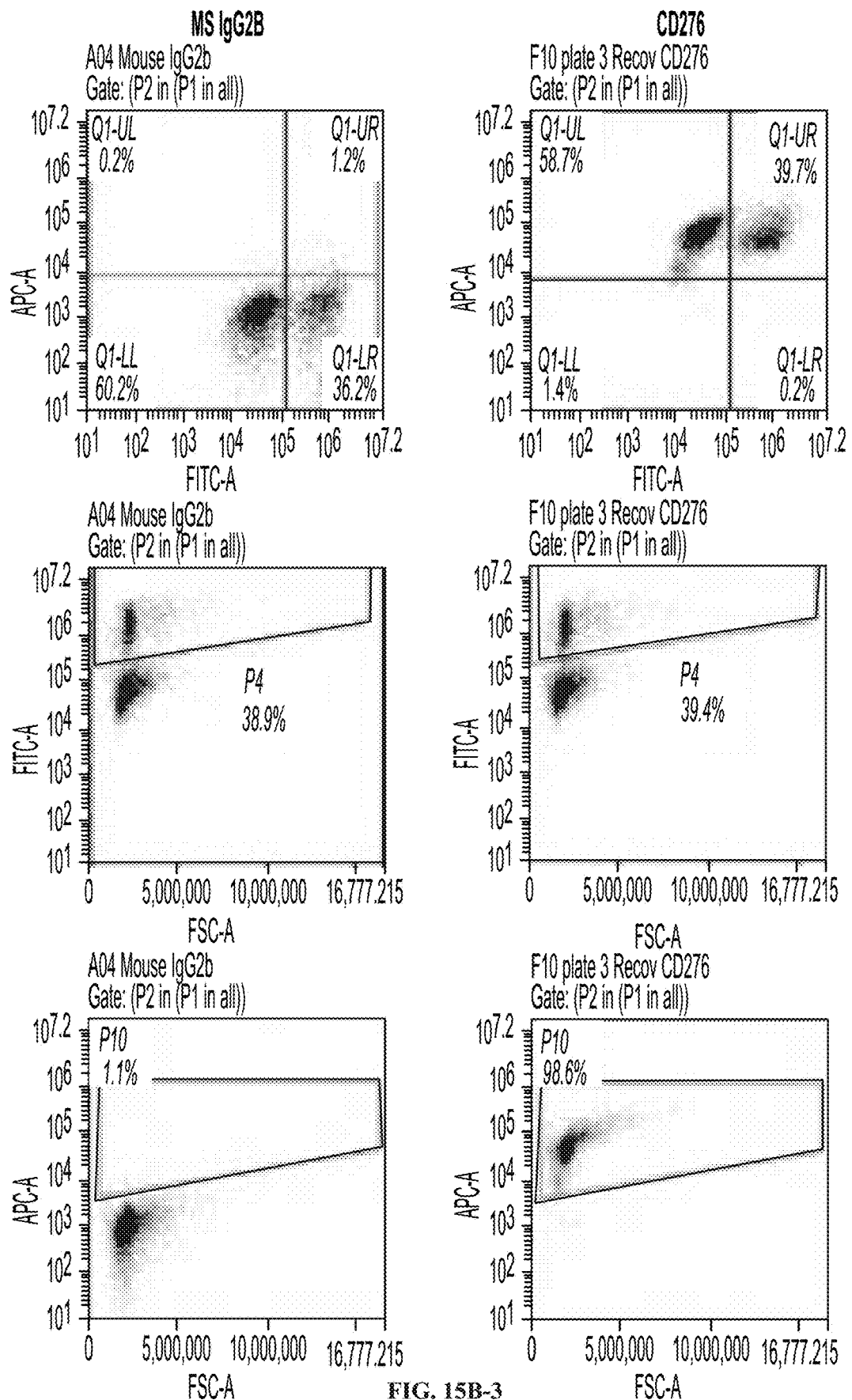
Figures 4, 15B:
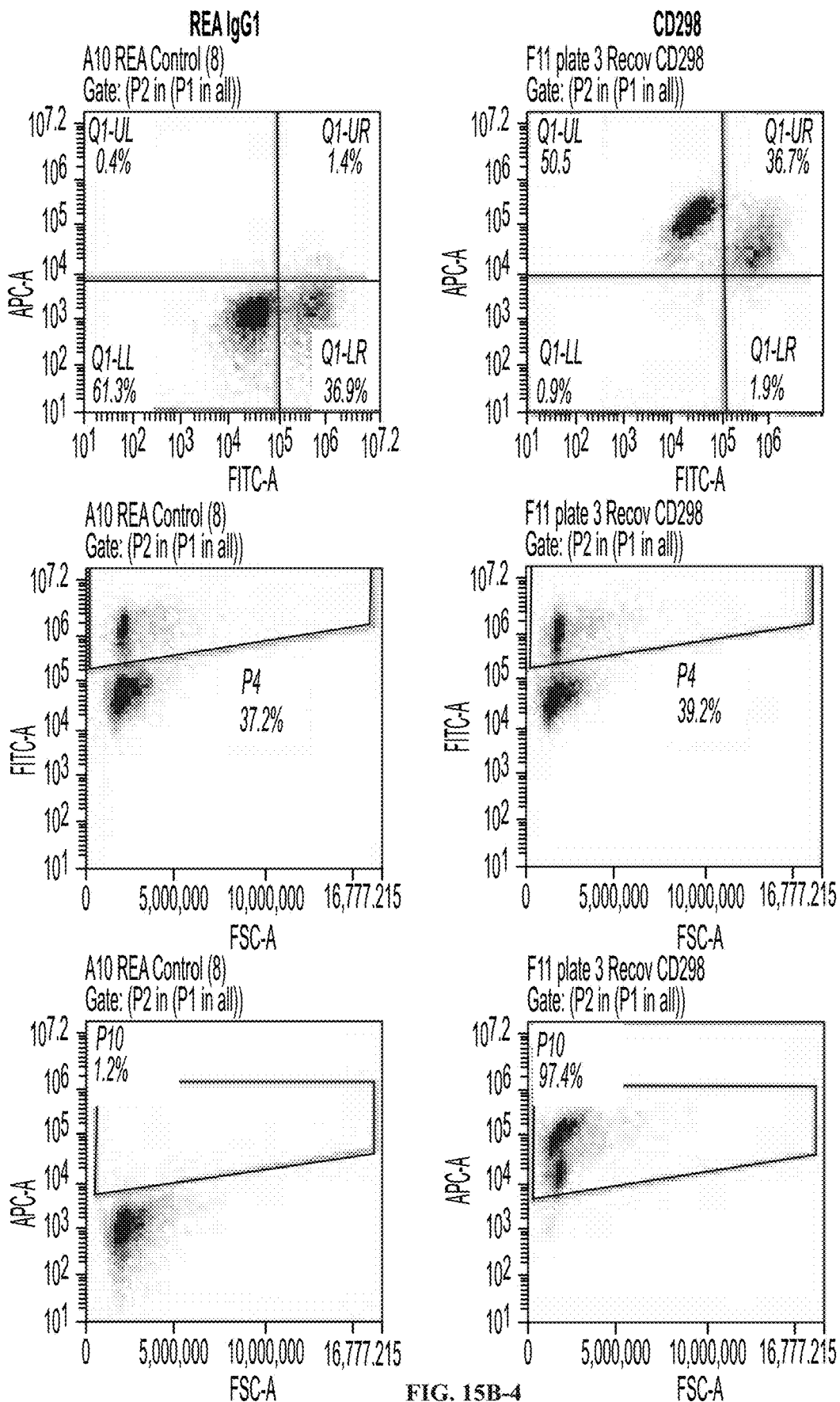
Figures 5, 15B:
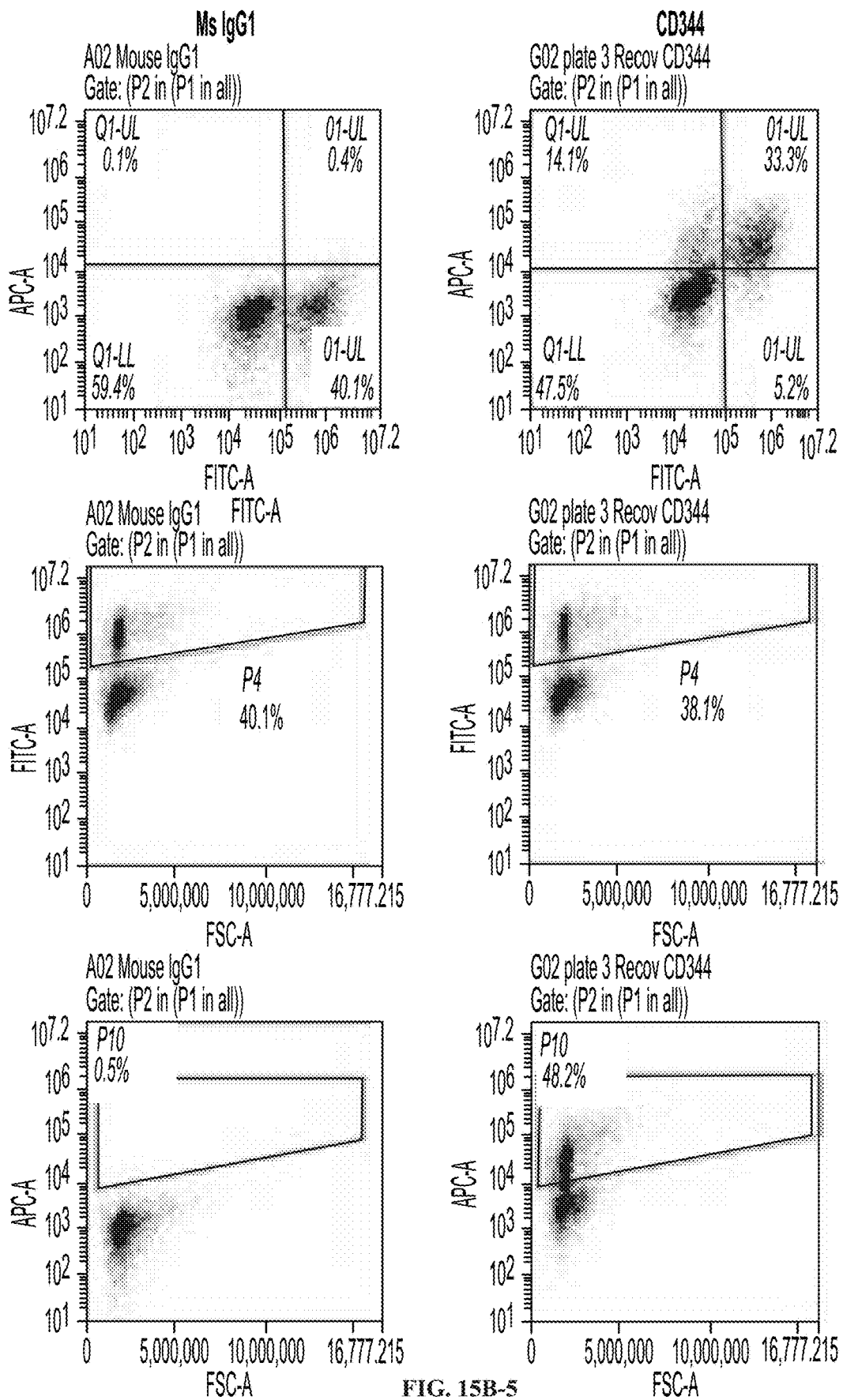
Figures 6, 15B:
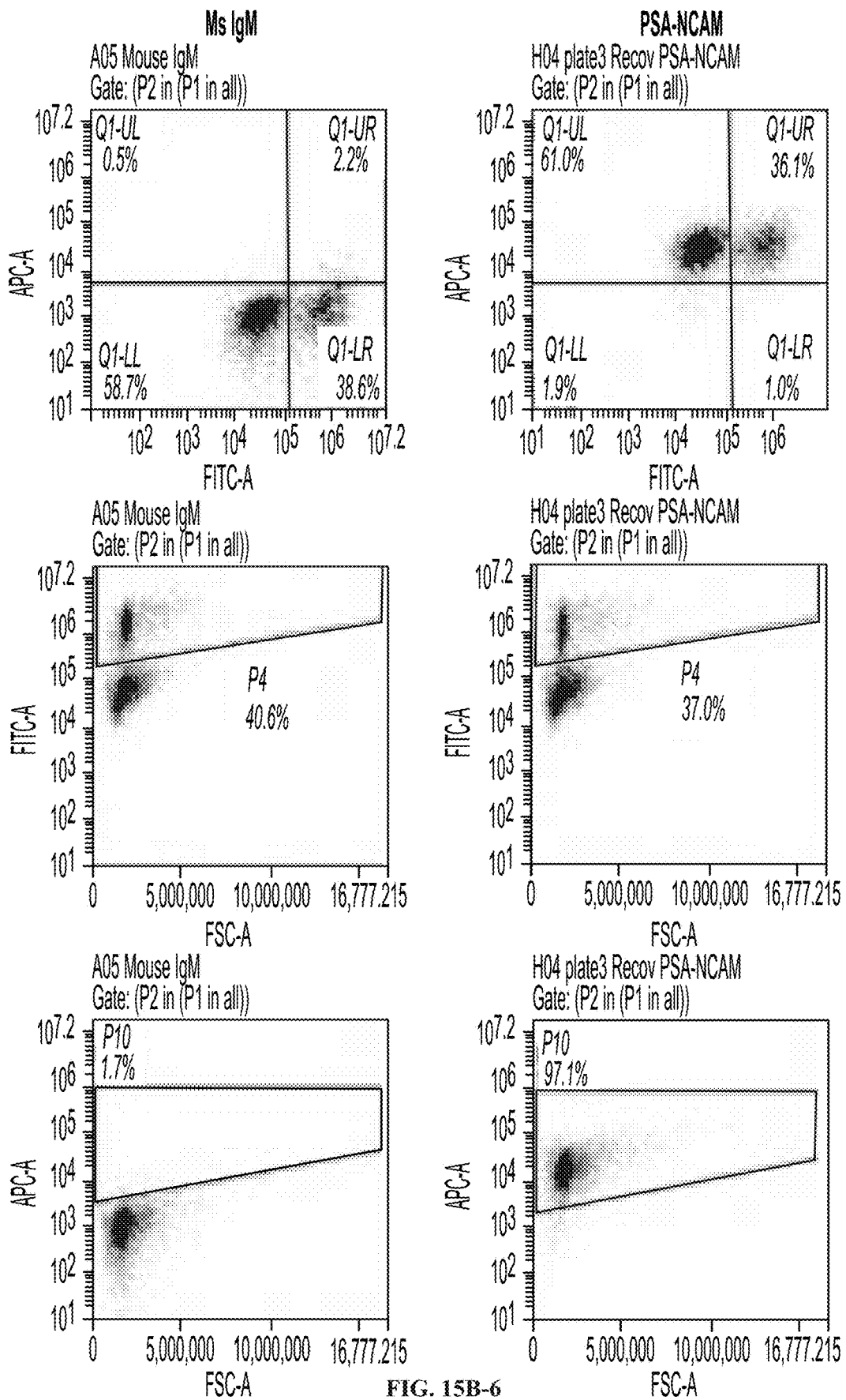
Figures 7, 15B:
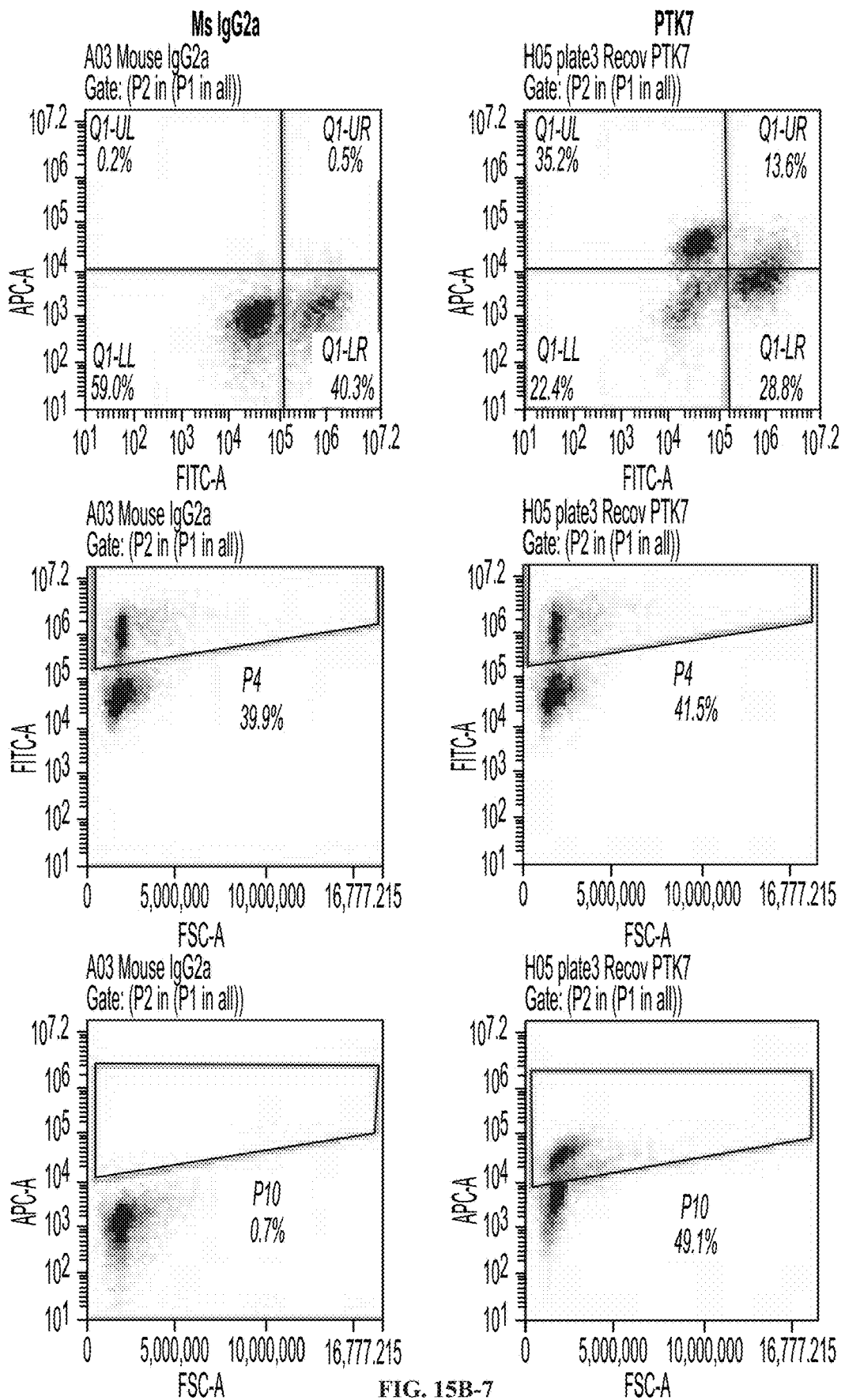

The RPC cells of Example 2 were cultured as aggregates in RM1 or RM2 media for an extended duration to produce optic vesicles. Blebbistatin was used to promote aggregate formation. The RM1 media comprised DMEM/F12, Knock-Out serum replacement, sodium pyruvate, ascorbic acid, and nicotinamide. The optic vesicles were evaluated for marker expression at Day 30, Day 40, Day 50, and Day 60. There was an increase in RCVRN expression from 3.3% at Day 40 to over 30% at Day 78 (FIG. 12D).

Example 5—Alternative Method for Production of PRP Cells

Figures 3, 4D:
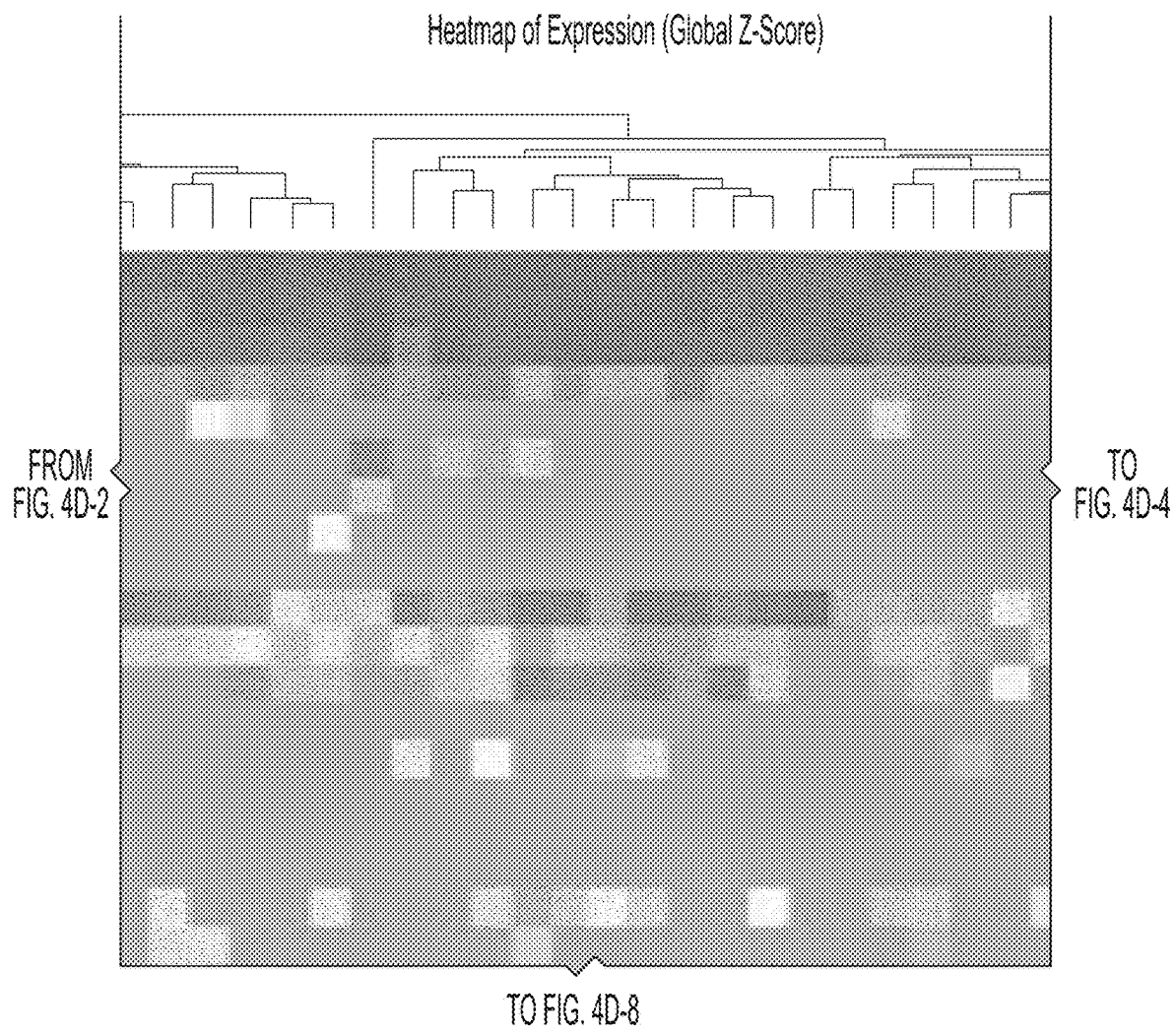
Figures 4, 4D:
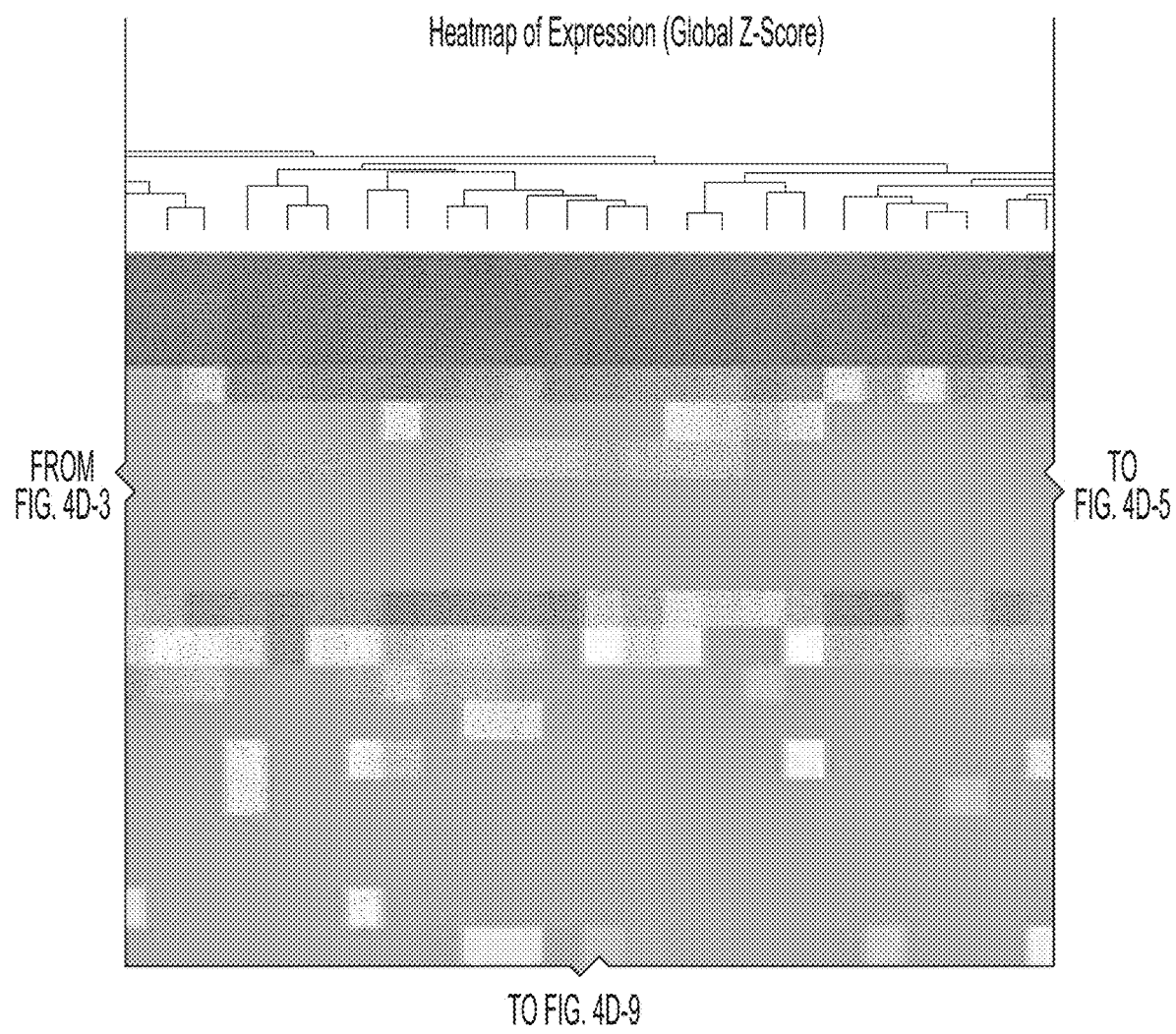
Figures 4, 4D, 5:
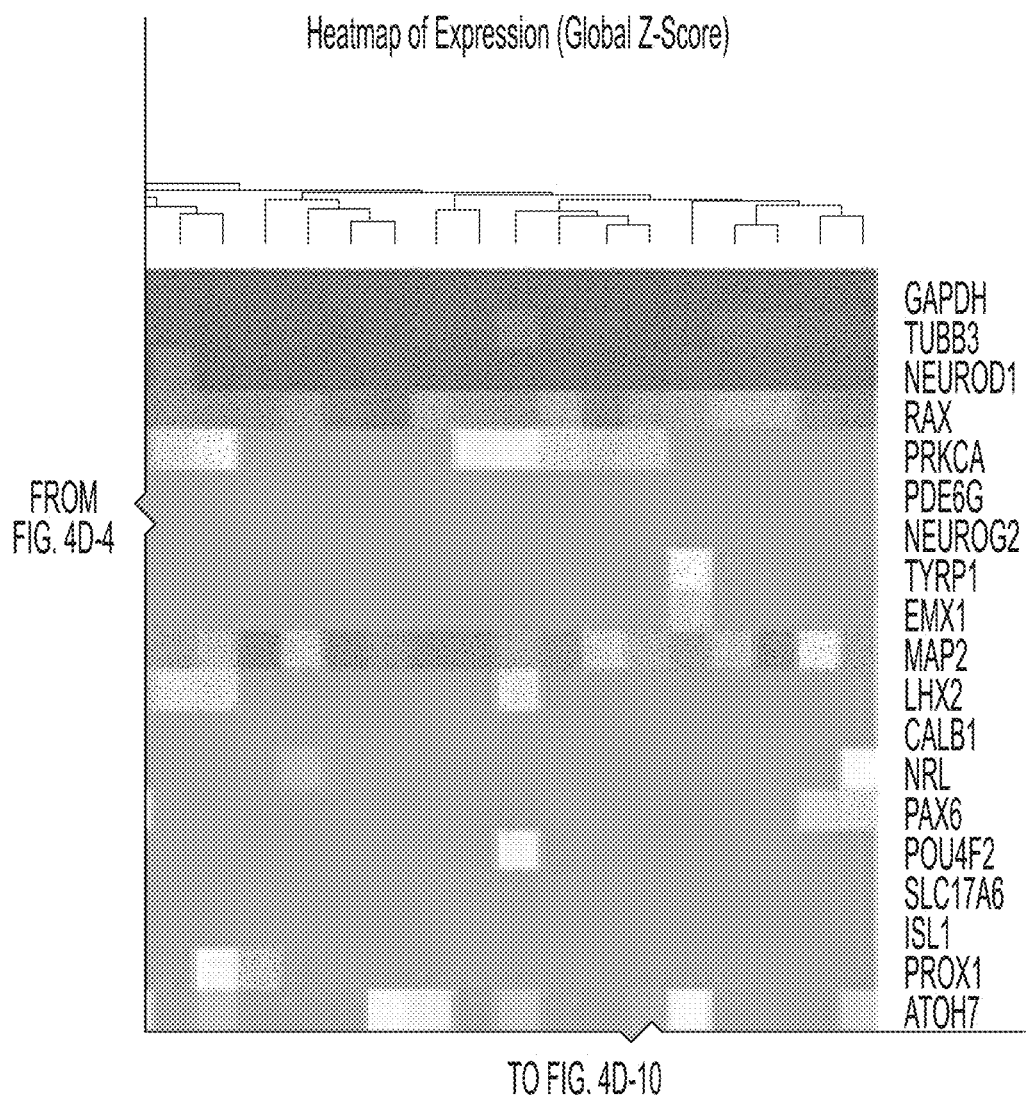
FIG. 5: Schematic of the Hybrid PRP differentiation process.
Figures 4, 4D, 5, 6:
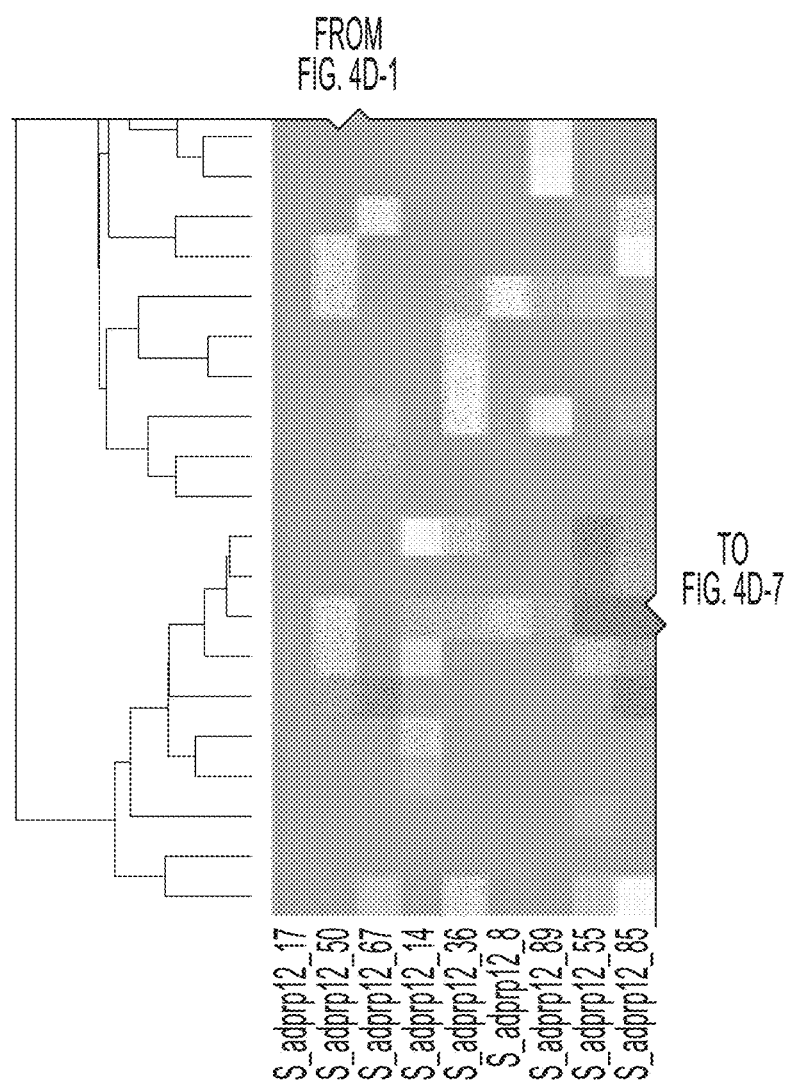
FIG. 6: Input iPSC Density Optimization. Flow cytometry analysis of day 15 Hybrid PRP differentiation for Pax6 and Vsx2 with input densities ranging from $1 \times 10^4$ (10K) to $1 \times 10^6$ (1000K) cells per well of a 6 well plate.
Figures 4, 4D, 5, 6, 7:
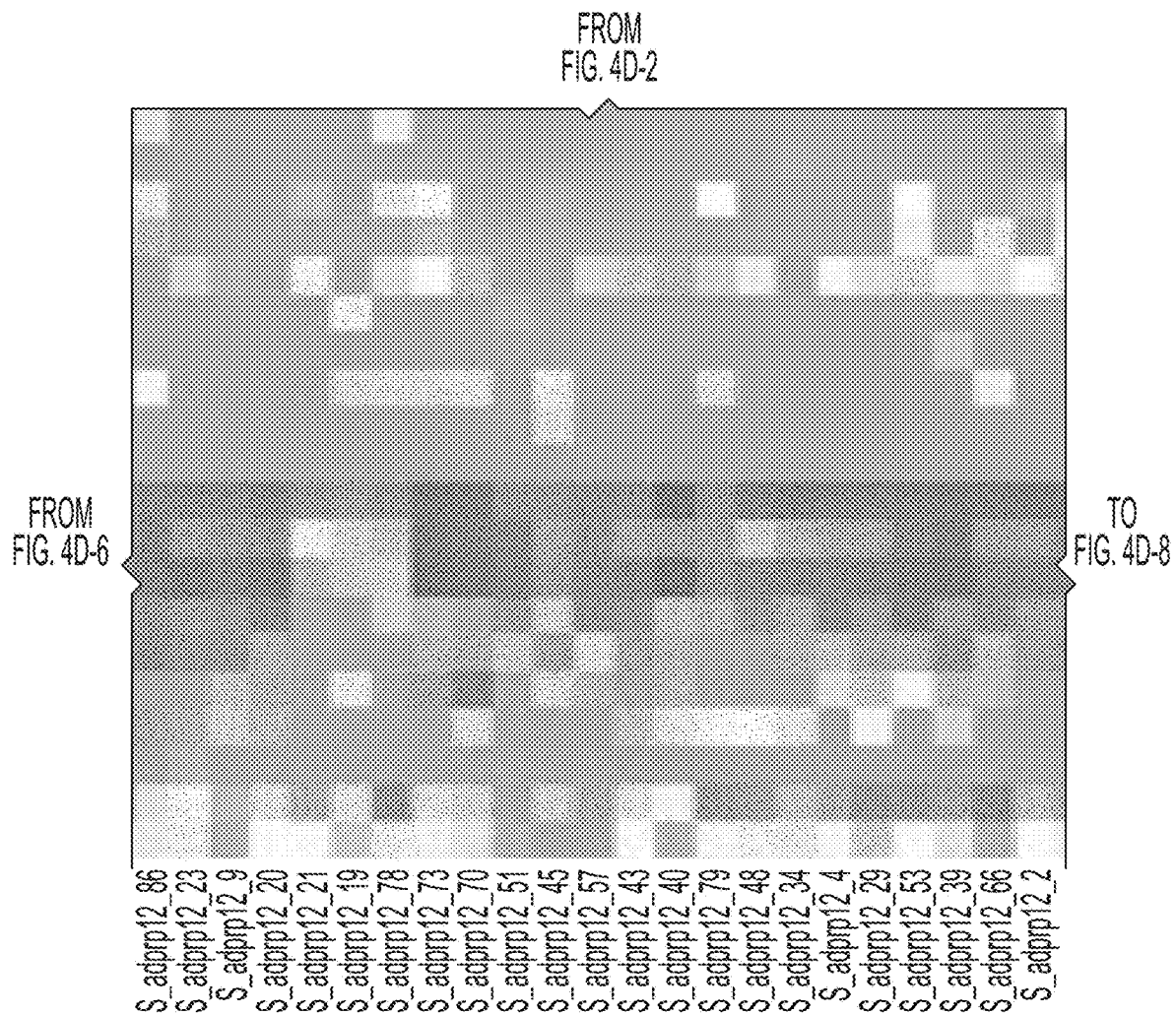
FIG. 7: RM Medium Optimization. Flow cytometry analysis of day 18 RPCs grown in RM medium with or without the addition of FGF2 and SB431542.
Figures 4, 4D, 5, 6, 7, 8:
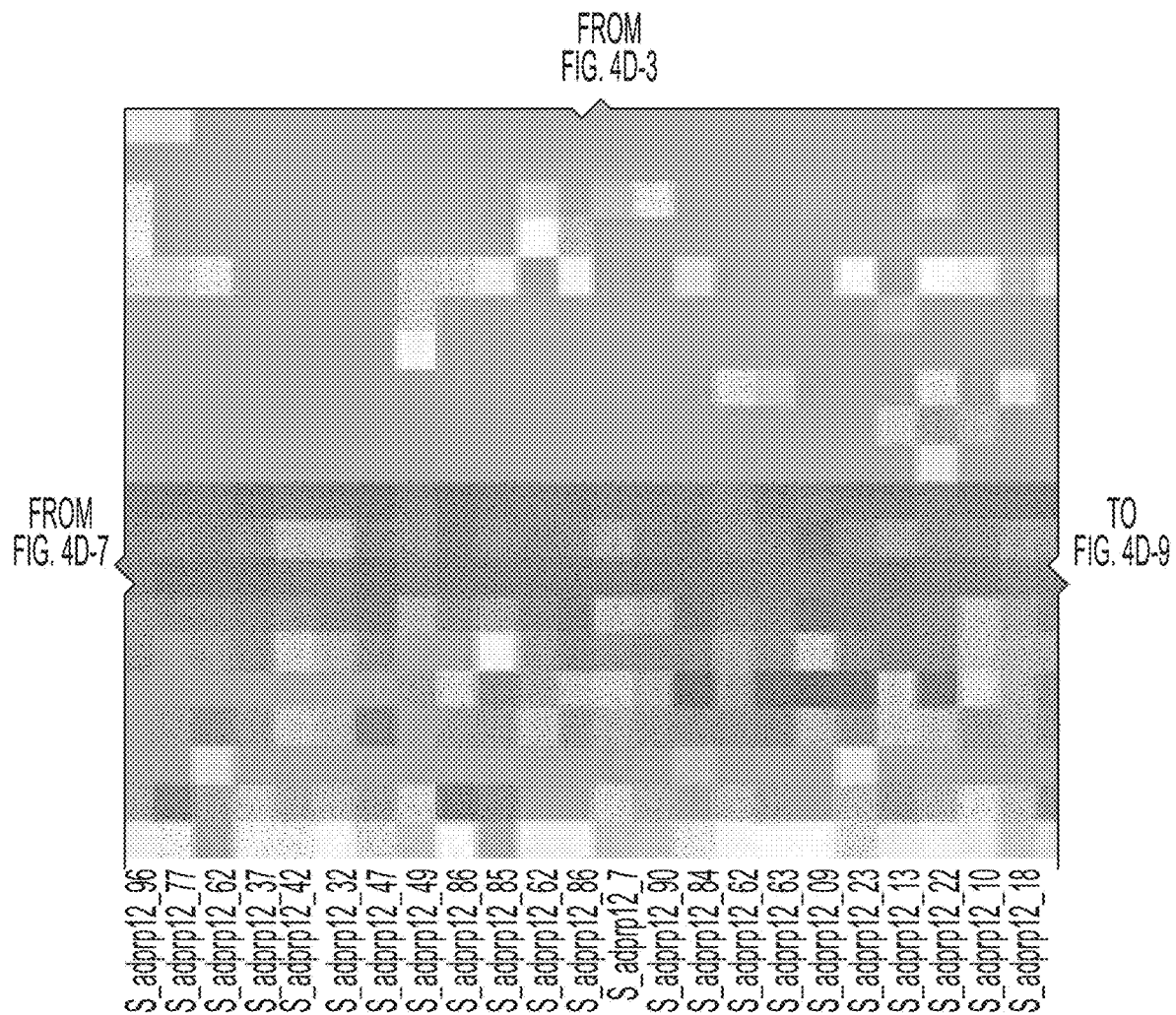
Figures 4, 4D, 5, 6, 7, 8, 9:
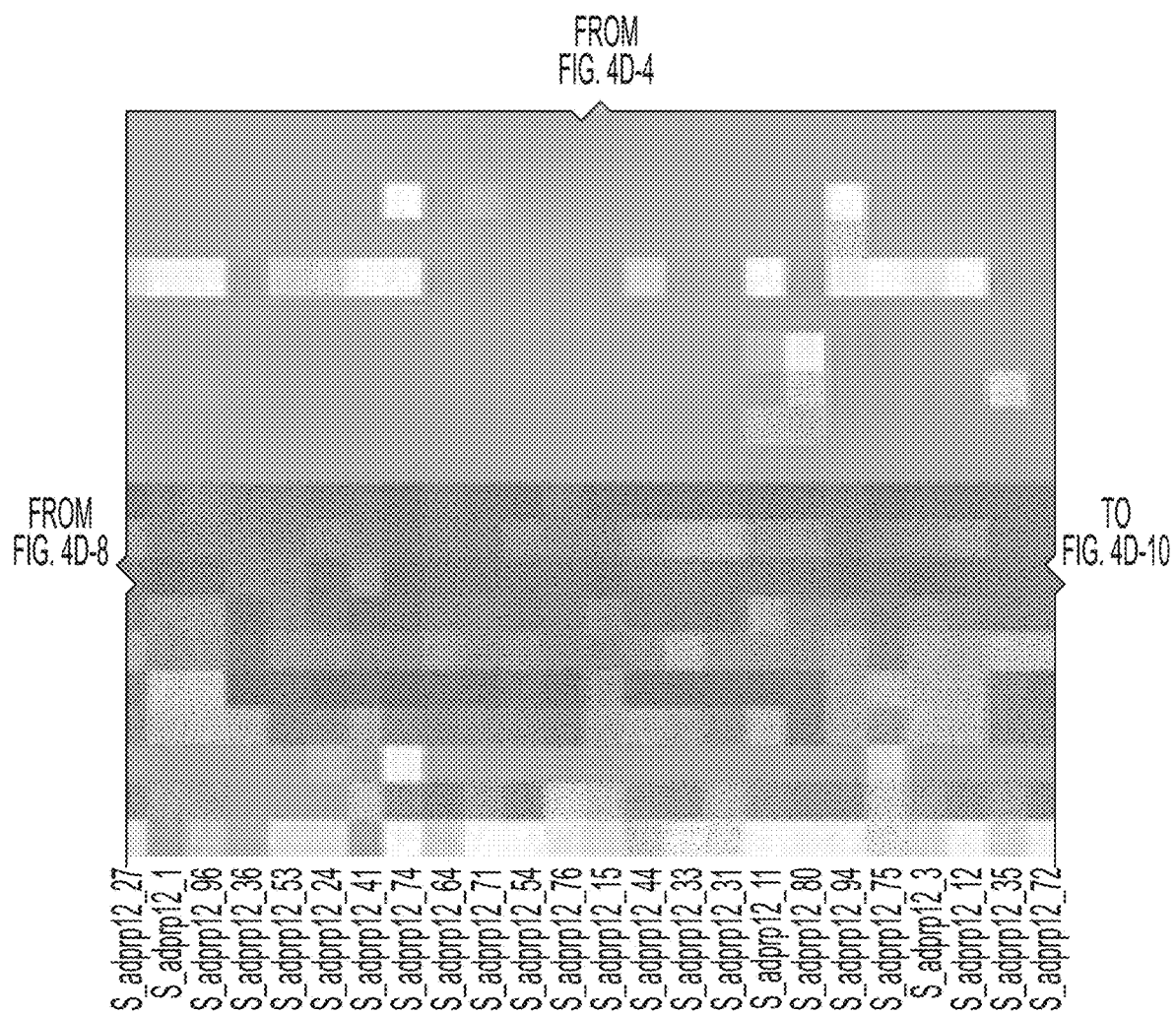
FIG. 9: Hybrid PRP MACS Enrichment. Flow cytometry analysis of Hybrid PRP for TUBB3, NESTIN and RCVRN expression both pre- and post-MACS enrichment.
Figures 4, 4D, 5, 6, 7, 8, 9, 10:
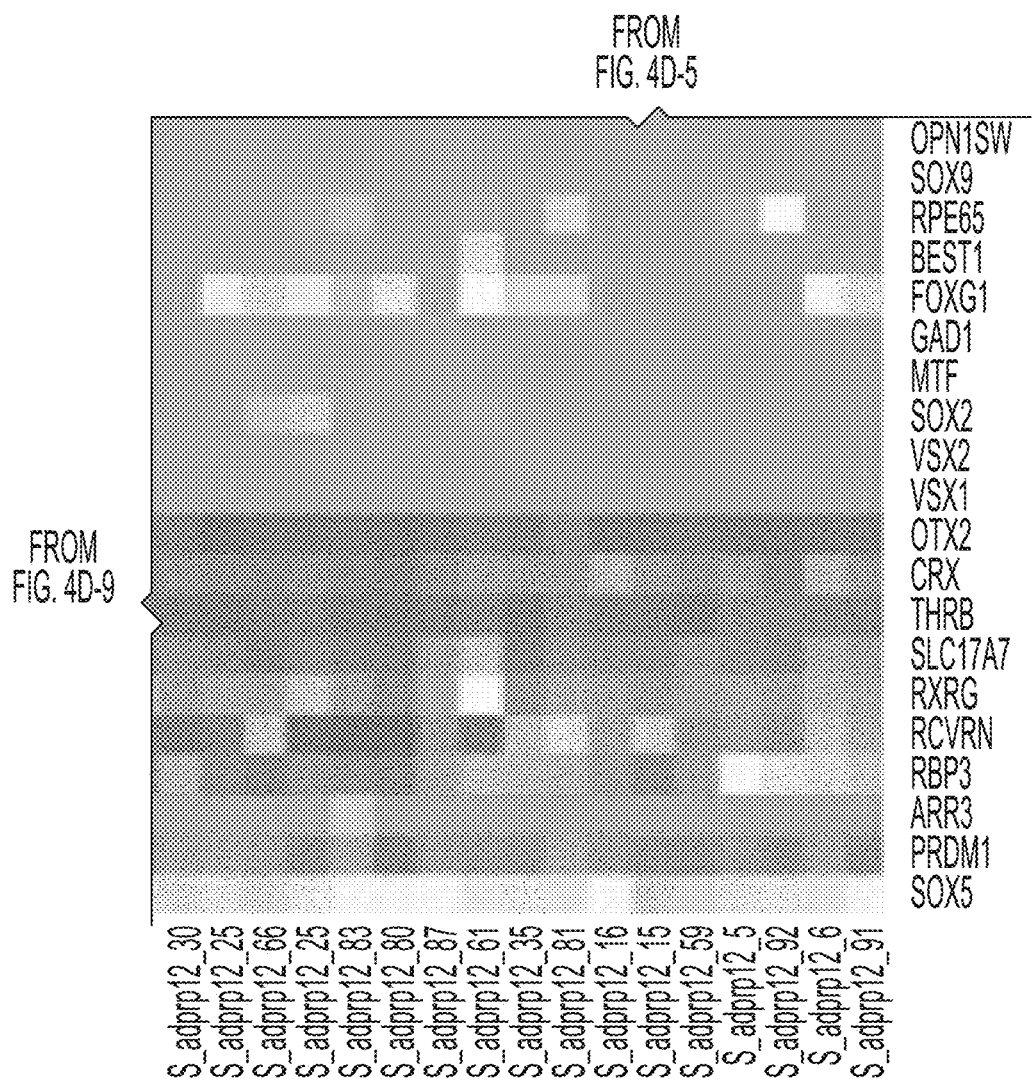
Figure 5:
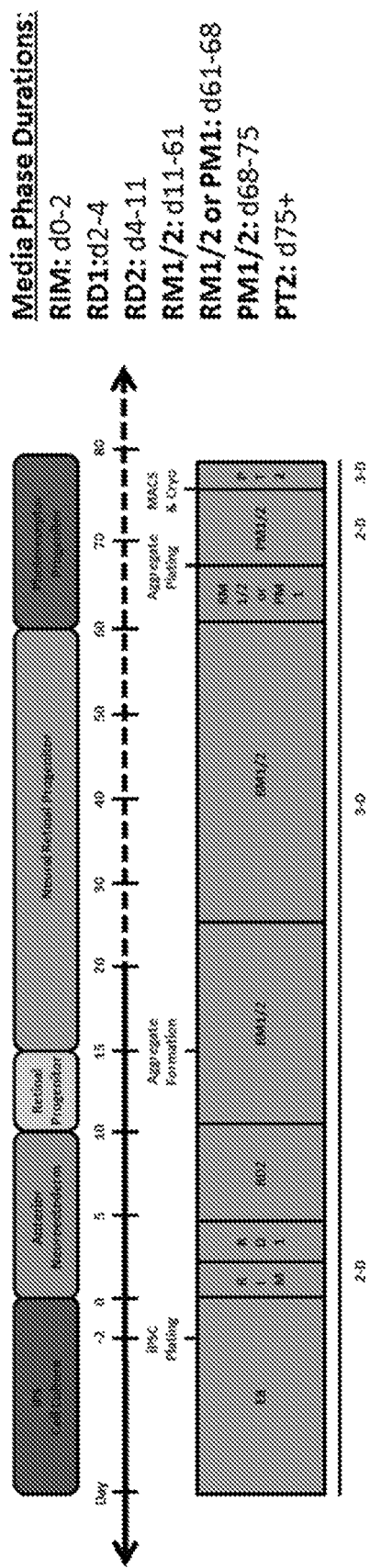
Figure 6:
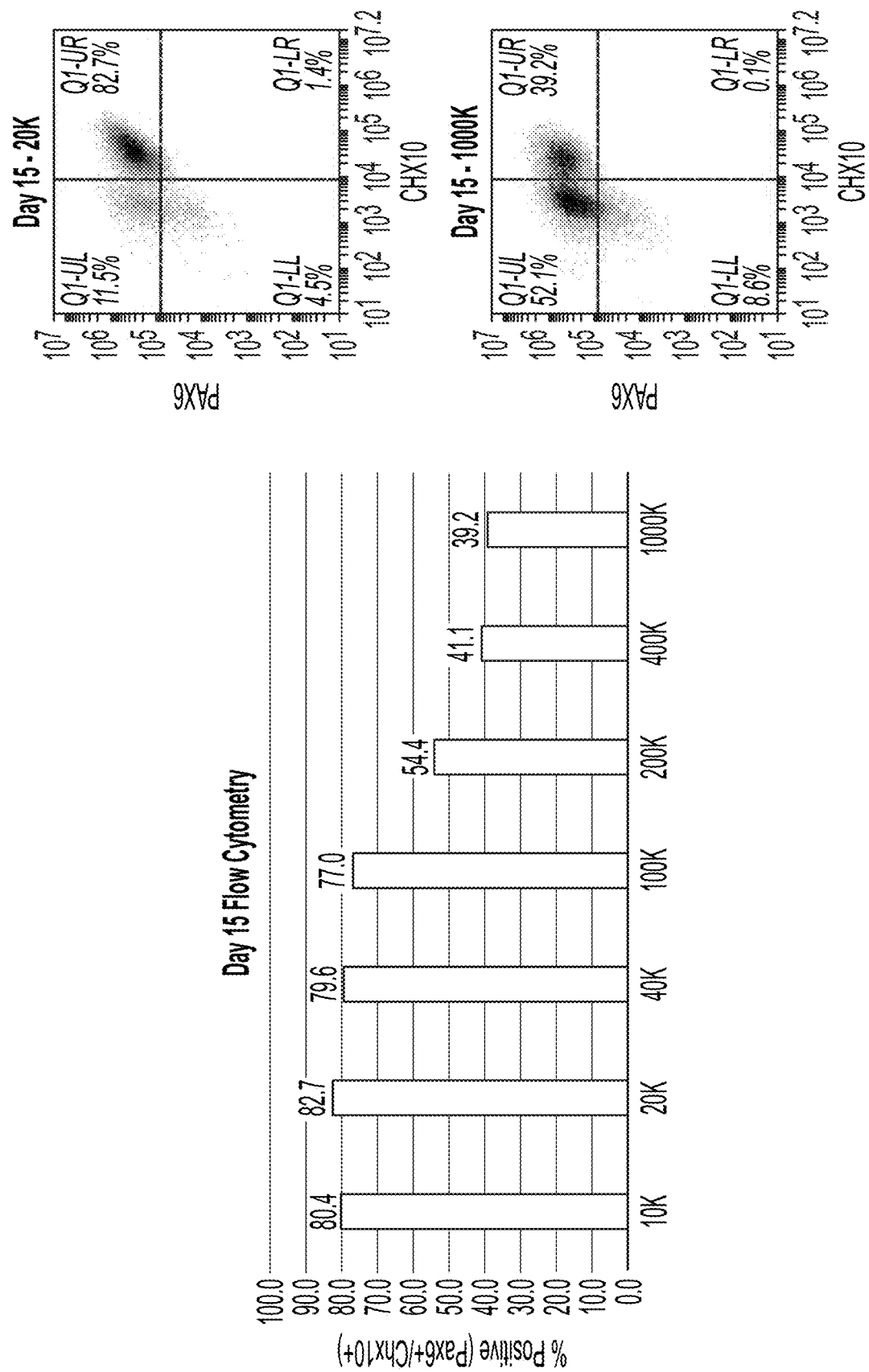
Figure 7:
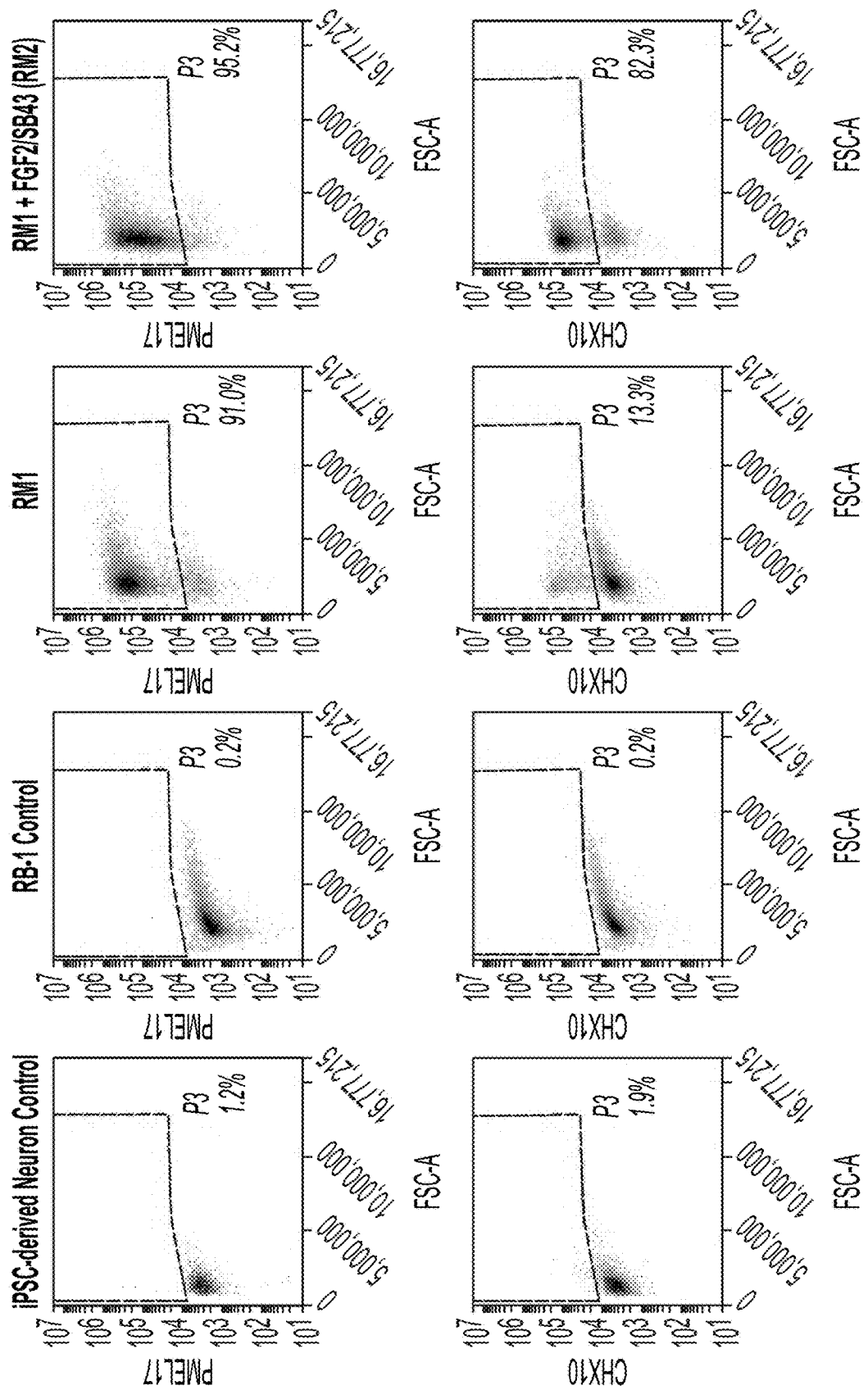
Figure 8A:
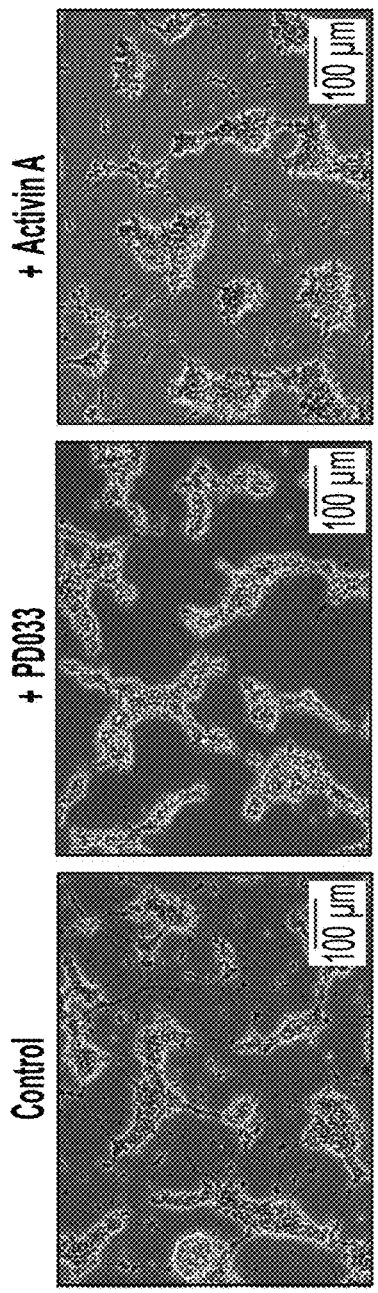
FIGS. 8A-8B: PM Medium Optimization.
Figure 8B:
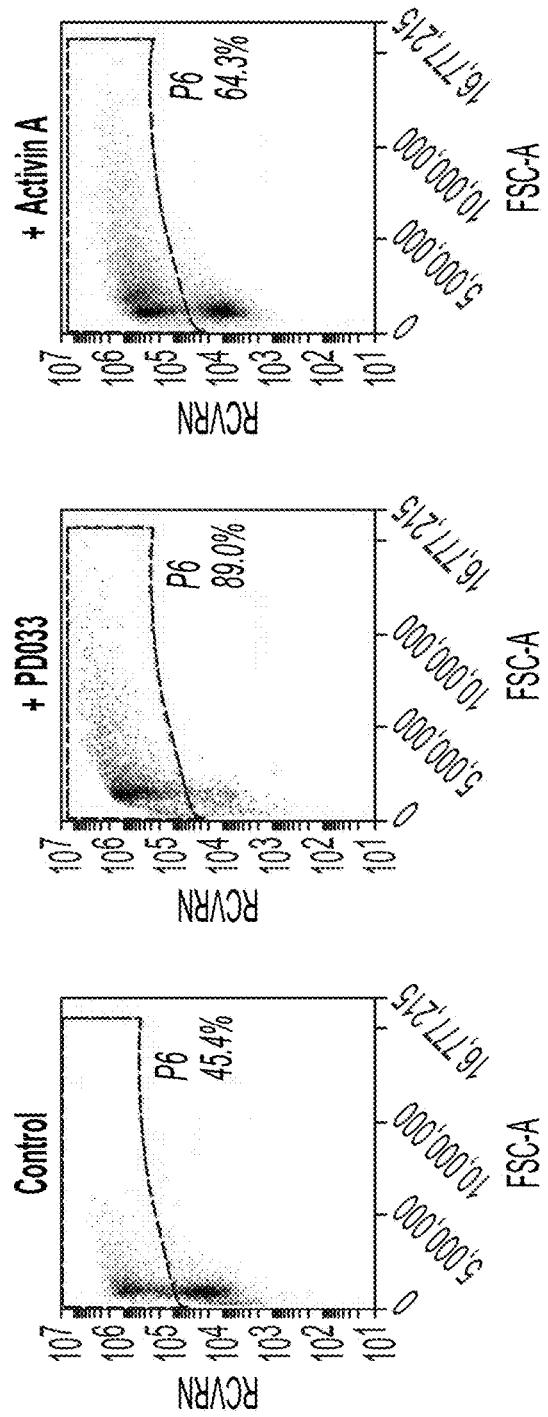
Figure 9:
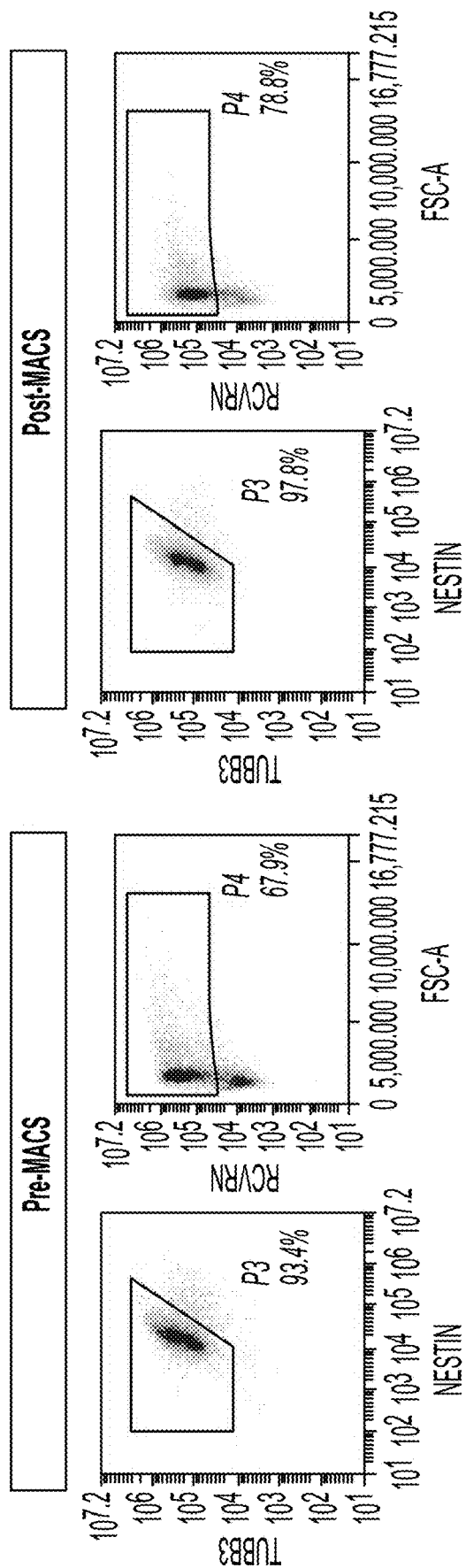
Figures 10A, 10B, 10C:
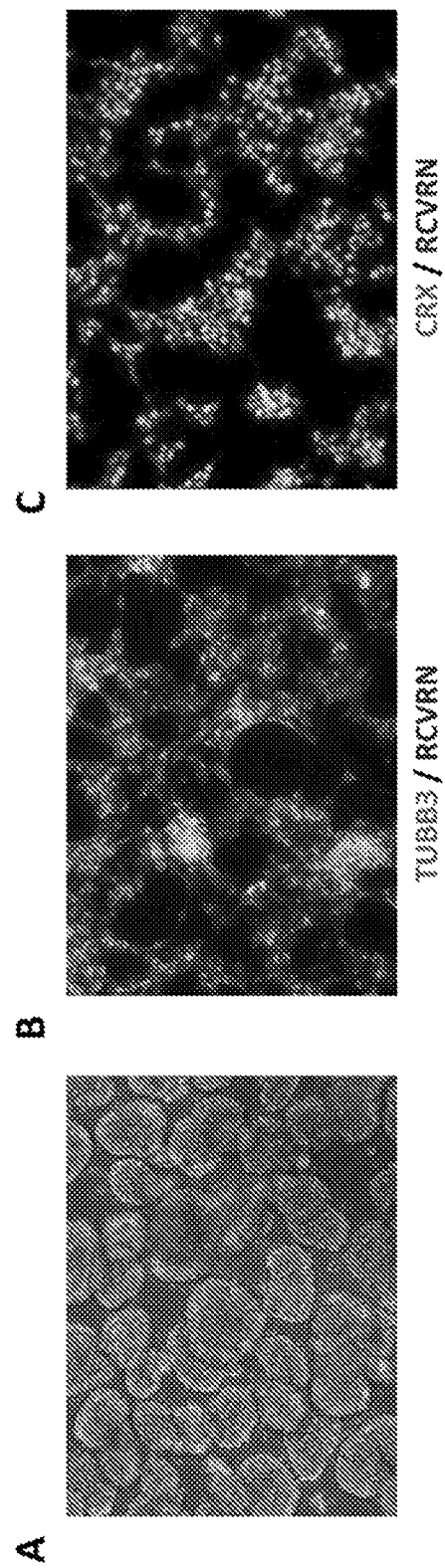
FIGS. 10A-10D: Hybrid PRP Characterization.
Figures 1, 10D:
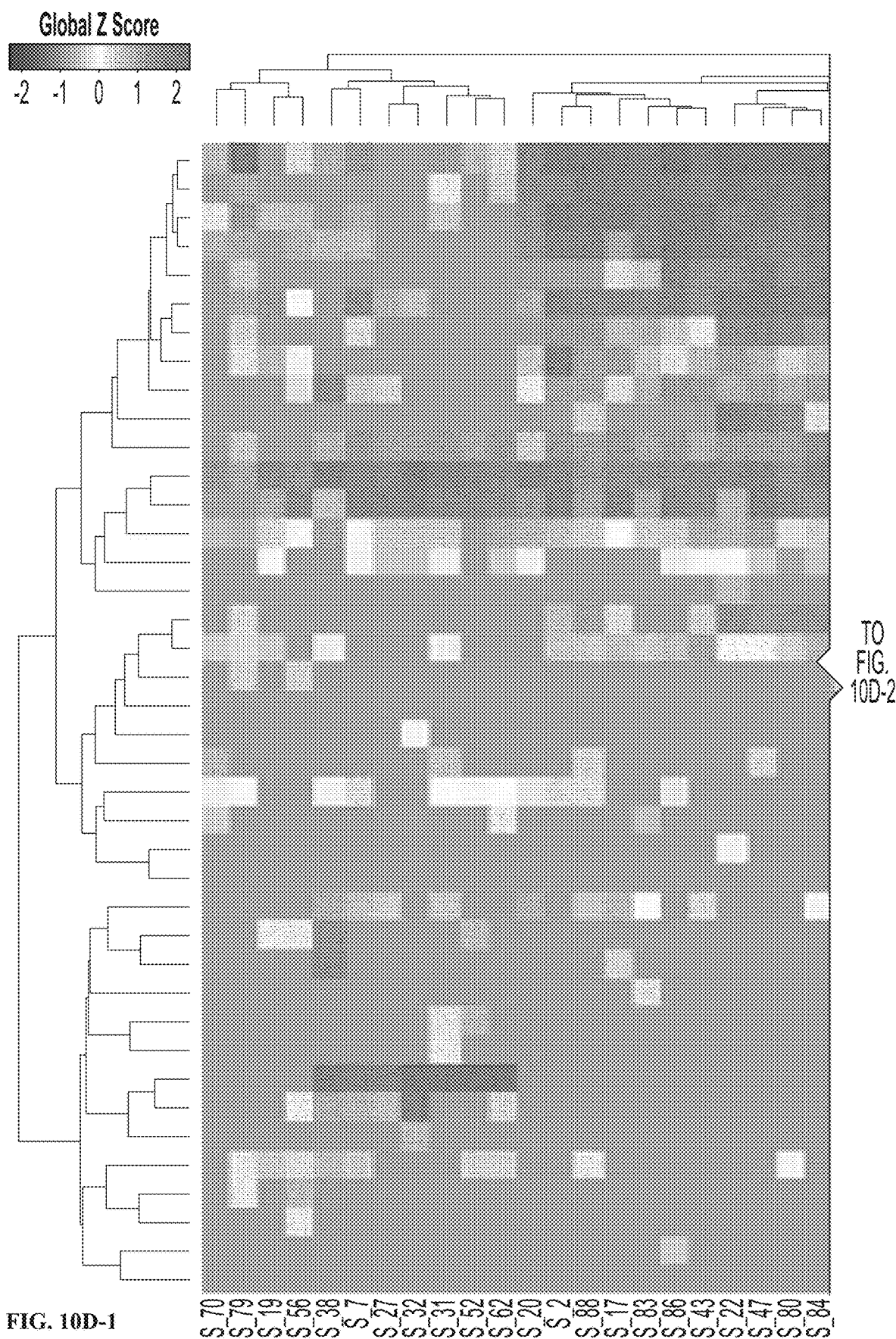
Figures 2, 10D:
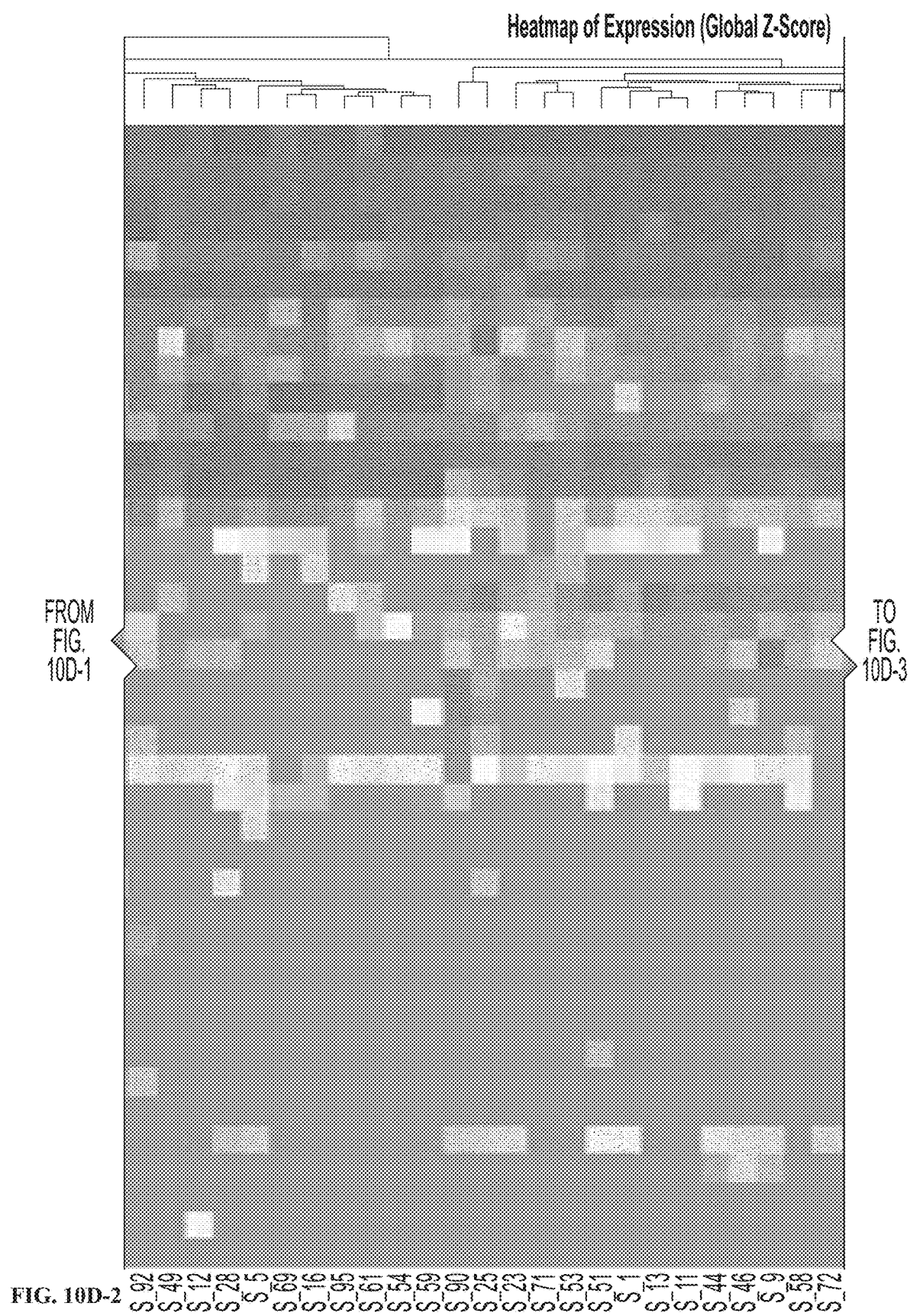
Figures 4, 10D:
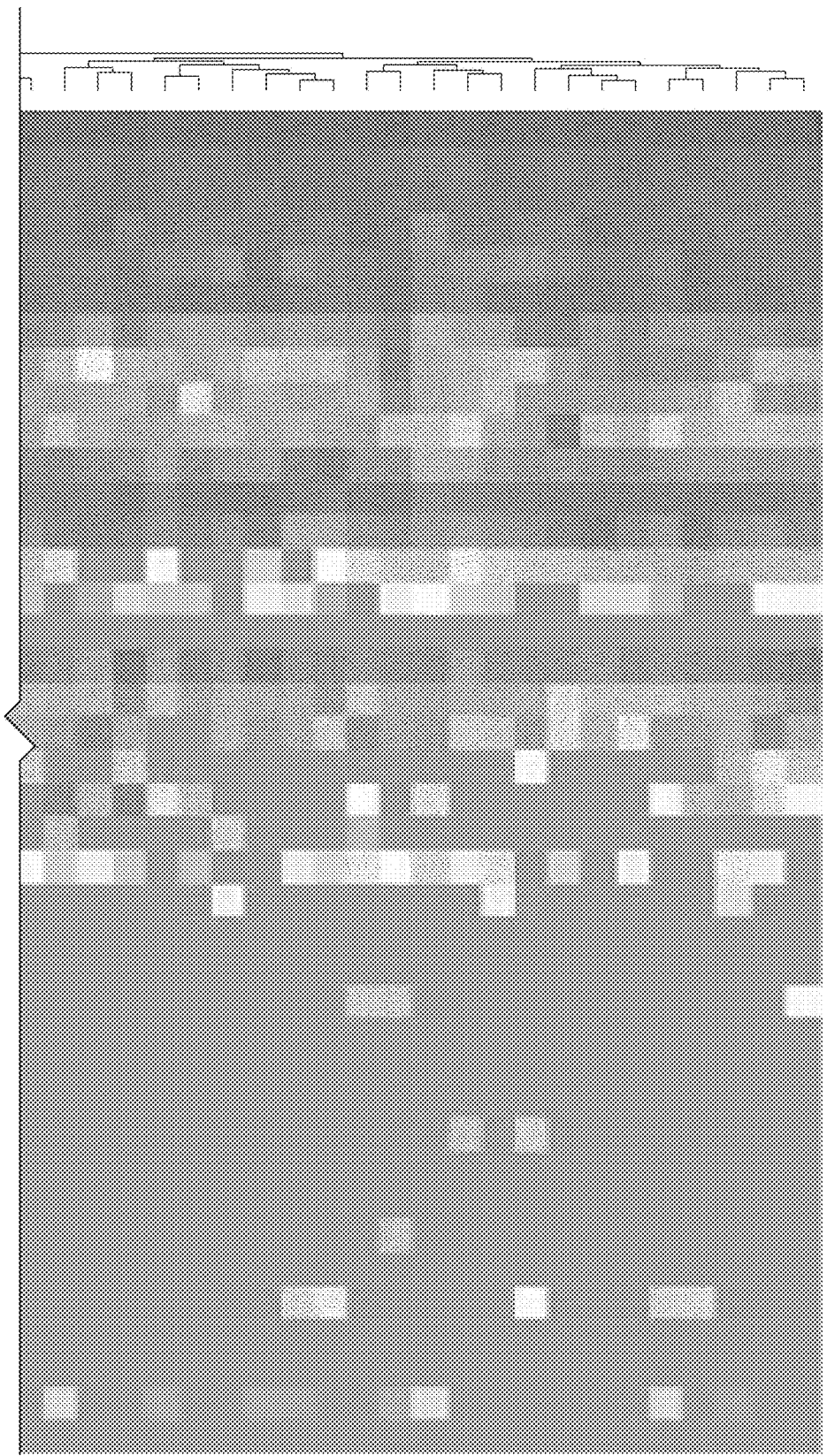
Figure 11:
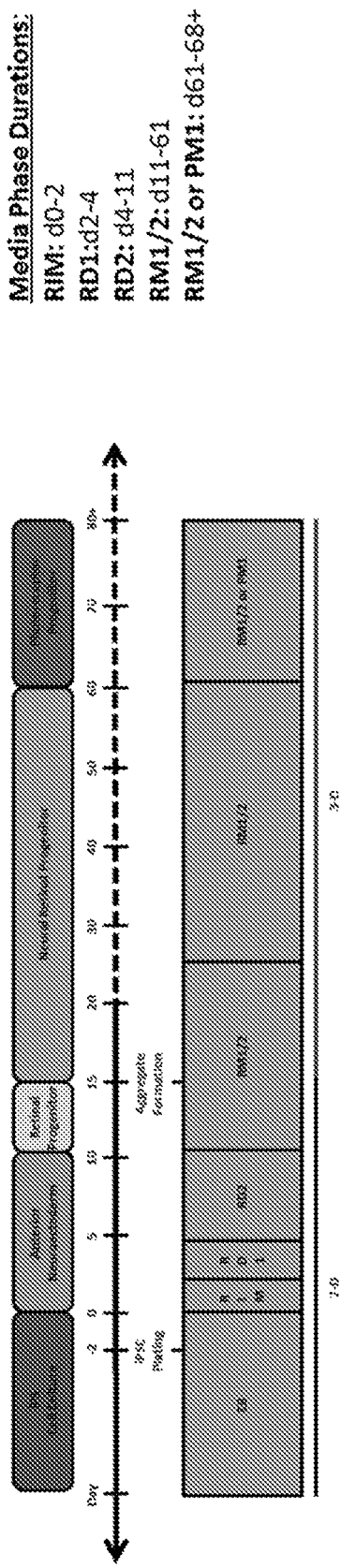
FIG. 11: Schematic of the Hybrid OV differentiation process.

The RPC cells of Example 2 were cultured as aggregates in RM1 or RM2 media (Table 1) for about 40 to 70 days. Blebbistatin was used during aggregate formation. The RM2 media comprises DAPT in addition to the components of the RM1 media. The cells remained in aggregates until approximately day 68, at which point they were dissociated, treated with BENZONASE® and plated for 7 days in RM2 media to generate Hybrid PRP cells. These Hybrid PRP cells displayed a phenotype similar to the PRP cells of Example 3. After magnetic-activated cell sorting (MACS) purification, the Hybrid PRP cell population was over 97% positive for TUBB3 while negative (<3%) for NESTIN and almost 80% positive for RCVRN (FIG. 10).

Example 6—Cryopreservation of NRPs or PRPS

For the cryopreservation of the differentiated NRPs or PRPs, the medium was aspirated and the cells were washed with Dulbecco's Phosphate-Buffered Saline (DPBS). The cells were then incubated with a cell dissociation enzyme and the cell suspension was pipetted into a conical tube. The cells were centrifuged, the supernatant aspirated and the cells resuspended in room temperature medium. The cell suspension was then filtered through a STERIFLIP® cell strainer (20 μm) and the cells were counted. Next, the cells were centrifuged and resuspended at an appropriate density (e.g. $1 \times 10^7$ cells/mL) in cold CryoStor® CS10. The cell suspension was aliquoted into pre-labeled cryovials which were placed in a cold freezing container and transferred to a −80° C. freezer for 12-24 hours. The vials were then transferred to liquid nitrogen for storage.

Alternatively, the cells may be cryopreserved as aggregates instead of dissociation into the single cell suspension. For example, following CliniMACS enrichment of D75 PRP, single cells were allowed to re-aggregate in tissue culture flasks for two days in minimal medium (RMN). Aggregates were pooled at D77 and a sample aliquot was obtained for cell counts. Following a series of washes, aggregates were resuspended in CryoSTOR CS10 Freeze Medium and 1 ml of the aggregate suspensions were transferred to liquid nitrogen storage vials at $25 \times 10^{\wedge}6$ aggregated cell products/vial.

Morphologically, thawed aggregates remaining in culture were not different than aggregates formed from single cells 2 days post-thaw. The thawed aggregates had 67% cell viability compared to 37% for thawed single cells. Four conditions were tested for RCVRN (on-target PRP marker), CHX10 (early eye field cells), RCVRN+, CHX10 (off-target bipolar cells), Ki67 (off-target proliferating cell) and Pax6 (off-target neuroectoderm/early eye field) expression: Cryopreserved single cells thawed and allowed to re-aggregate for 2 days in RMN medium (SC D77 2d post-thaw aggregates); single cells following enrichment allowed to aggregate for 2 days in RMN, without cryopreservation (D77 pre-cryo cultured aggregates); cryopreserved aggregates immediately post-thaw (D77 aggregates at thaw); and cryopreserved aggregates thawed and cultured 2 days in RMN medium (D79 thawed aggregates cultured 2d). There was no difference in RCVRN expression among the four conditions. Off-target markers for early eye field (CHX10+ and Pax6+) remained low in all conditions and proliferative cells (Ki67+) were negligible.

Table 2. Mean percent on-target and off-target markers in aggregated single cells versus thawed cryopreserved aggregates (reported as mean±SEM).

| | RCVRN % | CHX10 % | RCVRN + CHX10 % | Ki67 % | Pax6 % |
|---|---|---|---|---|---|
| SC D77 2d post-thaw aggregates | 94.6 ± 0.03 | 4.6 ± 0.03 | 2.5 ± 0.02 | 0.2 ± 0.001 | 4.0 ± 0.01 |
| D77 pre-cryo cultured aggregates | 92.3 ± 0.02 | 5.2 ± 0.02 | 3.9 ± 0.01 | 0.1 ± 0.001 | 3.4 ± 0.01 |
| D77 aggregates at thaw | 95.2 ± 0.02 | 3.7 ± 0.01 | 2.4 ± 0.01 | 0.1 ± 0.000 | 3.1 ± 0.01 |
| D79 thawed aggregates cultured 2d | 91.4 ± 0.03 | 4.4 ± 0.01 | 2.4 ± 0.01 | 0.5 ± 0.002 | 5.1 ± 0.02 |

Thus, it was shown that not only can cryopreserve aggregates be successfully cryopreserved, but the enriched PRPs are not compromised during the cryopreservation or the thawing stages. This was evident by the similar high expression of the on-target PRP marker recoverin. Similarly, off-target markers and proliferating cell makers remained equally low throughout all conditions. Cryopreserving aggregates allows the product to go from the lab to the patient with minimal "in between" handing, as the transplanted product will be in aggregate form. The elimination of the 2 day "in between" culture step minimizes concerns of contamination and cell loss.

Example 7—MACS Purification of PRP Cells

The population of PRP cells can have residual contaminating non-PRP cells such as RPE cells or other nonneuronal cell types (collectively referred to as the "contaminating cells"), all of which can be separated and removed to yield a PRP-enriched cell population. The contaminating cells can be removed from the culture by various methodologies, such as, for example, Magnetic Activated Cell Sorting (MACS®), Fluorescent Activated Cell Sorting (FACS), or single cell sorting by positive selection and/or negative selection. The MACS® methodology, which is known in the art to separate various cell populations depending on their surface antigens, was used to separate the contaminating cells from the desired PRP cells.

Positive MACS selection for PRP cells can include isolation of cells which express the neuronal marker CD171. In order to carry out the positive MACS selection for PRP cells, the total population of PRP cells from Example 3 or 6 were dissociated into a single cell suspension. The medium was aspirated, the cells were washed with DPBS, and TRYPLE™ was added to dissociate the cells. The cells were then collected and centrifuged. The cells were washed in PRP medium and filtered using a 20 μm steriflip cell strainer. The cell suspension was counted using ViCell and MACS buffer was added to the cell suspension at $1\times10^7$ cells/mL. Next, the cell suspension was stained with the primary antibody CD171-biotin (Miltenyi) at a 1:25 dilution. After incubation, 20 mL of MACS buffer was added and the cells were centrifuged at 400×g for 5 min. The cell pellet was resuspended in 20 mL MACS buffer, vigorously mixed, and centrifuged at 400×g for 5 min to remove any unbound antibody. The cell pellet was resuspended in MACS buffer (e.g., at $1.11\times10^8$ cells/mL), microbeads coated with the diluted (1:10) secondary antibody (e.g., anti-Biotin) were added, and the cells were incubated at 4° C. for 20 min. After incubation, the cells were washed with MACS buffer to remove unbound microbeads and up to $1.25\times10^8$ cells were resuspended in 500 μL MACS buffer. The cell suspension was transferred to a LS column placed in a strong magnetic field and the cells expressing the antigen CD171 attached to the microbeads remained in the column. The LS column was washed two times with MACS buffer. The enriched cell population was then flushed from the LS column and evaluated for post-sort purity analysis. Images of cell staining for RCVRN are shown in FIGS. 3 and 9 depicting that the MACS enrichment results in a significant enrichment of PRP cells.

Further studies were performed to identify additional surface proteins for the enrichment of PRP cells. Surface protein evaluation using Miltenyi Marker Screen plate identified SUSD2 as a surface protein target to enrich for photoreceptor precursor (PRP) product. Sushi Domain-Containing Protein-2 (SUSD2) is a type I transmembrane protein that facilitates cell-cell and cell-matrix adhesion. Overexpression of SUSD2 is observed in cancerous cells and SUSD2 is an established enrichment marker for various mesenchymal stem cells. Assaying D75 PRP 2.3 CBP for surface proteins revealed elevated SUSD2 expression on cells that labeled positive for recoverin, a neuronal-specific calcium-binding protein that is primarily expressed in photoreceptors. With this finding, SUSD2 was tested for use as an enrichment marker.

Figure 31A:
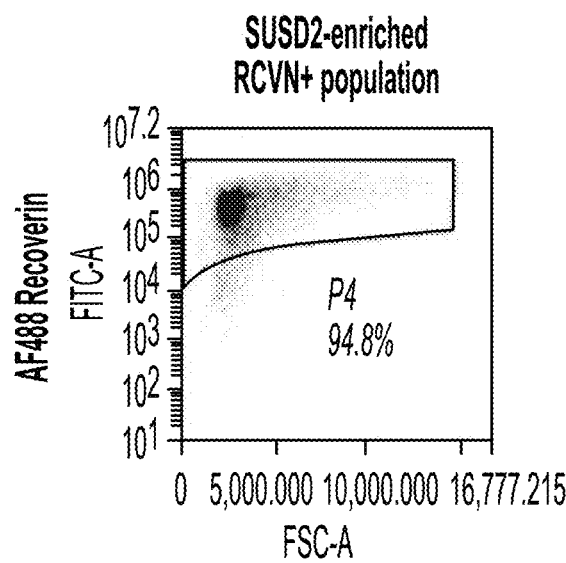
FIGS. 31A-31B: Recoverin expression is greater than 90% in PRP cells enriched with SUSD2 compared to CD171.
Figure 31B:
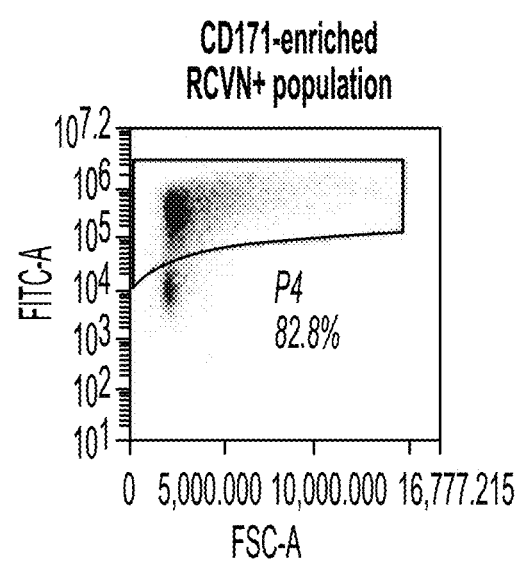
Figure 32A:
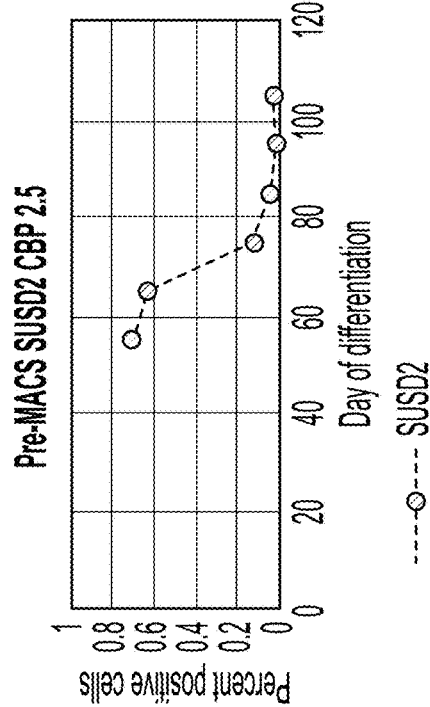
FIGS. 32A-32E: Maximum recoverin (FIG. 32A) and SUSD2 (FIG. 32B) expression was observed between differentiation day D55-D65, with recoverin peaking soon after SUSD2. Recoverin and SUSD2 co-expression (FIG. 32C) mimics the SUSD2 alone expression, suggesting that SUSD2-expressing cells also express recoverin while not all recoverin-positive cells express SUSD2. An overlay of the three graphs clearly demonstrates the parallel expression of the dual recoverin/SUSD2 versus the single SUSD2 stain (FIG. 32D). SUSD2-labeling with post-fixed recoverin labeling. Independent time course studies of recoverin and SUSD2 co-expression from early stage D55 through later stage D105 (FIG. 32E) supports peak SUSD2 expression around D65 but also shows equally elevated expression at D55.
Figure 32B:
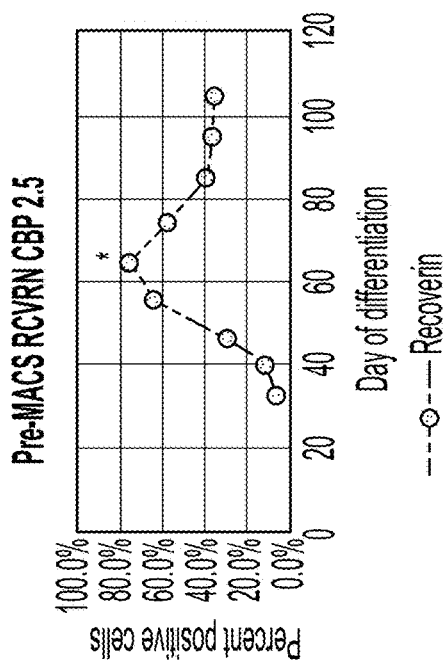
Figure 32C:
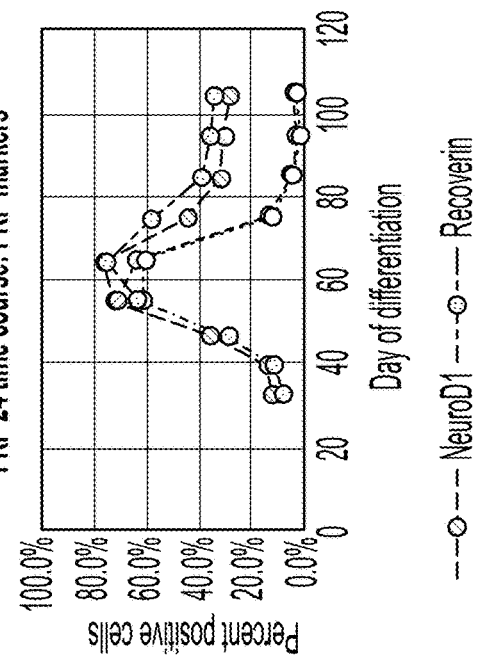
Figure 32D:
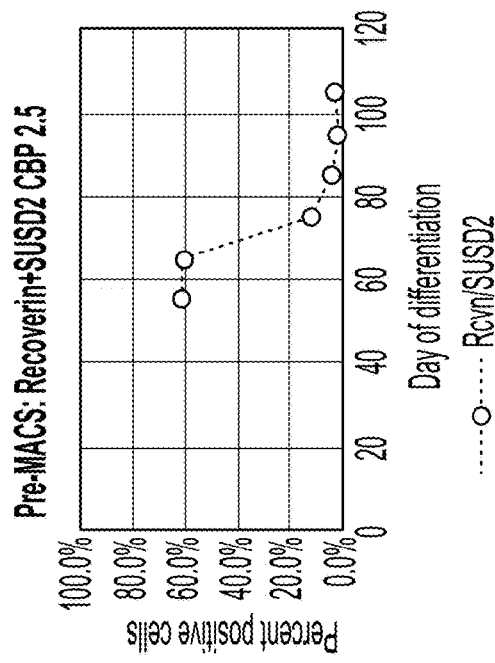
Figures 1, 32E:
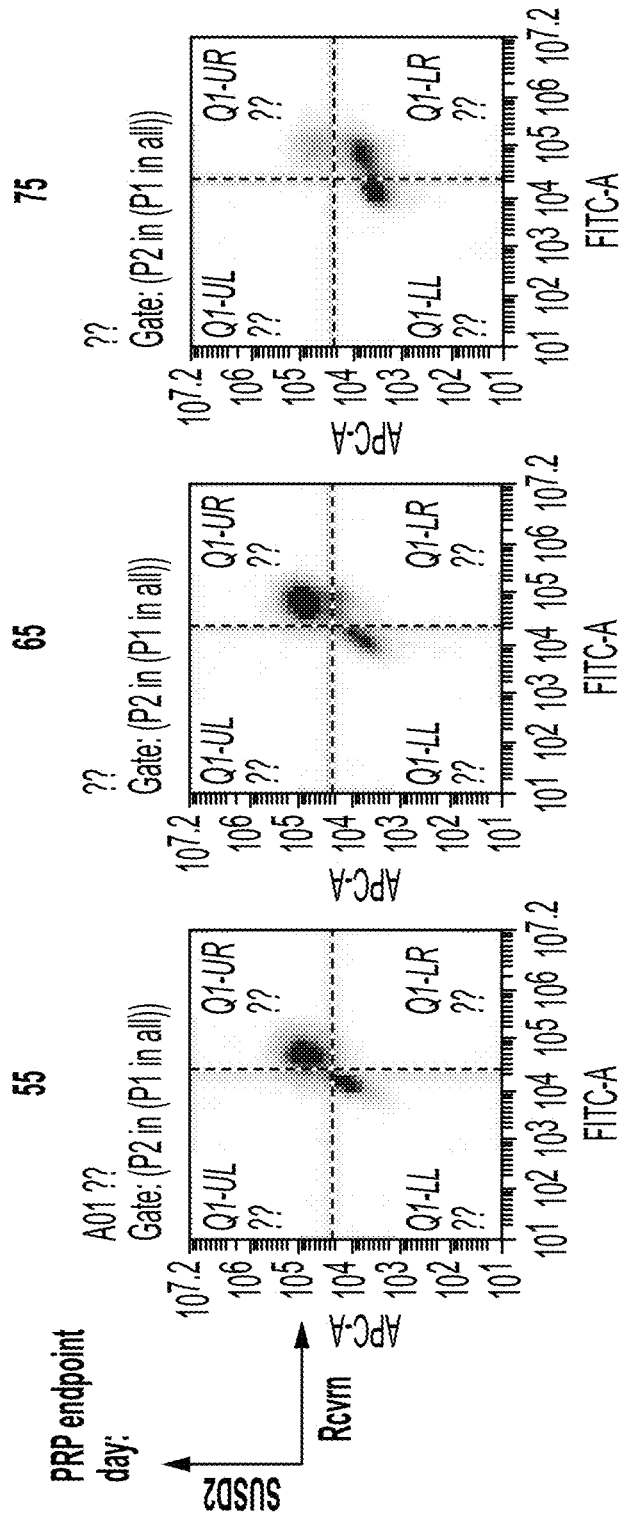
Figures 2, 32E:
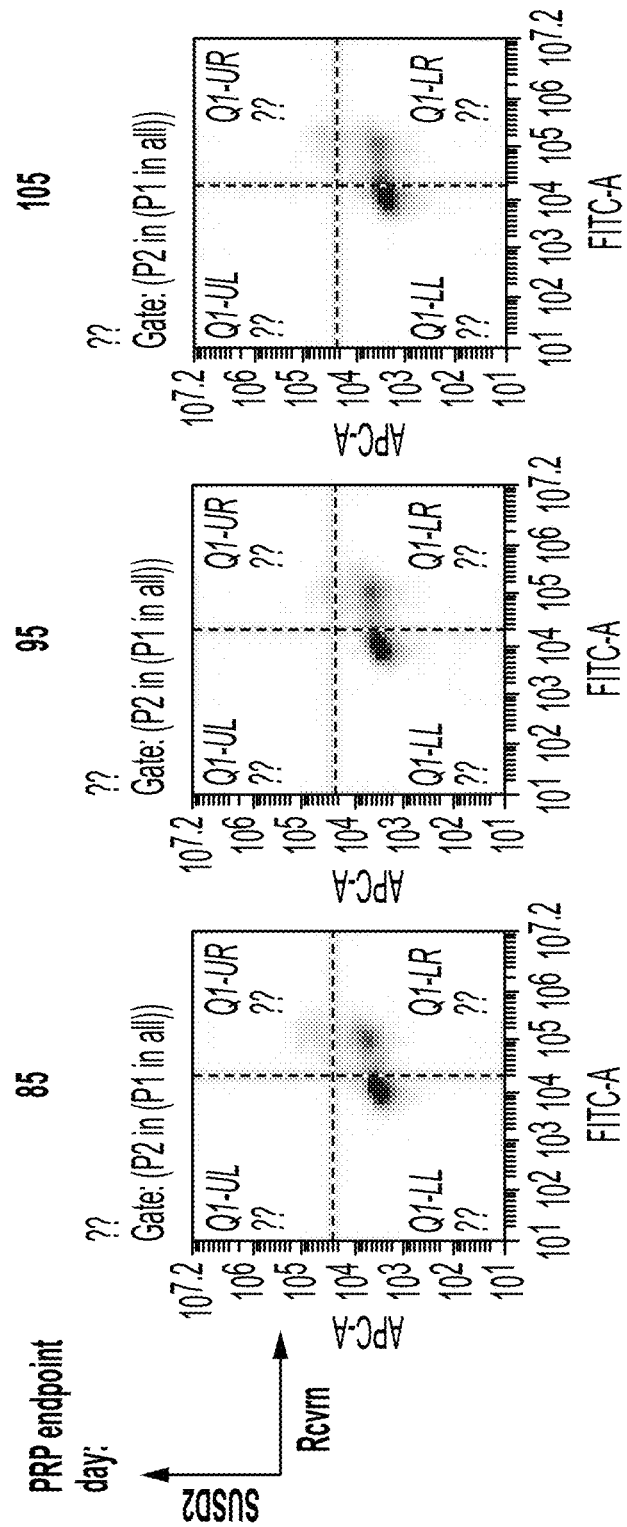
Figure 34E:
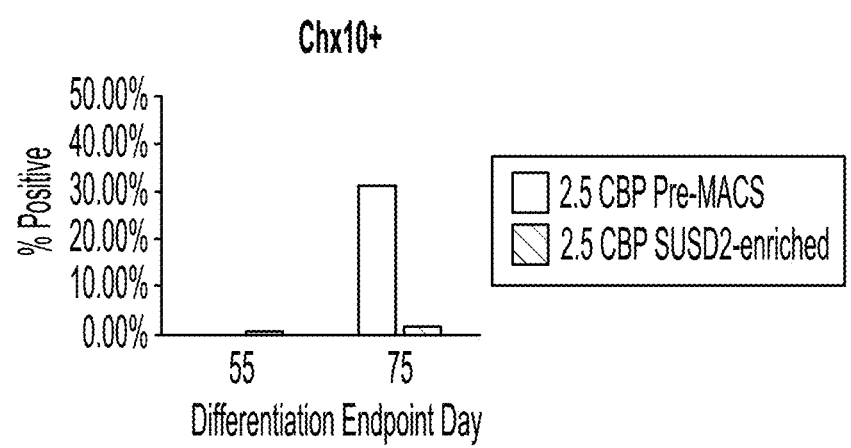

SUSD2 had high co-expression with recoverin, a marker expressed by cells fated to become photoreceptors. Additionally, SUSD2 enriched for ~95% recoverin positive-positive cells compared to ~83% recoverin-positive cell following CD171-enrichment (FIG. 31). Studies were performed on cells pre-treated with DAPT and plated on to LN521 with PD0332991 in the presence of DAPT. Recoverin coupled with CHX10, a transcription factor highly selective for early stage neural retinal progenitor cells, may be considered a hallmark characterization marker for (cone) bipolar cells (FIG. 34). Bipolar cells are late born retinal neurons which interconnect with photoreceptors and ganglion cells to facilitate signal transduction. CHX10-positive (recoverin-negative) cells may also be expressed in a subset of Muller glia cells.

Figure 33B:
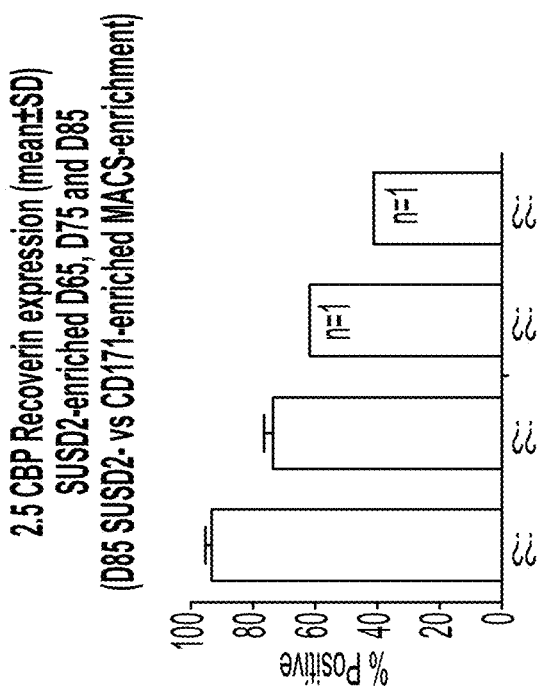
FIGS. 33A-33C: Percentage recoverin expression increased further post SUSD2-enrichment at D65, D75 and D85 (FIG. 33A), showing highest expression at D65 which also corresponds to early peak SUSD2 and recoverin expression times. Although percent recoverin-positive cell population decreases from D65 to D75 to D85 (B), SUSD2-enrichment still enhances percentage recoverin-positive cells compared to CD171-enrichment at D85 (FIG. 33B). However, a limitation of SUSD2-enrichment is low cell output, with <25% of the initial cell input recovered following enrichment (FIG. 33C). This holds true for cells enriched with either SUSD2 or CD171 at D85, whereby only 3% of total input cells are enriched with SUSD2 while only 18% of total input cells are enriched by CD171. The flow-through (labeled as SUSD2- and CD171-) appeared to contain the majority of the cells, suggesting a possible reduction in expression of both surface markers at later differentiation stages.
Figure 33A:
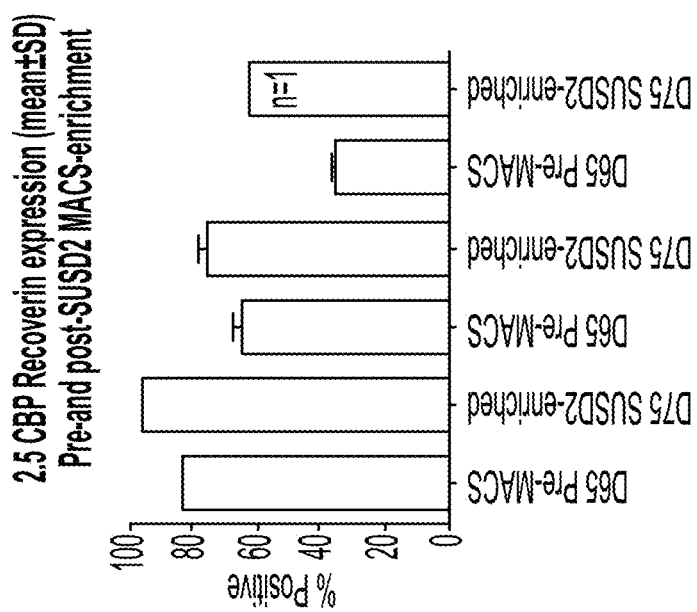
Figure 33C:
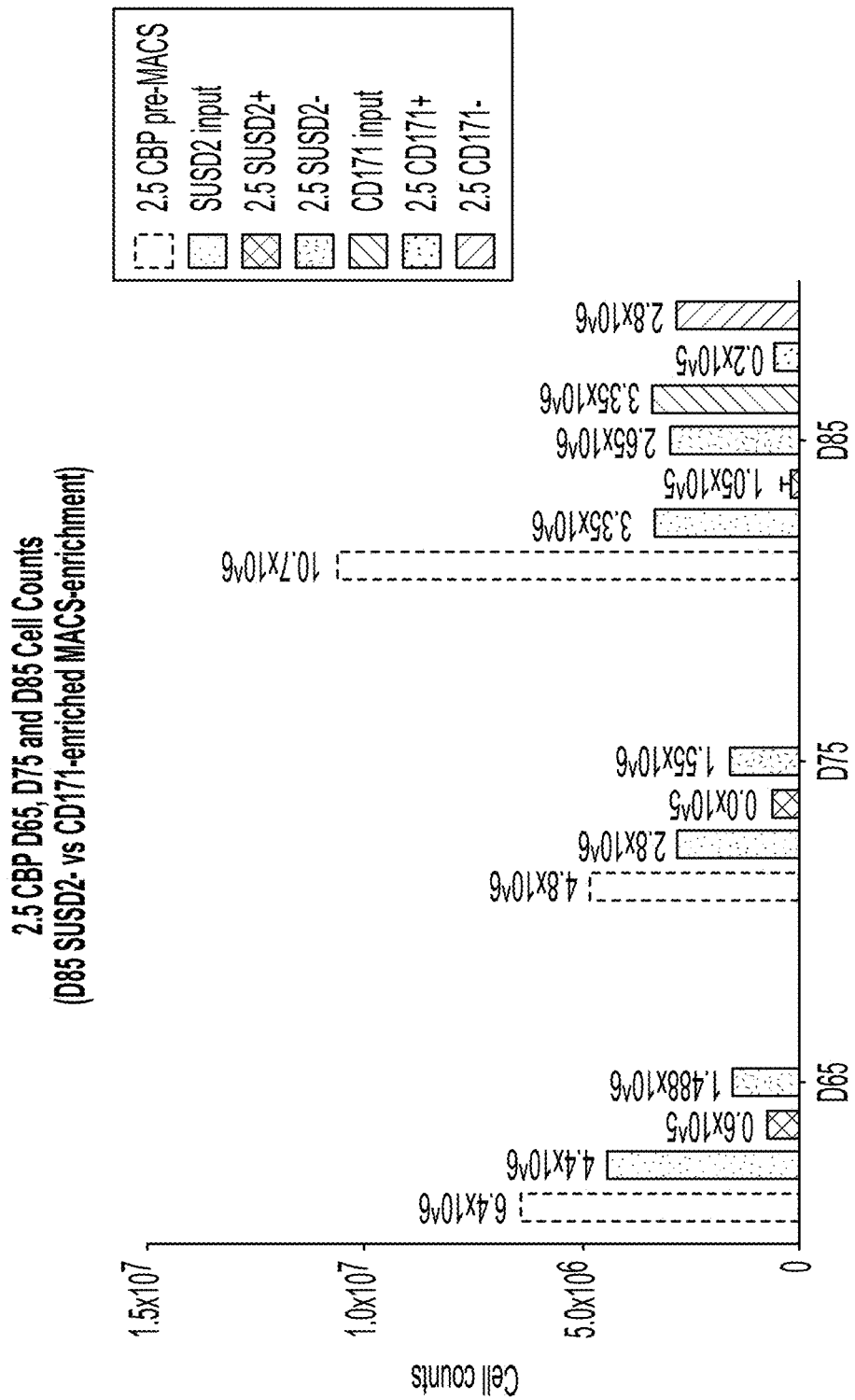

SUSD2 expression was investigated concurrent with RCVRN expression for differentiation endpoints from D55 through D105, prior to MACS enrichment (FIG. 32). The precision by which SUSD2 targets only PRP and no other retinal neurons was important for the final product's purity. Despite low cell yield following SUSD2 enrichment, the SUSD2 marker enriched recoverin-expressing cells at each time examined (Table 3) suggesting that SUSD2 is a highly specific marker for recoverin-positive possible PRP. FIG. 33 further demonstrates SUSD2-target specificity.

As previously discussed, CHX10 and recoverin are hallmark characterization markers for (cone) bipolar cells. CHX10 is expressed early in retinal progenitor cells and downregulates expression in post-mitotic PRP but remains highly expressed in post-mitotic bipolar cells and some Muller glia cells. The studies showed that CHX10 is low at the earlier (D65) timepoint, in both pre- and post-SUSD2 MACS-enrichment. Additionally, recoverin-CHX10 expression is negligible at this time, suggesting there are no bipolar cells in the product following SUSD2-enrichment at this time.

Conversely, co-labeling recoverin and neuronal differentiation factor 1 (NeuroD1, ND1), a transiently expressed transcription factor that plays a role in the terminal differentiation of photoreceptors, showed high expression levels at D65 pre- and post-SUSD2 MACS-enrichment. Past D65, RCVRN-CHX10-expressing bipolar cells (and/or possibly some CHX10-expressing Muller glia cells) were observed. RCVRN-ND1-expression gradually downregulated and the combination was expressed in less than half of the enriched D85 cells compared to D65 and D75, likely consistent with the transient expression of ND1.

Table 3: Performing MACS at several time points shows SUSD2 consistently improves the population's recoverin expression and yields high cell recovery at differentiation endpoint days 55-65. The high yield further illustrates high SUSD2 expression at these time points.

| Batch | Day | Recoverin % Pre-MACS | Recoverin % SUSD2 enrich | MACS % Yield SUSD2 enrich |
|---|---|---|---|---|
| ADD PRP24 | 55 | 67.64% | 81.37% | 49.0% |
| ADD PRP25 | 55 | 65.70% | 81.37% | 43.6% |
| ADD PRP27 | 56 | 66.41% | 73.29% | 46.0% |
| ADD PRP28 | 59 | 80.45% | 84.52% | 39.74% |
| ADD PRP27 | 65 | 88.21% | 91.56% | 29.21% |
| ADD PRP24 | 65 | 78.97% | 92.51% | 34.9% |
| MJS PRP28 | 75 | 44.37% | 79.33% | 7.4% |
| ADD PRP24 | 76 | 72.38% | 88.05% | 3.5% |
| ADD PRP23 | 78 | 41.99% | 75.16% | 2.6% |

These studies, coupled with peak SUSD2 expression time, suggested that SUSD2 is a good enrichment marker at early time points, such as D65. Furthermore, at D65, SUSD2 was highly selective for RCVRN- and ND1-expressing cells but not for CHX10-expressing (off-target or progenitor) cells. The selective attribute of SUSD2 was highlighted by the enrichment of a highly recoverin-positive pure population even when cell yield post-enrichment was marginal. Overall, SUSD2 is a valuable target marker for PRP enrichment provided the final product is manufactured at early time points when SUSD2 expression is high, such as D55 and D65.

In addition to SUSD2 and CD171, alternative potential PRP enrichment markers were pinpointed. These surface markers also co-localized with recoverin, a neuronal-specific calcium-binding protein that is primarily expressed in photoreceptors and cone bipolar cells (Gunhan et al., 2003; Haverkamp et al., 2003), although to a lesser extent. Table 4 lists 15 additional potential PRP enrichment markers, excluding CD171 and SUSD2.

dropped by D75. The data suggests that D65 may be the optimal time point for PRP enrichment with these specific surface antigens (excluding CD133).

FIGS. 17-22 display a tabular and graphical representation of the percent expression of recoverin (on-target PRP marker) with off-target cell markers Pax6 (expressed by retinal progenitor cells-RPC, amacrine cells-AC and retinal ganglion cells-RGC), Onecut1 (expressed by RPCs and horizontal cells), Ki67 (expressed by proliferating cells) and CHX10 (expressed by RPC and co-expressed with recoverin on bipolar cells). The highest recoverin expression occurred with CD344-enrichment. The eluted fraction for each enrichment showed some recoverin-positive cells but over-

TABLE 4

Surface proteins evaluated for PRP enrichment.

| Antigen | Description | % co-expression with RCVRN | % (antigen+/recoverin−) |
|---|---|---|---|
| CD56 (NCAM) | Neuron cell surface adhesion molecule facilitating neurite outgrowth and progression of aging on the visual system | 37.5 | 61.4 |
| CD57 (LAMP-3) | hiPSC-derived cone photoreceptor surface marker. | 35.2 | 47.6 |
| CD81 | Tetraspanis protein localizing to both apical and basolateral plasma membrane domains of post-mitotic RPE | 36.7 | 50.3 |
| CD111 (Nectin 3) | Nervous system development: | 19.1 | 1.6 |
| CD133 (clone AC133) | Retinal development | 9.1 | 1.5 |
| CD133 (clone 293C3) | Retinal development | 9.7 | 1.8 |
| CD147 | Functions in adhesion | 38.1 | 43.5 |
| CD184 (CKCR4) | Chemokine receptor that facilitates cellular chemotactic activity | 32.9 | 51.3 |
| CD200 | Cellular maintenance and retinal homeostasis | 35.9 | 63.2 |
| CD230 | Prion protein | 35.5 | 15.9 |
| CD276 | Cellular activation | 39.7 | 58.7 |
| CD298 | Sodium/potassium-transporting ATPase subunit beta-3 | 36.7 | 60.5 |
| CD344 (Frizzled) | Bipolar cell development. RPE development | 33.3 | 14.1 |
| PSA-NCAM | Functions to protect again light-induced retinal degeneration | 36.1 | 61 |
| PTK7 | Cellular adhesion, signal transduction, RPC | 13.6 | 35.2 |

Investigations into these surface molecules were primarily focused on cellular expression and/or function within the developing or adult retina. Table 4 lists the percent of the cell population that either co-expressed the surface antigen with recoverin or expressed the surface antigen exclusively on off-target differentiated cells, respectively. Percent population expressing either of both markers was determined by flow cytometric analysis of dual-stained D75 PRP product (FIG. 15). Additionally, percent population of cells expressing only recoverin (in FITC, x-axis) or only the surface antigen (in APC, y-axis) was evaluated. All plots were gated against unstained (empty) cells and the corresponding isotype control (REA IgG1, MsIgG1, Ms IgG2a, MsIgG2b, MsIgM). The surface molecules with high recoverin co-expression yet low off-target expression (<20%) include CD11, CD133, CD230, and CD344.

Figure 16:
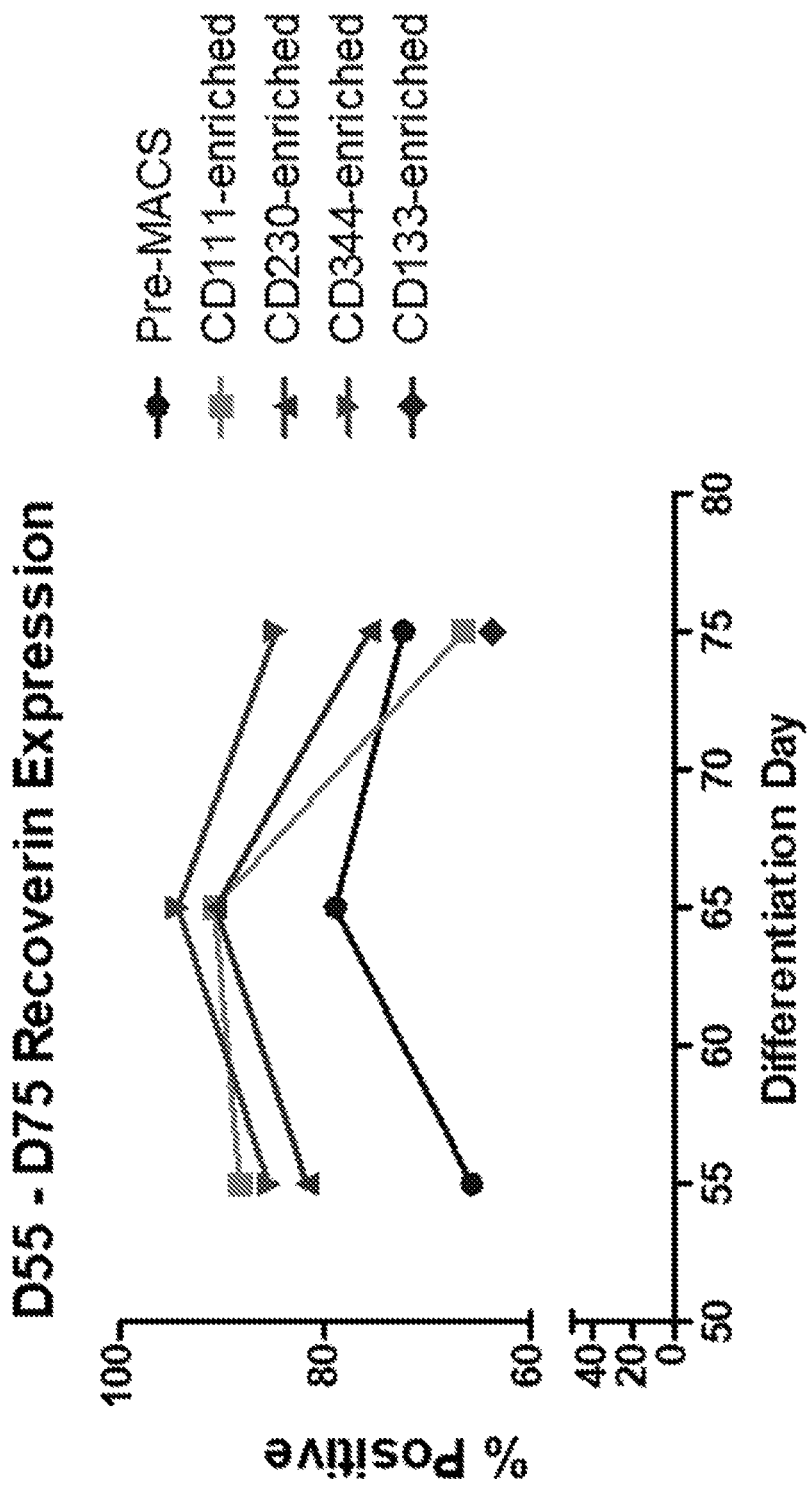
FIG. 16: Time course of recoverin expression following enrichment with surface antigens. Recoverin expression is greatest at D65 for CD344-enriched PRP. Enrichment with CD111 and CD230 also yields high percentage of recoverin expression, compared to pre-enriched (pre-MACS) cells.
Figure 17:
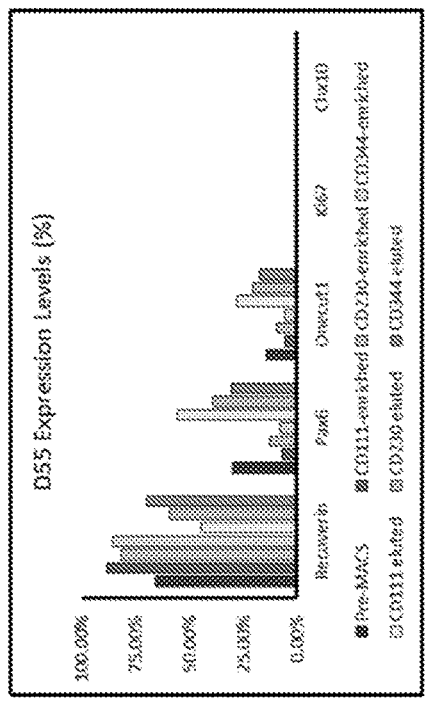
FIG. 17: Post-enrichment expression of on-target PRP and off-target retinal cell evaluation following enrichment with surface antigens CD111, CD230 and CD344 at D55.
Figure 18:
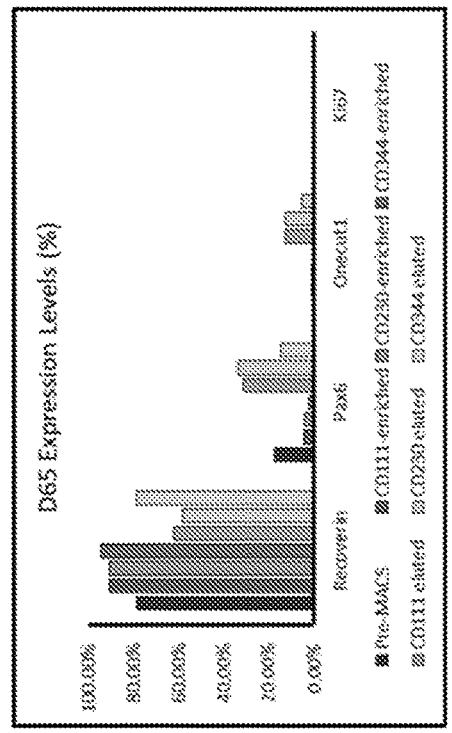
FIG. 18: Post-enrichment expression of on-target PRP and off-target retinal cell evaluation following enrichment with surface antigens CD111, CD230 and CD344 at D65.
Figure 19:
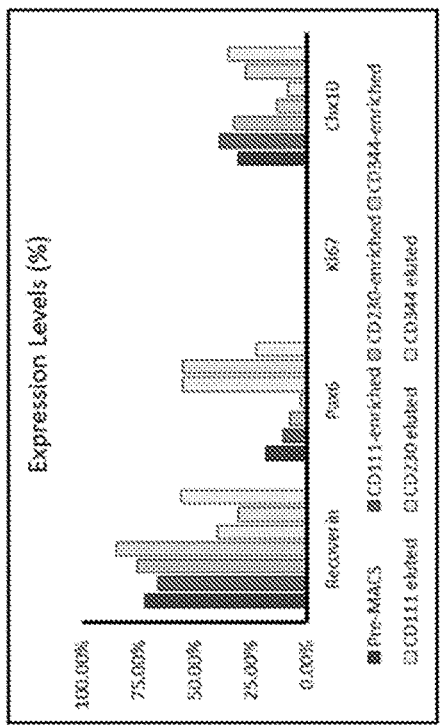
FIG. 19: Post-enrichment expression of on-target PRP and off-target retinal cell evaluation following enrichment with surface antigens CD111, CD230 and CD344 at D75.
Figure 20:
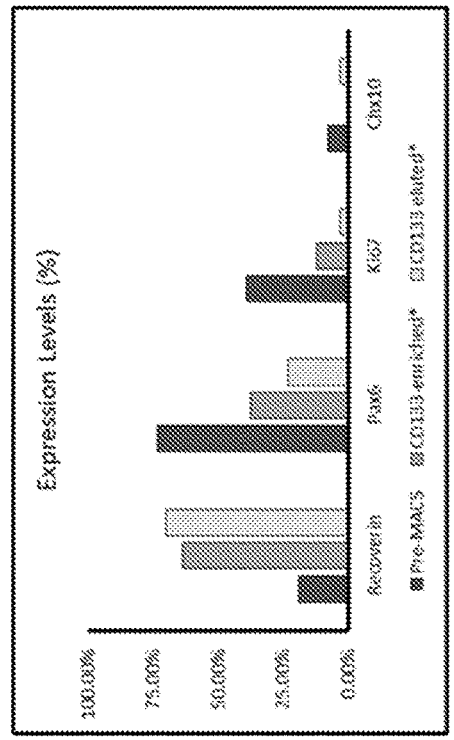
FIG. 20: Post-enrichment expression of on-target PRP and off-target retinal cell evaluation following enrichment with CD133 at D75.

This type of flow cytometric profile increases the likelihood of the antigen being expressed on a greater number of PRP cells and fewer off-target cells. To determine if this was indeed the case, differentiated cells from multiple experiments were enriched for PRP using antibodies against CD111, CD230, CD344 and CD133 surface antigens. FIG. 16 shows recoverin expression at D55, D65 and D75. Recoverin expression peaked at D65 for all conditions, including pre-MACS (CD133-enrichment was only performed on D75 PRP, single time point, diamond) and all a lower fraction than the enriched portion while showing a higher percentage of the off-target marker Onecut1. There were essentially no proliferating cells or CHX10+ RPC/bipolar off-target cells in the cell populations evaluated. Again, the CD344-enriched cells showed the greatest percentage of recoverin-positive expression and low Pax6 and Onecut1. There were no proliferating cells in these cell populations.

There was found to be an overall reduction of on-target and off-target cells by D75, suggesting that the expression of the target markers may have significantly reduced by this time point. Interestingly, CHX10 expression was high, suggestive of possible bipolar off-target cells and/or a possible second wave of progenitor cells.

For all studies, recoverin expression was the greatest post-CD344-enrichment followed by post-CD230-enrichment. CD344 enrichment also reduced Pax6-positive and CHX10-positive off-target cell markers compared to pre-MACS. The elute or flow-through for all three enrichments appeared to contain majority of Pax6+ and CHX10+ cells, suggesting that the enrichment was targeting recoverin+ PRPs and not off-target cells such as retinal ganglion cells (RGCs) or amacrine cells (ACs), both of which express Pax6. Since the enriched portion expressed moderate levels of CHX10 at day 75, some portion of the recoverin-labeled cells may also be co-localized on CHX10-labeled cells, suggesting there was a population of bipolar cells (BPs) in the enriched fraction.

Enrichment using CD133 was done on a different cell line (31538.102) to test whether the line differentiated towards PRP. CD133 enriched for recoverin+ cells and there was an overall reduction in off-target cell marker expression post-enrichment compared to pre-MACS. While Ki67 also reduced post-enrichment, PD0332991 treatment removed any remaining proliferating cells present in the enriched fraction.

Thus, the markers CD71, SUSD2, CD111, CD133, CD230, and CD344 may be used for the enrichment of the PRP cell populations and removal of off-target cells.

Example 8—PRP Enrichment Using CliniMACS®

Further studies were conducted to assess the feasibility of PRP enrichment on a higher throughput scale, such as using the CliniMACS® instrument. PRP enrichment using the CD171 marker was tested using the CliniMACS® instrument whereby the C-1 or C-2 cells were input to the instrument using the CD34.2 or Enrichment 1.1 program with LS tubing. The PRP-enriched cells were then assessed for TUBB3/Nestin and RCVRN. The CliniMACS high-throughput method had similar output purity as compared to the LS Column method with more than 90% of the output cells being neurons and more than 50% of the cells being positive for RCVRN (FIGS. 3 and 9).

Example 9—Materials and Methods

The flow cytometry wash buffer was prepared by adding 20 mL FBS or human serum albumin to 1000 mL of DPBS (i.e., without calcium and magnesium). The buffer was filter sterilized and can be stored at 4° C. for up to 4 weeks.

The flow cytometry permeabilization buffer was prepared by adding 20 mL FBS to 1000 mL DPBS (i.e., without calcium and magnesium). One gram of Saponin was added and mixed well. The buffer was filter sterilized and can be stored at 4° C. for up to 4 weeks.

The flow cytometry Live-Dead Red stain was prepared by diluting Live-Dead Stain 1:1000 in DPBS (i.e., without calcium and magnesium). One mL of the stain was prepared per 2×10$^6$ cells being assayed. The stain was prepared fresh before use.

The flow cytometry fixation buffer was prepared by adding 110 μL of 36.5% Formaldehyde to 880 μL of DPBS (i.e. without calcium and magnesium). One mL of stain was prepared per 2×10$^6$ cells being assayed. The buffer was prepared fresh before use.

Example 10—Depletion Markers for PRP Enrichment

Figures 1, 21:
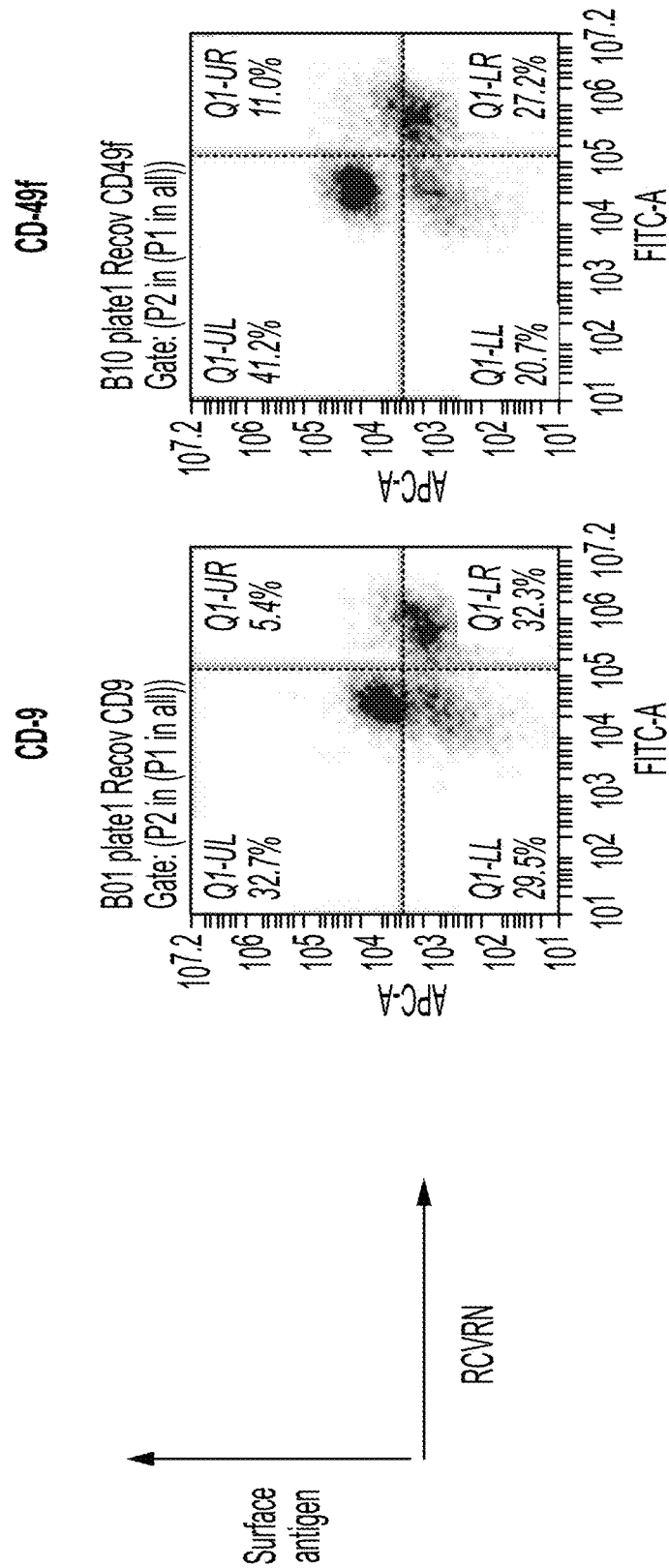
FIG. 21: Flow analyses of depletion markers.
Figures 2, 21:
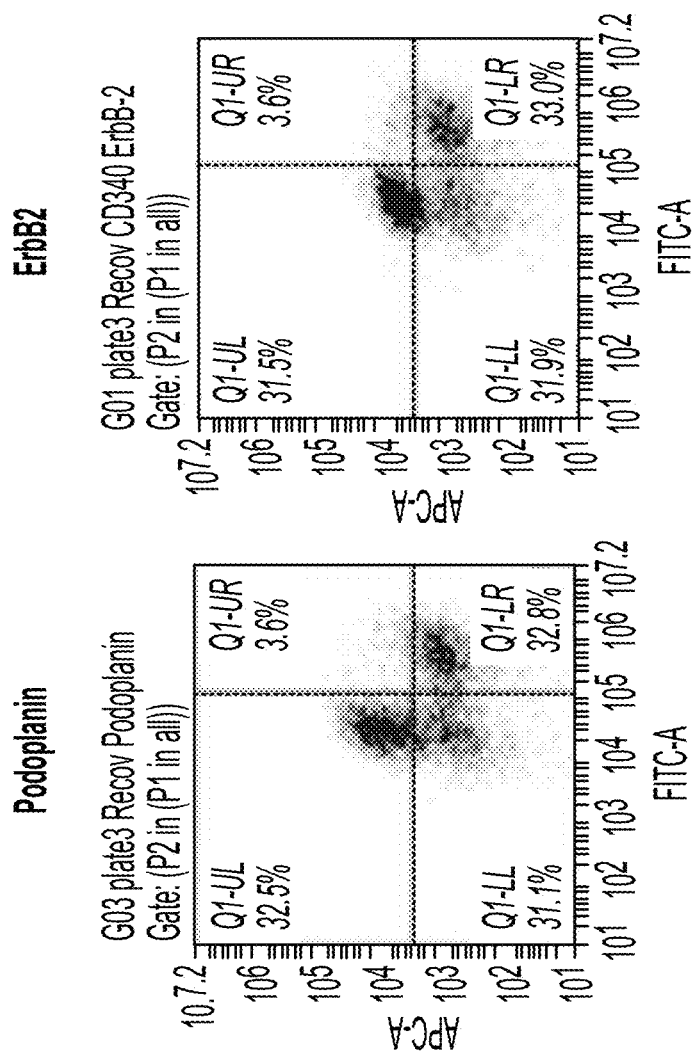
Figures 1, 22:
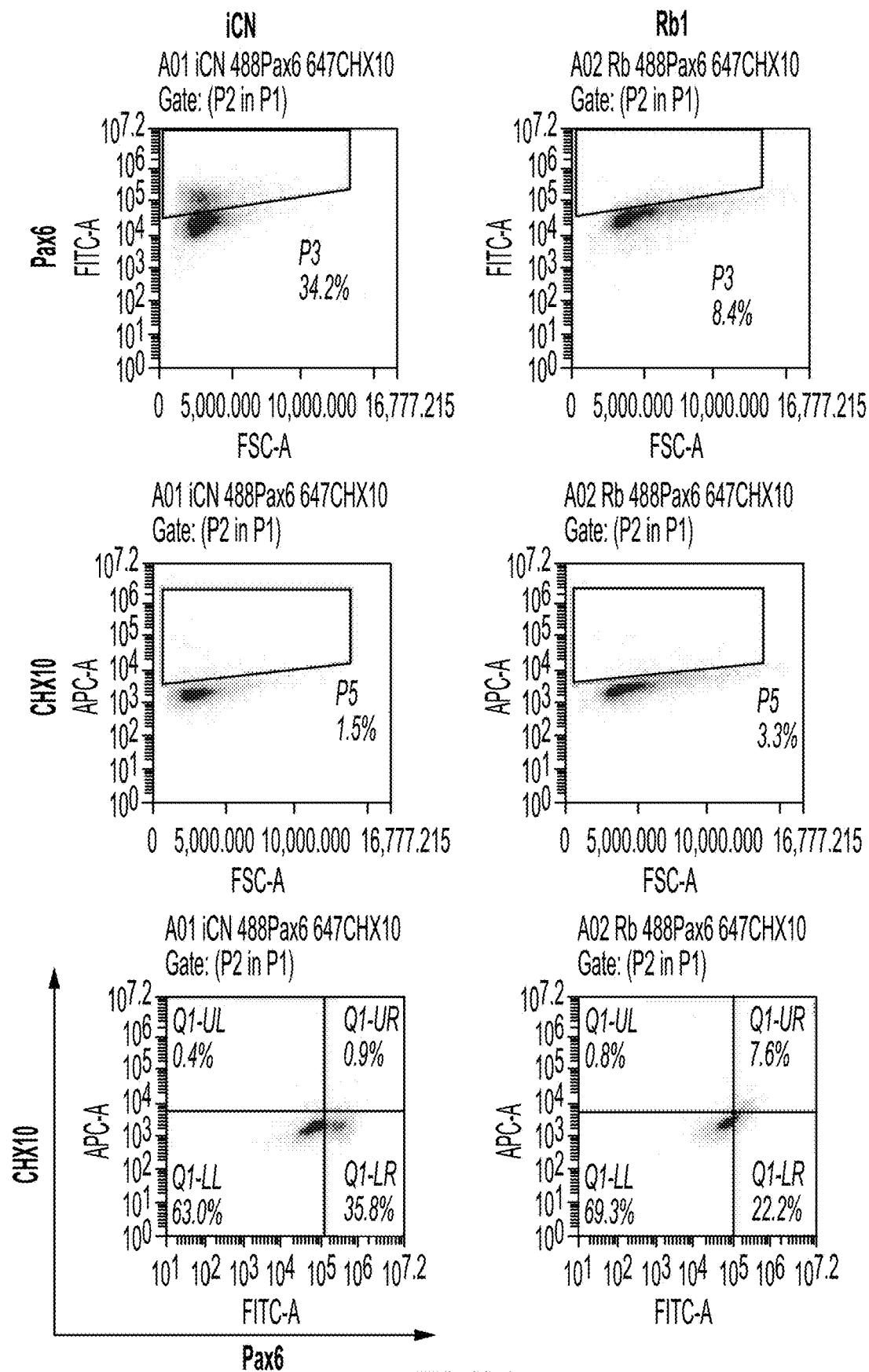
FIG. 22: Flow cytometry analysis of PAX6 and CHX10 expression with or without CKI-7 at Day 15 and Day 25 of PRP differentiation.
Figures 2, 22:
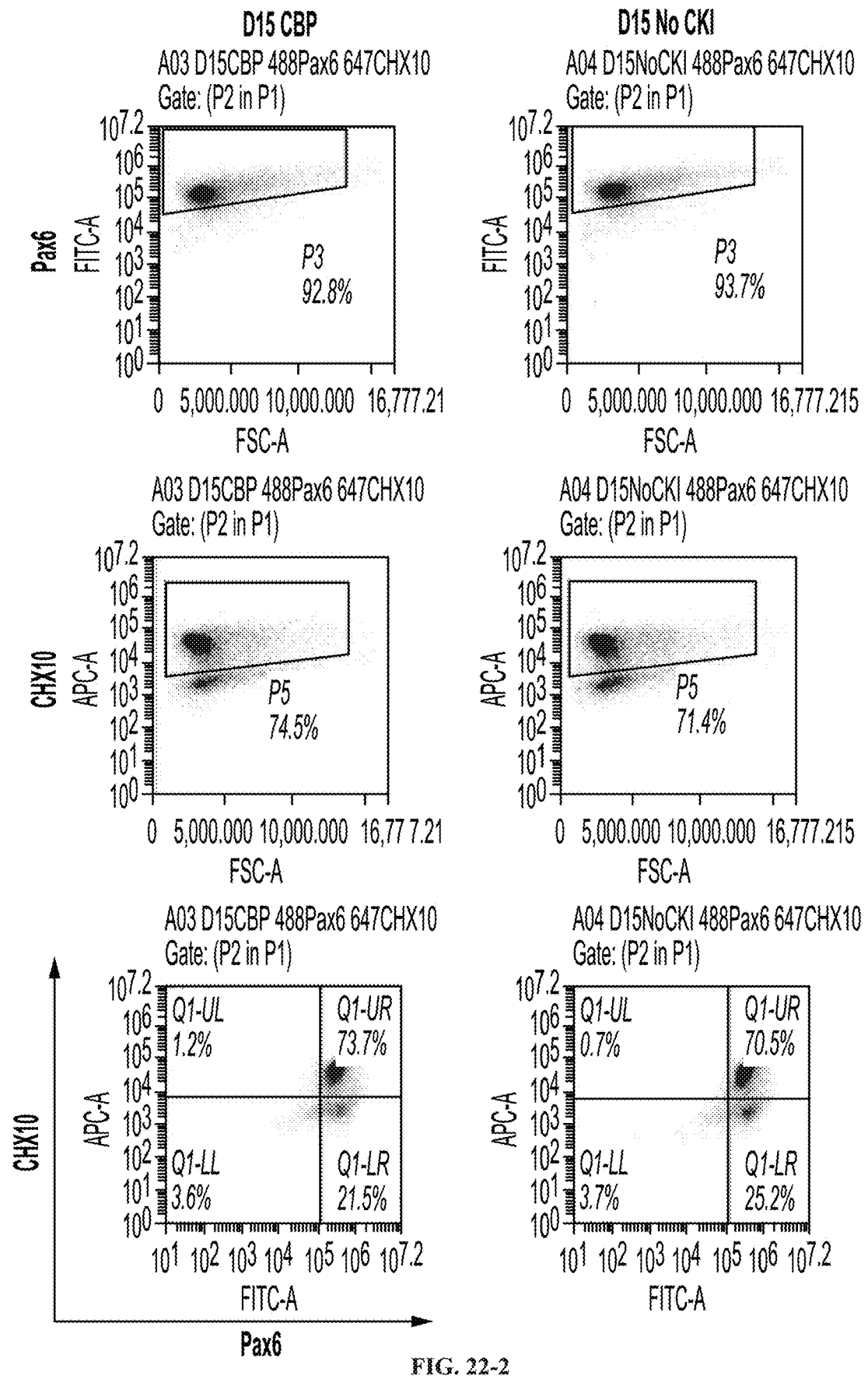
Figures 3, 22:
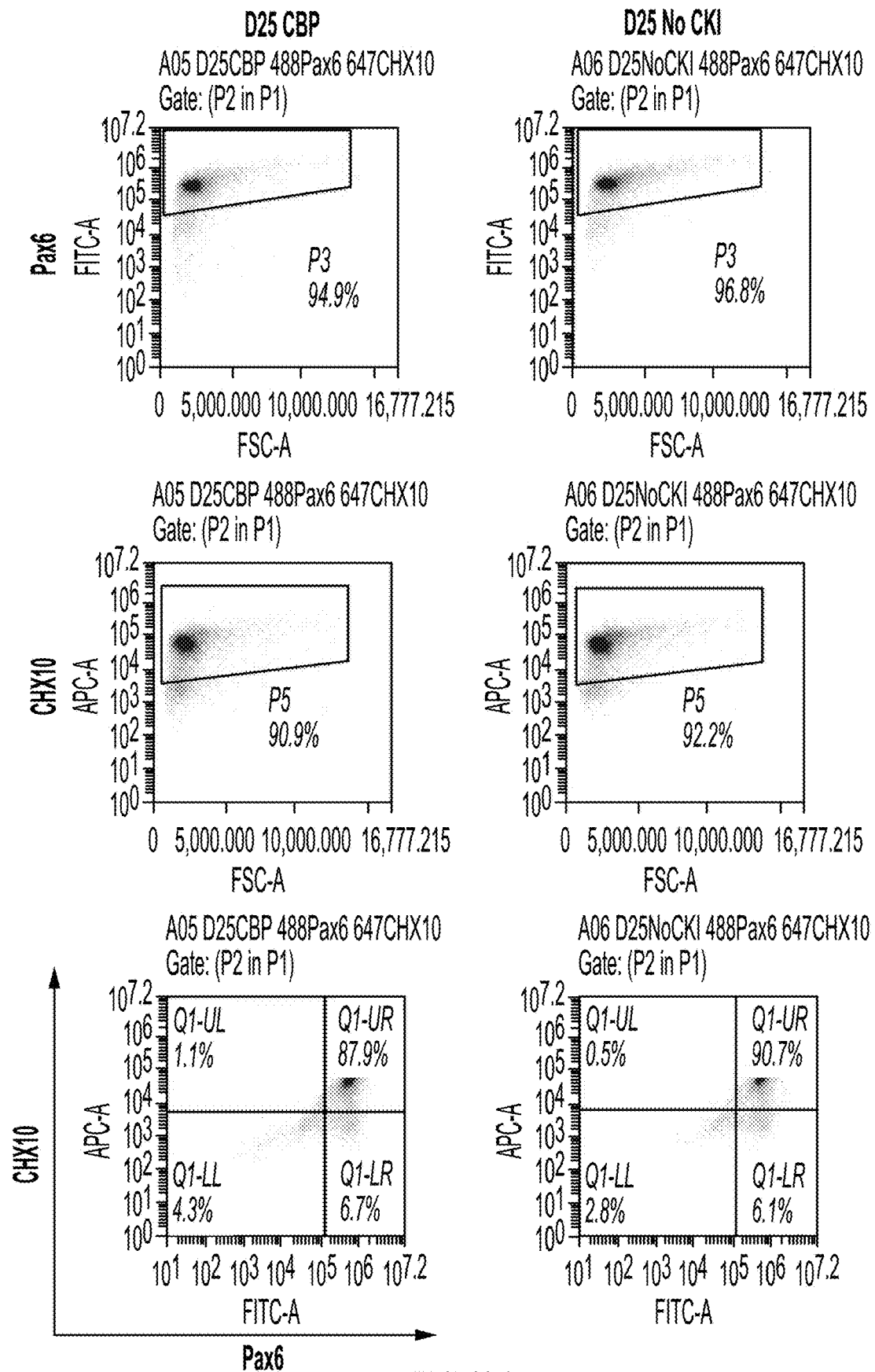
Figure 23:
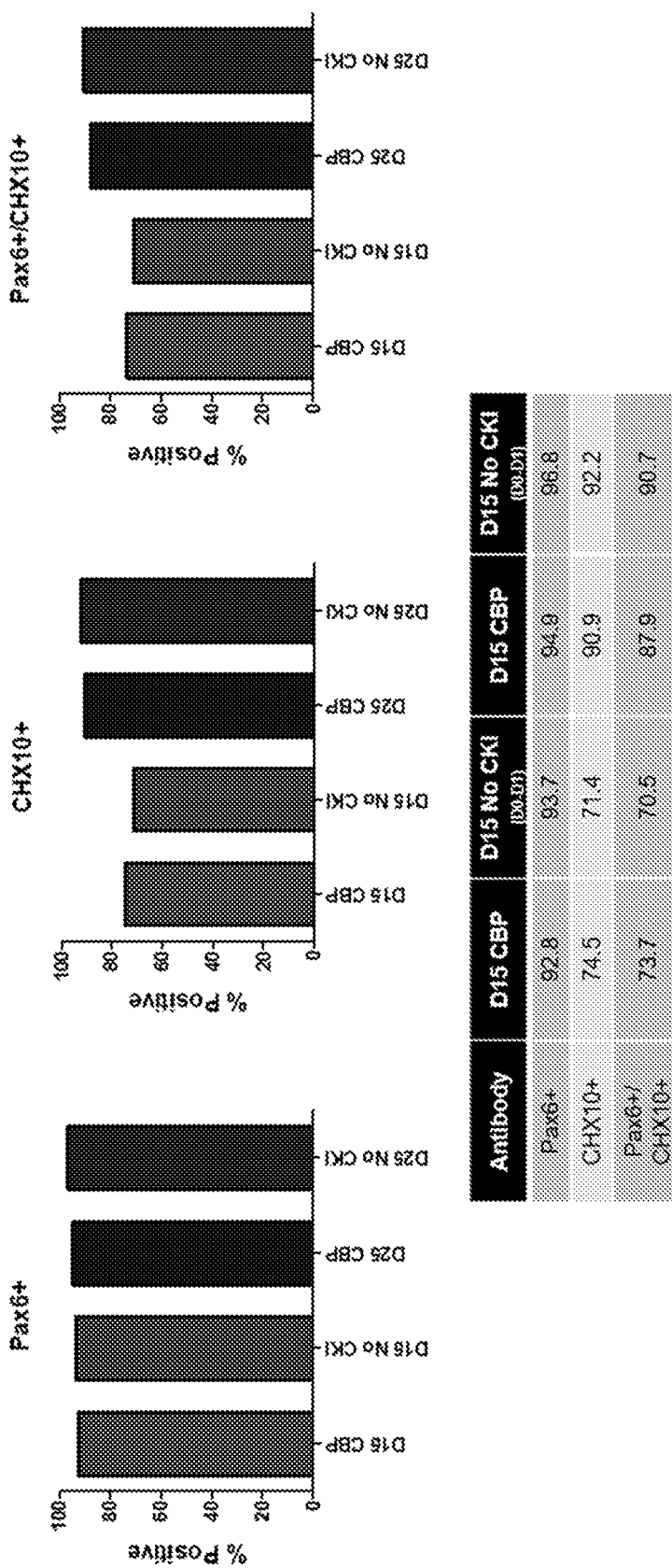
FIG. 23: Percent expression of PAX6 and CHX10 with or without CKI-7 at Day 15 and Day 25 of PRP differentiation.
Figures 1, 24A:
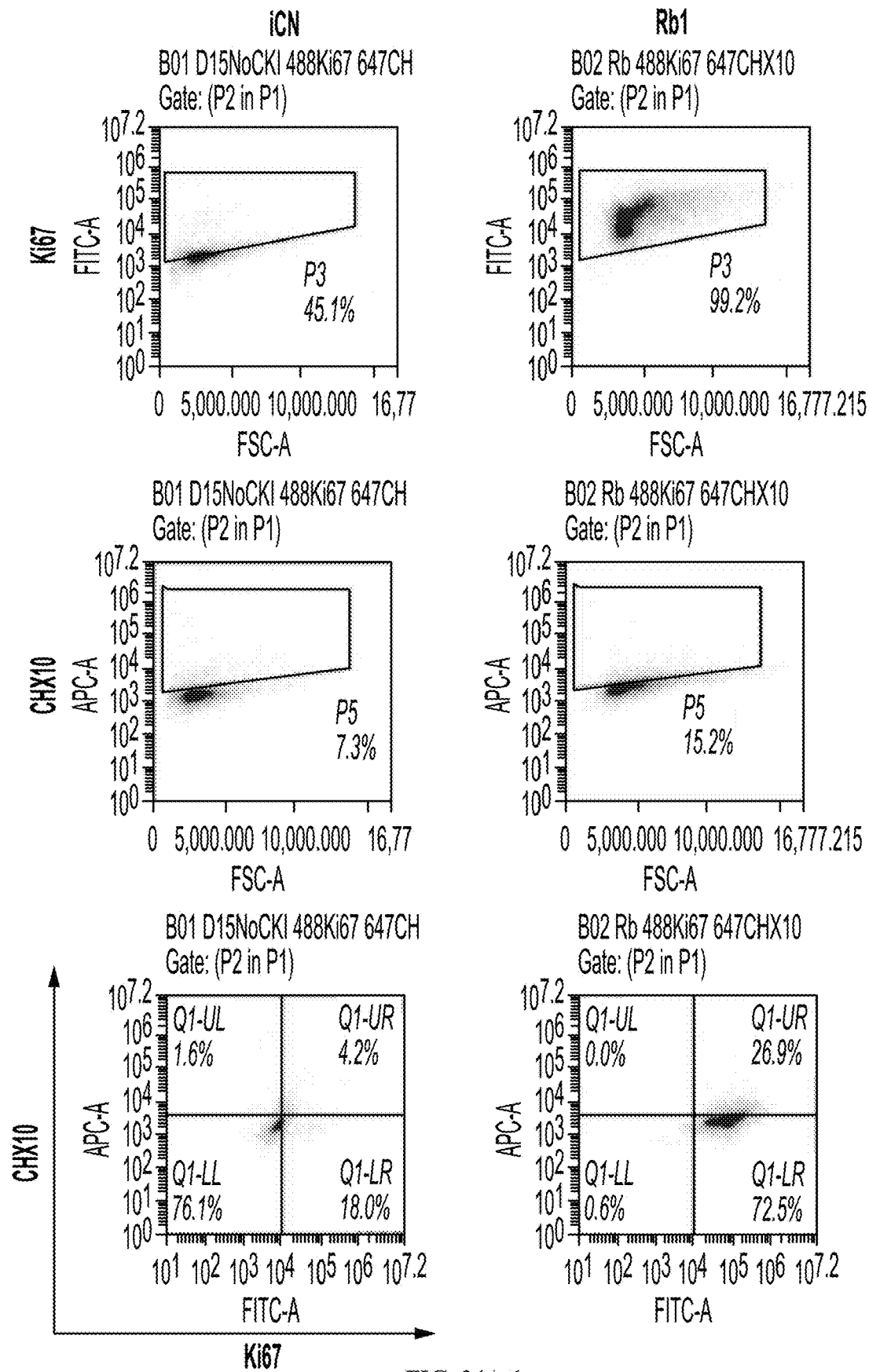
Figures 2, 24A:
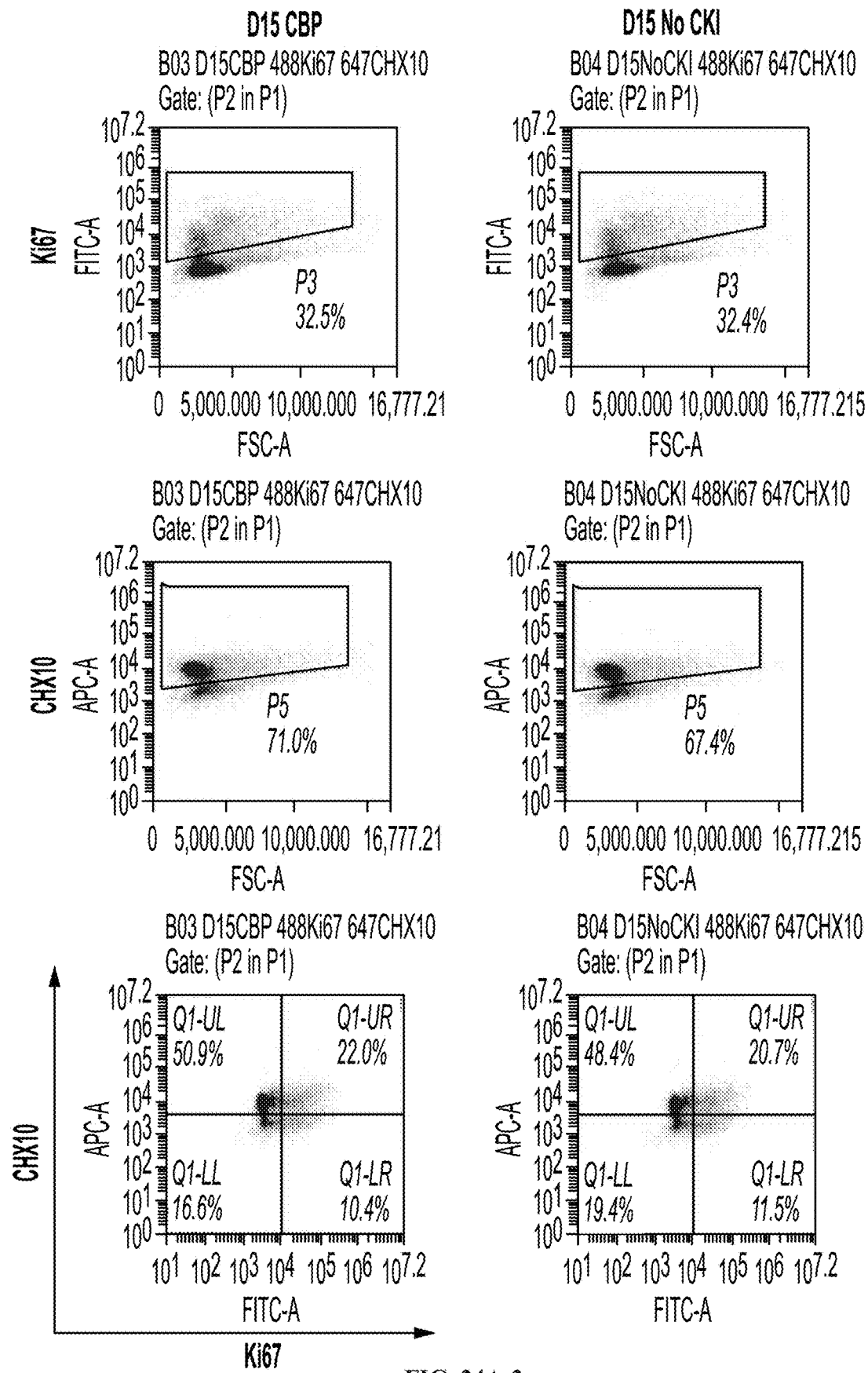
Figures 3, 24A:
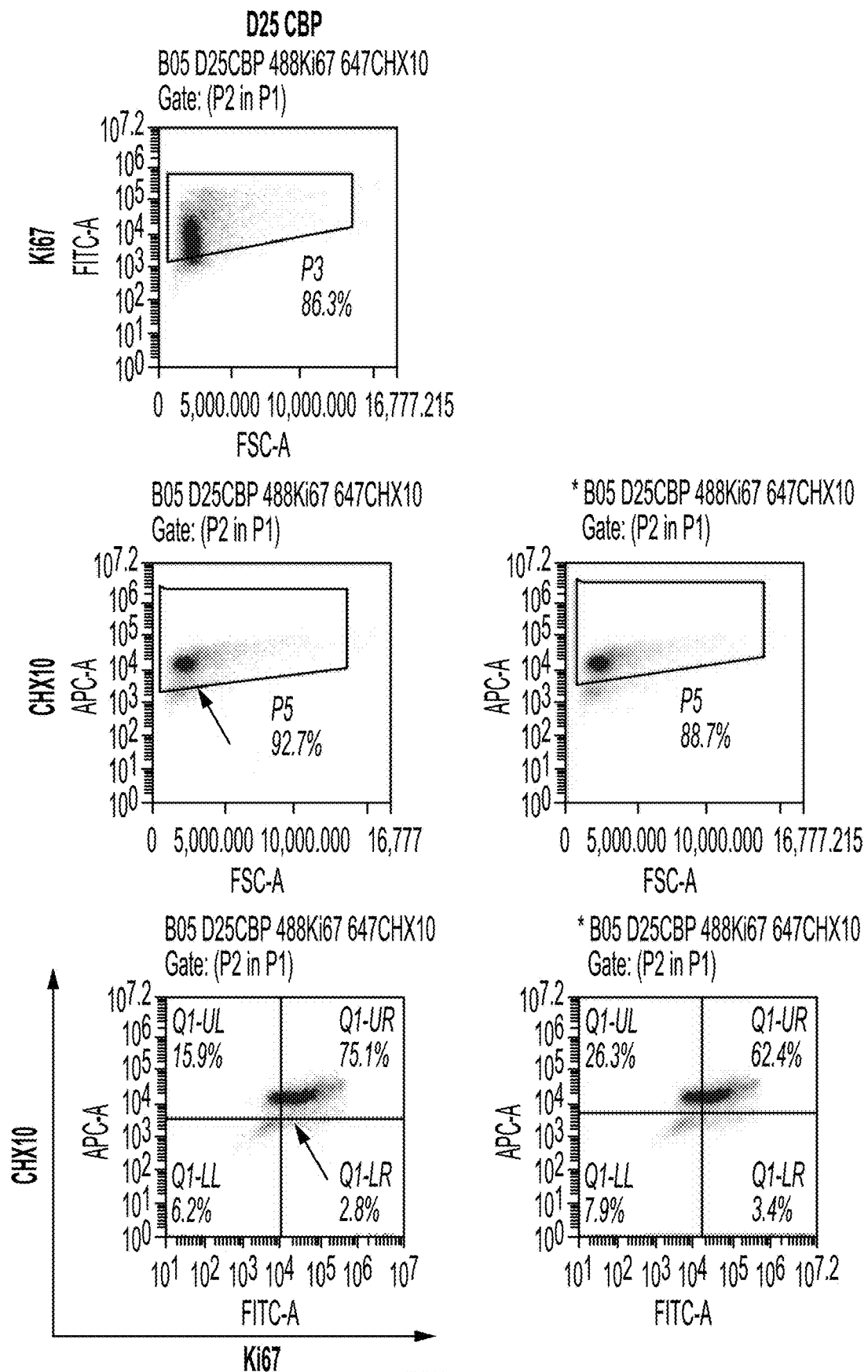
Figures 4, 24A:
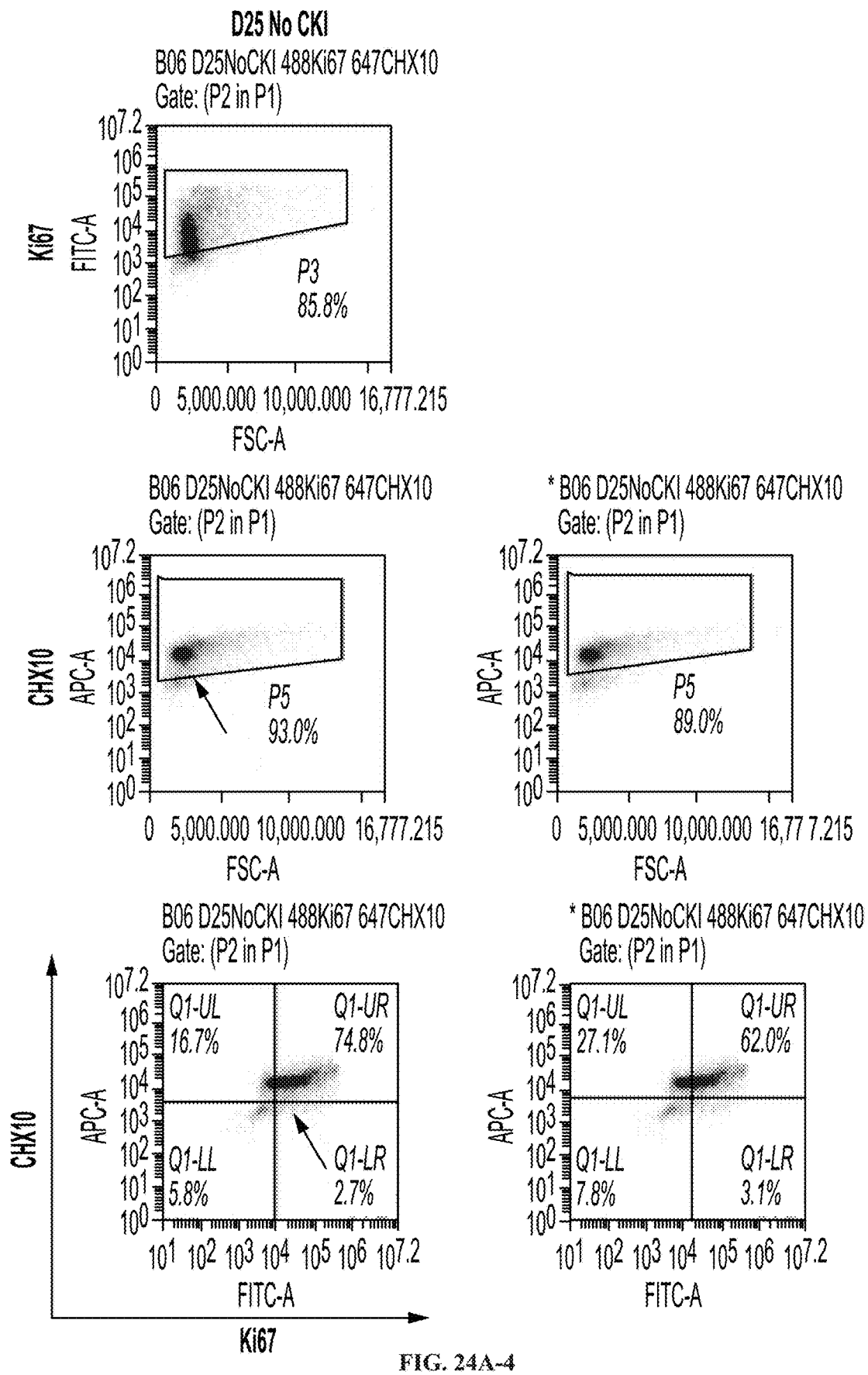
Figures 1, 25A:
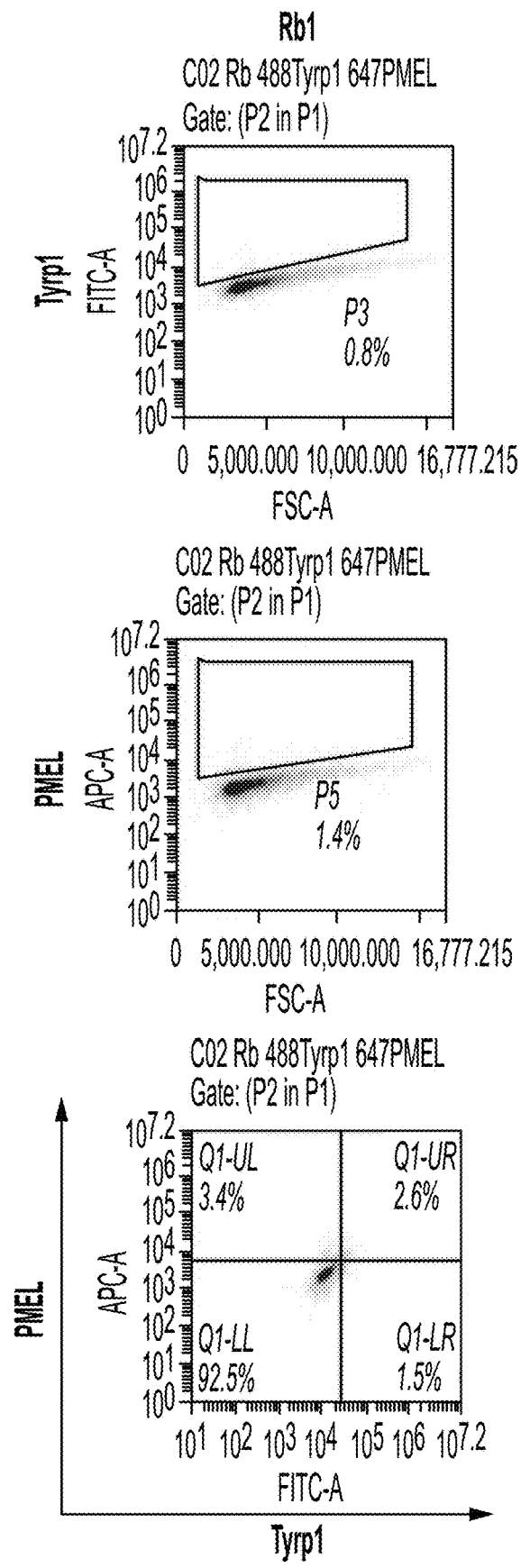
Figures 2, 25A:
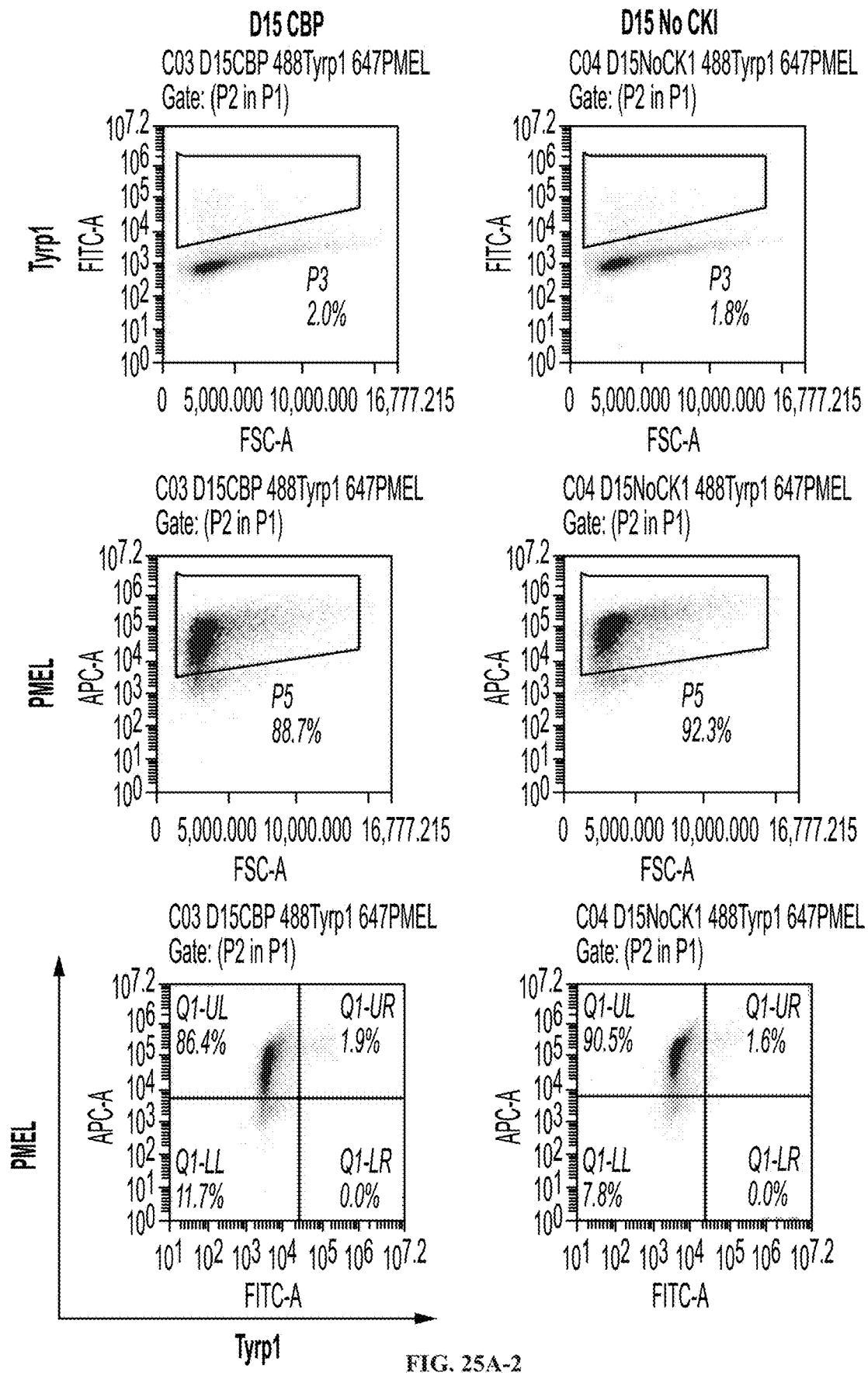
Figures 3, 25A:
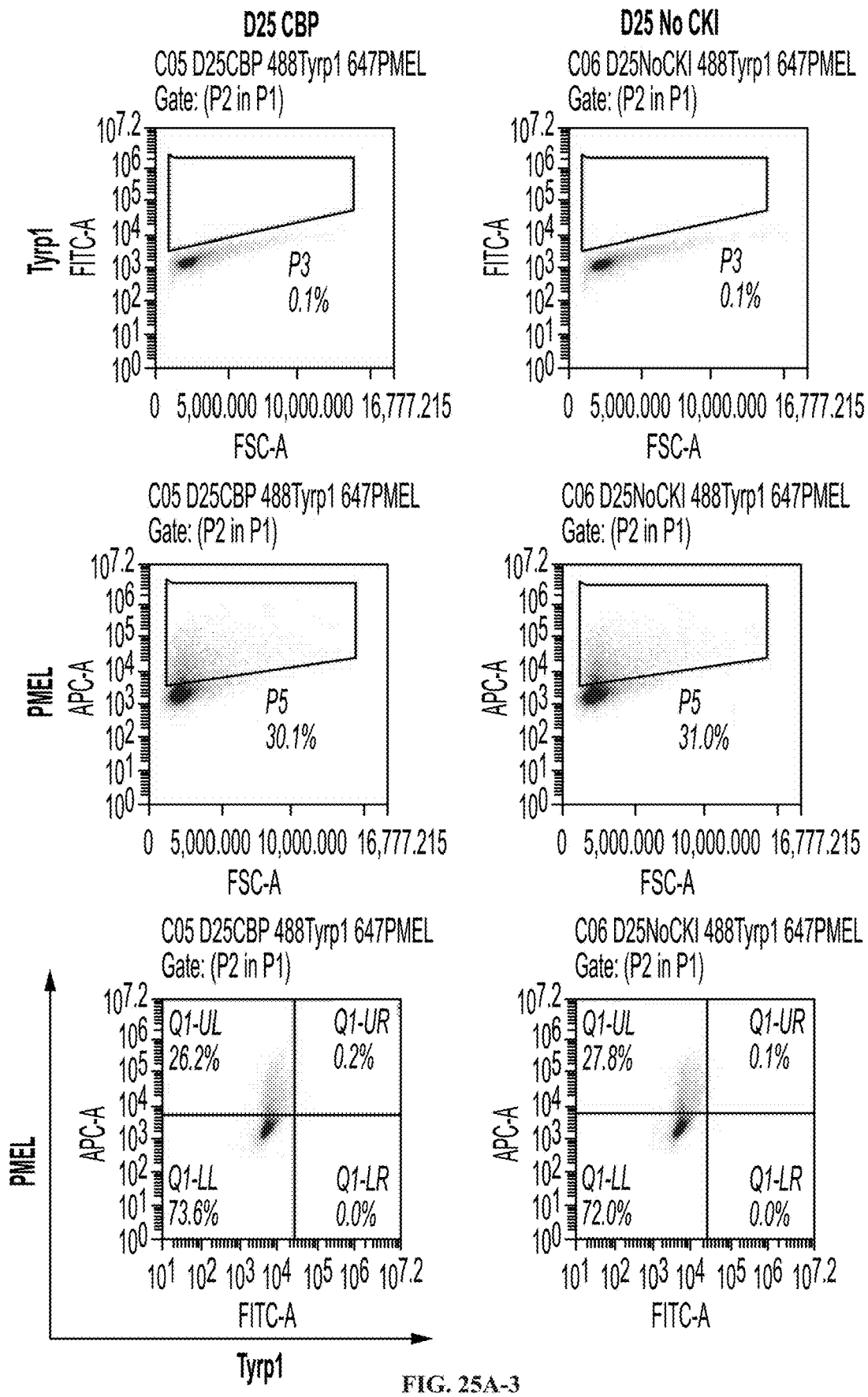

Additionally, surface molecules were identified which could be used as depletion markers to inversely enrich the PRP cell population. These molecules did not show co-expression with recoverin but did label off-target cells, making them good depletion markers for unwanted cell types. Table 5 lists four possible depletion candidates that showed very little co-expression with recoverin (<15%) but labeled other cell types (>30%). Expression profiles of recoverin against the depletion antibodies were evaluated by flow analysis. FIG. 21 shows the low expression or near absence of depletion candidate surface antigen co-expression with recoverin.

TABLE 5

Depletion markers for PRP enrichment.

| Antigen | Description | % co-expression with RCVRN | % antigen only |
|---|---|---|---|
| CD9 | Integral membrane protein associated with integrins | 5.4 | 32.7 |
| CD49f | Integrin alpha 6 | 11 | 41.2 |
| CD340 | Cell surface receptor tyrosine protein kinase ErbB2 | 3.6 | 31.5 |
| Podoplanin | Mucin-type transmembrane protein | 3.6 | 32.5 |

Example 11—Optimization of PRP Differentiation

The PRP differentiation method was further evaluated for use of the Wnt activator, such as CKI-7, at Days 0 and 1. The cells were differentiated in the absence of CKI-7 and characterized for PAX6, CHX10, Ki67, and PMEL expression at Day 15 and Day 25 of the differentiation process. It was found that without CKI-7 at Days 0 and 1, the cell population had a similar expression of PAX6, CHX10, Ki67, and PMEL at Days 15 and 25 (FIGS. 22-25). Thus, the PRP cells may be differentiated in the absence of CKI-7 at Days 0 and 1.

Alternatively, the differentiation method was performed without the use of RIM. Instead, the cells were cultured in the RD1 media supplemented with LDN193189 for Day 0-Day 1 and then cultured in RD2 media without LDN193189 (FIGS. 26-30).

The method of Examples 1-3 was modified to remove the two-day culture in RIM media and the early neural retinal differentiation was evaluated. The cells were directly cultured in the RD1 media with the high concentrations of LDN193189, SB431542, and CKI-7 for Day 0 to Day 1 followed by culture in the RD2 media without LDN193189 Day 2 to Day 10. The cells were aggregated at Day 15 and samples were processed for flow analysis at time of aggregation, at Day 30 mid-process development and Day 75 end-process development.

Figures 26A, 26B:
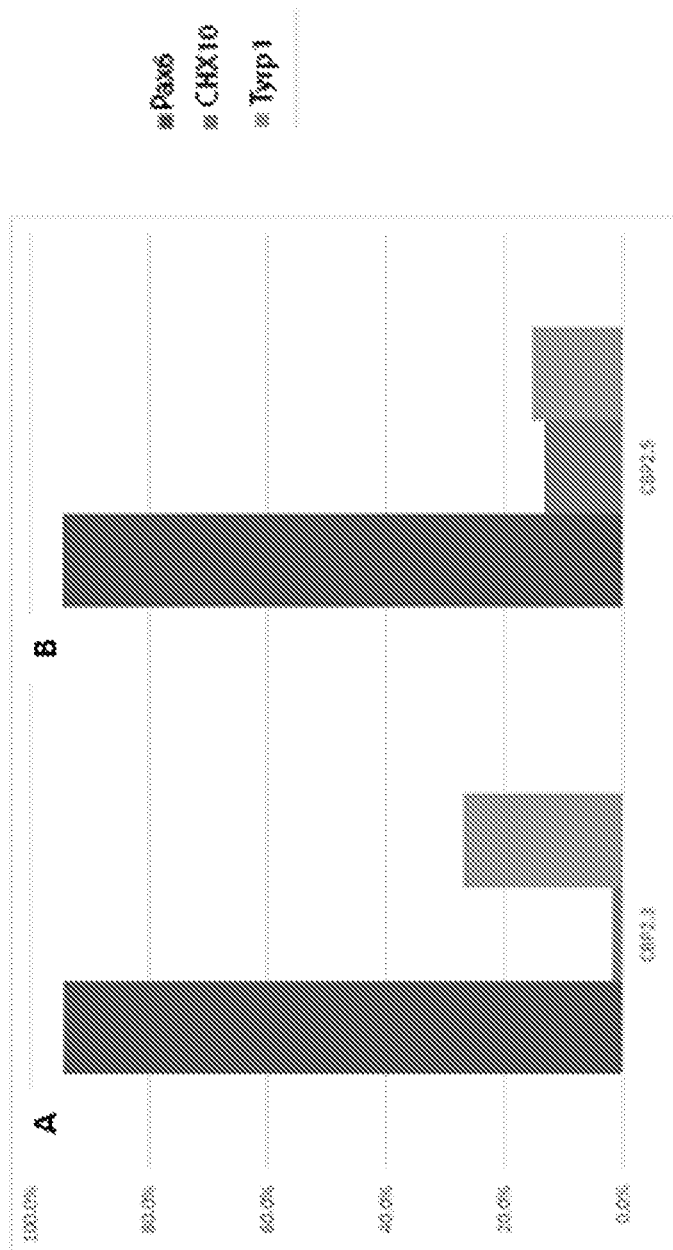
FIGS. 26A-26B: Comparison of early eye field and RPE markers in the presence (FIG. 26A) and absence (FIG. 26B) of RIM.
Figures 27A, 27B, 27C, 27D:
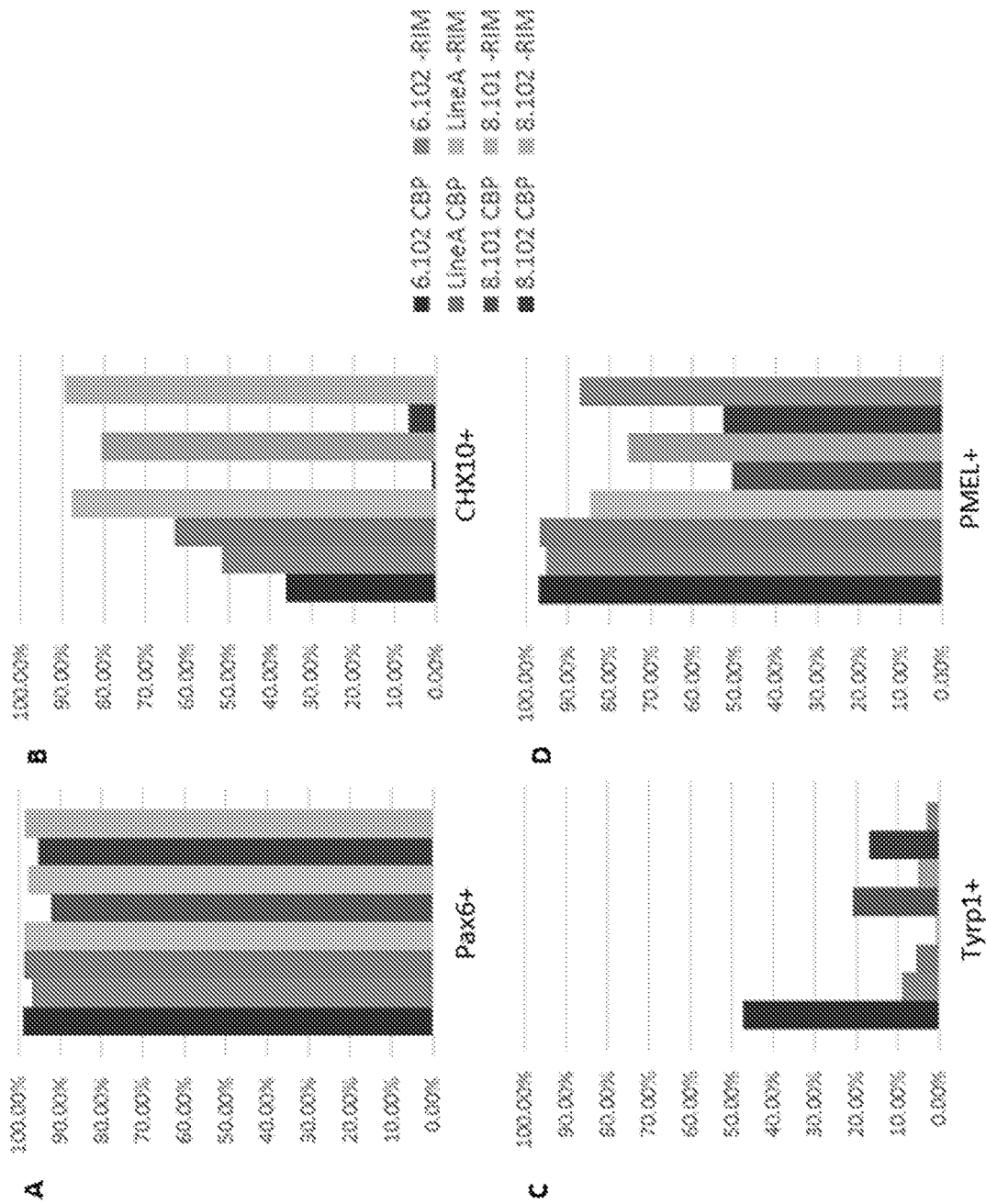
FIGS. 27A-27D: Effects of RIM versus No RIM on early (D15) neural retina differentiation across lines on expression of PAX6 (FIG. 27A), CHX10 (FIG. 27B), TRYP10 (FIG. 27C), and PMEL (FIG. 27D).
Figures 28A, 28B, 28C, 28D:
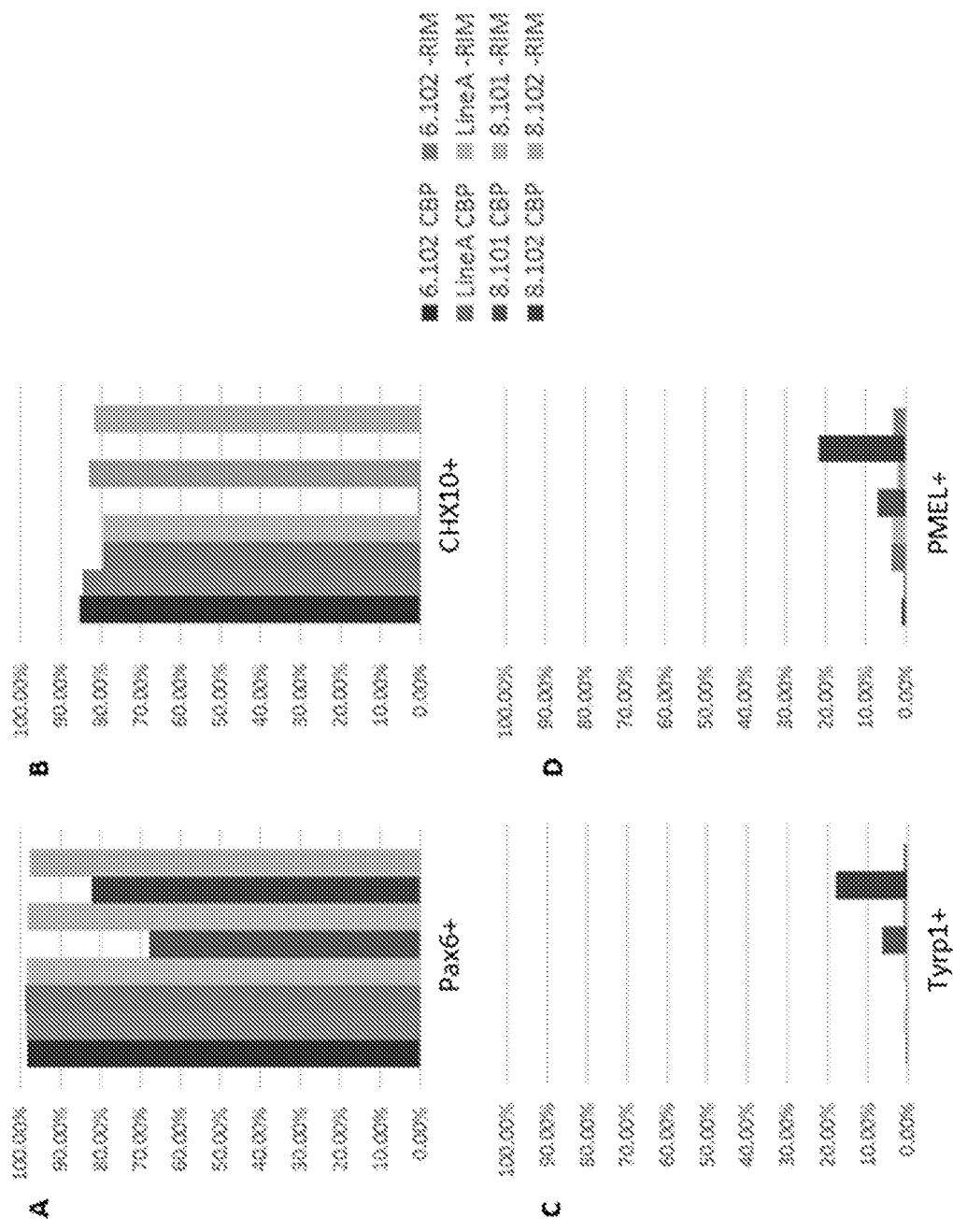
FIGS. 28A-28D: Comparison of mid-stage differentiation (~D30) of PRP in the presence or absence of RIM on expression of PAX6 (FIG. 28A), CHX10 (FIG. 28B), TRYP10 (FIG. 28C), and PMEL (FIG. 28D).

The D15 in-process flow analysis showed that although expression of PAX6, an early human neuroectoderm cell fate determinant, was similar in CBP 2.3 (with RIM) vs CBP 2.5 (without RIM) conditions, expression of early eye field marker CHX10 was low in RIM conditions (FIG. 26). Removal of the RIM step with RD1 with LDN was observed to increase CHX10 expression. Similarly, removal of RIM reduced expression of the RPE marker Tyrp1 by nearly 50% compared to conditions containing RIM (FIGS. 27 and 28).

Multiple cell lines were tested to determine if removal of the RIM promoted PRP differentiation across the various lines. Lines 31536.102, 31538.101 and 31538.102 were lines that consistently expressed low CHX10 at D15 in-process analysis but CHX10 expression in both lines significantly increased when the RIM step was removed (FIG. 27). FIG. 27 compares expression of neuroectoderm marker Pax6, eye field marker CHX10, and RPE markers Tyrp1 and PMEL across 4 lines in the presence of RIM (CBP) or in its absence (–RIM). Across lines, Pax expression was similar in the presence or absence of RIM. CHX10 expression increased across lines when RIM was removed but dramatically improved in lines 8.101 and 8.102, by about 80% in both lines. Co-incidentally, Tyrp1 expression was reduced following removal of RIM.

Pigmented-cell-specific protein (PMEL) is generally associated with RPE pigmentation. In the present differentiation system, it was shown that PMEL expression remains high at D15 and low PMEL expression at D15 usually results in poor PRP differentiation. Removal of RIM does not disrupt PMEL expression in either line 6.102 or line A but markedly increases PMEL expression in lines 8.101 and 8.102. This demonstrated that removal of RIM does not hinder the PRP developmental process but benefits lines which require an extra push towards PRP development. Taken together, the data suggests that removal of RIM may reduce the potential for D15 cells to differentiate into RPE while increasing the possibility of differentiating into PRP.

Based on historical data, during mid-stage (in-process) PRP development (~D30), expression of PAX6 and CHX10 peaks while TYRP1 and PMEL expression further reduces. While the developmental process naturally drives these changes in protein expression, the removal of RIM at the early stages of differentiation provides additional support in lines previously considered unacceptable for PRP differentiation. Early removal of RIM affects D30 mid-stage PRP development in lines 8.101 and 8.102 by increasing PAX6 and CHX10 expression levels and reducing TRYP1 and PMEL expression levels.

Figures 29A, 29B:
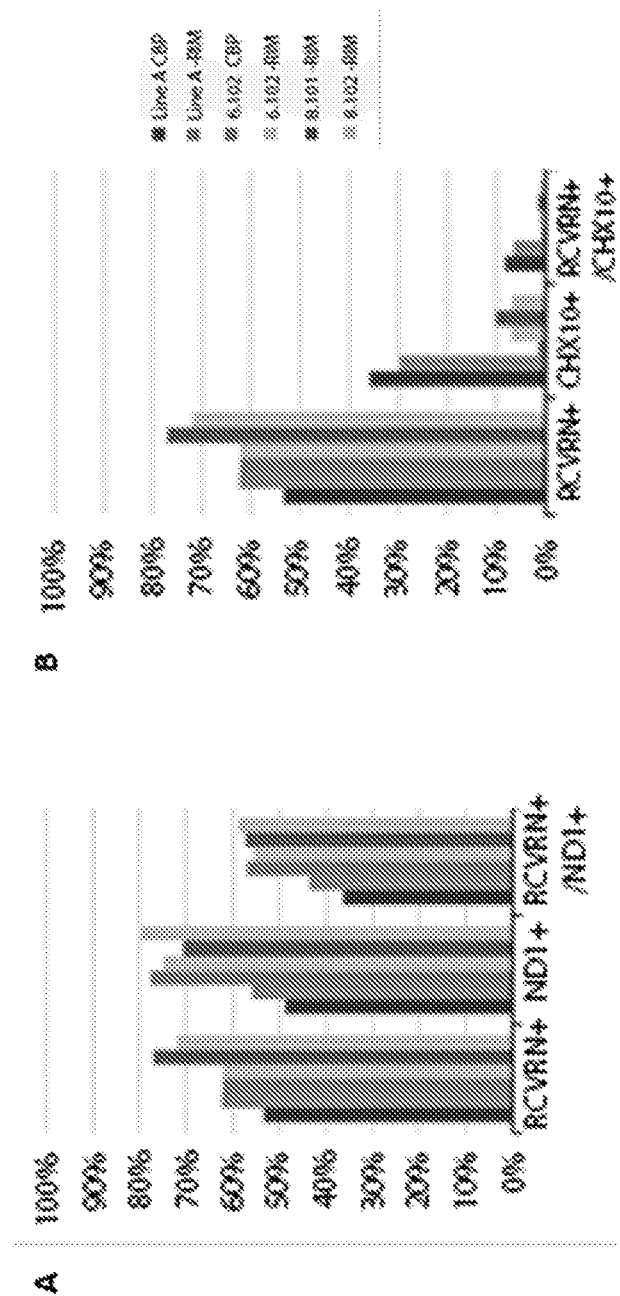
FIGS. 29A-29B: Expression of on-target PRP characterization markers at Day 75 in the presence (FIG. 29A) and absence (FIG. 29B) of RIM.

As the retina develops, a heterogenous population of retinal cells are born in a chronological sequence and characterization of these cell populations are based on a specific panel of antibodies targeted to antigens expressed by the off-target cell types. Current panels to identify on-target PRP cells include recoverin (RCVRN) coupled with either NeuroD1 (neuronal differentiation factor 1, ND1; FIG. 29A) or with CHX10 (FIG. 29B). Recoverin is a neuronal-specific calcium-binding protein that is primarily expressed in photoreceptors and NeuroD1 is a transiently expressed transcription factor that plays a role in the terminal differentiation of photoreceptors. CHX10 coupled with RCVRN is a hallmark characterization marker for (cone) bipolar cells. While CHX10 is expressed early in retinal progenitor cells, it downregulates expression in post-mitotic PRP but remains highly expressed in post-mitotic bipolar cells and some Muller glia cells. Bipolar cells will express both CHX10 and RCVRN while PRP will be only RCVRN+ (positive) and CHX10– (negative). Hence, the dual labeling with RCVRN and CHX10 was used to validate the absence or low presence of bipolar cells in the cell population and demonstrate that RCVRN+ cells are primarily differentiated PRP.

The effect of no RIM on D75 PRP was most evident in Line A, whereby RCVRN and ND1 expression increased with the removal of RIM. This data showed that removal of RIM impacted PRP development. Furthermore, CHX10 expression decreased or remained ≤10% across lines with the removal of RIM, resulting in a reduction of RCVRN+/CHX10+ double-positive cells as well.

Figure 30:
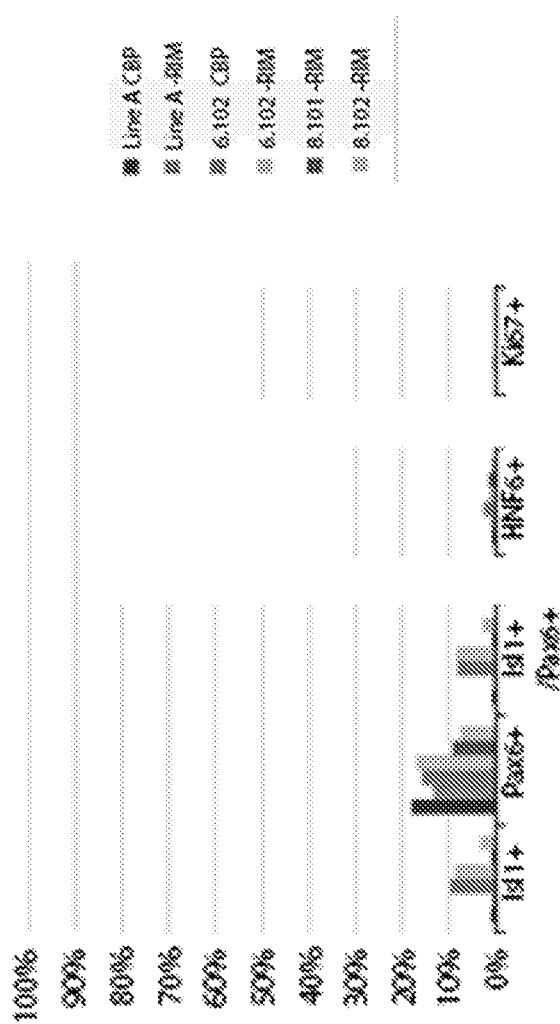
FIG. 30: Expression of off-target retinal cell markers at D75 differentiation in the presence or absence of RIM.

Off-target cell markers include Pax6-Isl1 double-positive for retinal ganglion cells (RGC), HNF6 for horizontal cells and Ki67, a pan proliferative cell marker. Pax6 is also expressed on other mature retinal cells, as described below (FIG. 30). Pax6 is a reliable marker for neural induction but in the retina, several post-mitotic off-target cells express Pax6, such as RGCs, Muller glia and a subset of amacrine cells. Likewise, Isl1 is also expressed by multiple mature off-target retinal cells, such as ON bipolar cells, RGCs and a subset of amacrine cells. At this developmental stage, the no RIM condition did not make much of an impact other than a slight reduction in off-target marker expression. The double positive Isl1/Pax6 population represented a small fraction (≤10%) of lingering RGCs or amacrine cell subset, regardless of the media condition. Additionally, there were negligible HNF6$^+$ horizontal cells and virtually no proliferating cells across lines and conditions.

Thus, the present studies showed that removing RIM from the media sequences used for differentiation significantly impacts PRP differentiation and development, especially in the early developmental stages. The presence of RIM attenuated CHX10 expression at D15 across all lines at in some lines at D30. Removing RIM appeared to "rescue" the reduced CHX10 expression, across lines at D15 and at D30 a significant improvement was observed in lines 8.101 and 8.102. Most importantly, removing RIM increased RCVRN and ND1 expression levels and reduced CHX10 levels in some cases but did not have a disadvantageous effect at any time point observed.

All methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Amit et al., *Dev. Bio.*, 227:271-278, 2000.
Buchholz et al., *Stem Cells*, 27: 2427-2434, 2009.
Byrne et al., *Nature*, 450(7169):497-502, 2007.
Comyn et al., *Curr. Opin. Neurol.* 1, 4-9, 2010.
Gunhan et al., *J Neurosci.* 23(4)1383-1389, 2003.
Haverkamp et al., *J Comp Neurol.* 455(4):463-476, 2003.
Hirami et al., *Neurosci. Lett.*, 48: 126-131, 2009.
Kanemura et al., *PLoS One*, 9, 2014.
Ludwig et al., *Nat. Biotechnol.*, 24:185-187, 2006b.
Ludwig et al., *Nat. Methods*, 3:637-646, 2006a.
Meyer et al., *PNAS*, 106(39): 16698-16703, 2009.
PCT Publication No. WO 2007/069666 A1.
PCT Publication No. WO 2014/121077.
Pearson et al., *Nature* 485, 99-103, 2012.
Smith, In: *Origins and Properties of Mouse Embryonic Stem Cells*, 2000.
Strauss et al., *Physiological Reviews*, 85:845-881, 2005.
Takahashi et al., *Cell*, 126, 663-676, 2006.
Takahashi et al., *Cell*, 131, 861-872, 2007.
Thomson and Marshall, *Curr. Top. Dev. Biol.*, 38:133-165, 1998.
Thomson and Odorico, *Trends Biotechnol.*, 18(2):53-57, 2000.
Thomson et al. *Proc. Natl. Acad. Scie. USA*, 92:7844-7848, 1995.
U.S. Patent Application No. 2002/0076747.
U.S. Patent Application No. 2009/0246875.
U.S. Patent Application No. 2010/0210014.

U.S. Patent Application No. 2012/0196360.
U.S. Patent Application No. 2012/0276636.
U.S. Pat. No. 5,843,780.
U.S. Pat. No. 6,103,470.
U.S. Pat. No. 6,200,806.
U.S. Pat. No. 6,416,998.
U.S. Pat. No. 6,833,269.
U.S. Pat. No. 7,029,913.
U.S. Pat. No. 7,442,548.
U.S. Pat. No. 7,598,364.
U.S. Pat. No. 7,682,828.
U.S. Pat. No. 7,989,425.
U.S. Pat. No. 8,058,065.
U.S. Pat. No. 8,071,369.
U.S. Pat. No. 8,129,187.
U.S. Pat. No. 8,268,620.
U.S. Pat. No. 8,278,620.
U.S. Pat. No. 8,546,140.
U.S. Pat. No. 8,546,140.
U.S. Pat. No. 8,741,648.
U.S. Patent Publication No. 2003/0211603.
U.S. Patent Publication No. 2010/0003757.
Xu et al., *Nat. Biotechnol.*, 19:971-974, 2001.
Ying et al., *Cell*, 115:281-292, 2003.
Yu et al., *Science*, 318: 1917-1920, 2007.
Zhong et., *Nature Communications*, 5:4047, 2014.

What is claimed is:

1. A method for producing a population of neural retinal progenitors (NRPs) comprising:
   (a) obtaining a starting population of human induced pluripotent stem cells (iPSCs);
   (b) culturing the cells in a first retinal differentiation medium (RD1) comprising a BMP inhibitor to further differentiate the cells to anterior neuroectoderm cells;
   (c) inducing retinal differentiation of the anterior neuroectoderm cells by culturing the cells in a second retinal differentiation medium (RD2) essentially free of BMP inhibitors to form retinal progenitor cells (RPCs); and
   (d) culturing the RPCs in a retinal maturation (RM) medium to produce NRPs.

2. The method of claim 1, further comprising culturing the iPSCs in retinal induction medium (RIM) to initiate differentiation of the cells into anterior neuroectoderm cells prior to culturing the cells in RD1.

3. The method of claim 2, wherein the RIM is essentially free of activin A.

4. The method of claim 2, wherein the RIM comprises a BMP inhibitor, a TGFβ inhibitor, and/or IGF-1.

5. The method of claim 4, wherein the RIM further comprises a WNT inhibitor.

6. The method of claim 4, wherein RIM is essentially free of or free of CKI-7.

7. The method of claim 1, further comprising culturing the population of NRPs as suspension aggregates in medium comprising a γ-secretase inhibitor.

8. The method of claim 7, wherein the medium further comprises a ROCK inhibitor or blebbistatin.

9. The method of claim 1, wherein the culturing of steps (a)-(d) is further defined as adherent 2-dimensional culture.

10. The method of claim 1, wherein the RD1 medium comprises IGF-1, a TGFβ inhibitor, a Wnt inhibitor, and a MEK inhibitor.

11. The method of claim 1, wherein the RD2 medium comprises IGF-1, a TGFβ inhibitor, a Wnt inhibitor, and a MEK inhibitor.

12. The method of claim 11, wherein the RD2 medium is essentially free of LDN193189.

13. The method of claim 1, wherein the RM medium comprises nicotinamide and ascorbic acid and is essentially free of Activin A.

14. The method of claim 13, wherein the RM medium further comprises a γ-secretase inhibitor.

15. The method of claim 1, further comprising detecting an increase in VSX2 expression of the anterior neuroectoderm cells to determine differentiation potential.

16. The method of claim 1, wherein at least 90% of the cells after culturing in RD2 express PMEL17.

17. The method of claim 1, wherein at least 30% of the cells after culturing in RD2 express VSX2.

18. The method of claim 1, wherein the RPCs express PAX6, MITF, and/or PMEL.

19. The method of claim 1, wherein at least 70% of the cells after culture in RM express PAX6 and CHX10 (VSX2).

20. The method of claim 1, wherein the NRPs express one or more of the markers selected from the group consisting of PAX6, CHX10 (VSX2), Ki67, and PMEL.

21. A pharmaceutical composition comprising the NRPs produced according to claim 1 and a pharmaceutically acceptable carrier.

22. A method for producing a population of photoreceptor precursor cells (PRPs) comprising:
   (a) obtaining a starting population of NRPs according to claim 1;
   (b) further culturing the NRPs in PRP maturation medium (PM) comprising a γ-secretase inhibitor for a period of time sufficient to produce a population of PRPs.

23. A pharmaceutical composition comprising the PRPs produced according to claim 22 and a pharmaceutically acceptable carrier.

24. A method for producing a population of PRPs comprising:
   (a) obtaining a starting population of NRPs according to claim 1;
   (b) culturing the NRPs as aggregates in RM medium;
   (c) further culturing the NRPs in RM medium comprising a γ secretase inhibitor to produce PRPs; and
   (d) culturing the PRPs in PRP maturation medium (PM) further comprising a cyclin-dependent kinase inhibitor for a period of time sufficient to produce a population of mature PRPs.

25. The method of claim 24, wherein the PM medium further comprises a CDK4/6 inhibitor.

26. The method of claim 24, wherein culturing of step (d) is further defined as adherent 2-dimensional culture.

27. A method for producing a population of optic vesicles (OVs) comprising:
   (a) obtaining a starting population of RPCs according to claim 1; and
   (b) further culturing the RPCs as suspension aggregates in RM medium or PM medium for a period of time sufficient to produce a population of OVs.

28. The method of claim 27, wherein the population of OVs comprises cells at least 50% positive for VSX2 and/or at least 20% positive for RCVRN.

29. A composition comprising an NRP population derived from iPSCs, wherein at least 90% of the cells in the NRP population express PAX6, at least 90% of the cells in the NRP population express PMEL17, and at least 70% of the cells in the NRP population express VSX2.

* * * * *